United States Patent

Matsuo et al.

Patent Number: 5,883,098
Date of Patent: Mar. 16, 1999

[54] PIPERAZINE DERIVATIVES

[75] Inventors: Masaaki Matsuo, Toyonaka; Daijiro Hagiwara, Moriguchi; Takashi Manabe, Kawanishi; Nobukiyo Konishi, Nagaokakyo; Shinji Shigenaga, Kobe; Kenji Murano; Hiroshi Matsuda, both of Osaka; Hiroshi Miyake, Kyoto, all of Japan

[73] Assignee: Fujisawa Pharmaceutical Co., Ltd., Osaka, Japan

[21] Appl. No.: 884,039

[22] Filed: Jun. 27, 1997

Related U.S. Application Data

[63] Continuation of Ser. No. 450,176, May 25, 1995, abandoned, which is a continuation-in-part of Ser. No. 348,176, Nov. 28, 1994, Pat. No. 5,670,505.

[30] Foreign Application Priority Data

| Nov. 29, 1993 | [GB] | United Kingdom | 9324479 |
| Feb. 2, 1994 | [GB] | United Kingdom | 9402010 |
| Jun. 24, 1994 | [GB] | United Kingdom | 9412708 |

[51] Int. Cl.$^6$ .................. A61K 31/495; C07D 417/14
[52] U.S. Cl. ............................ 514/253; 544/369
[58] Field of Search .................... 544/369; 514/253

[56] References Cited

U.S. PATENT DOCUMENTS

| 4,598,079 | 7/1986 | Beyerle et al. | 514/252 |
| 5,053,509 | 10/1991 | Antoine et al. | 544/361 |
| 5,492,912 | 2/1996 | Godfroid et al. | 514/252 |
| 5,500,426 | 3/1996 | Godfroid et al. | 514/252 |
| 5,670,505 | 9/1997 | Matsuo et al. | 514/253 |

FOREIGN PATENT DOCUMENTS

| 0 411 150 | 2/1991 | European Pat. Off. |
| 0 532 456 | 3/1993 | European Pat. Off. |
| 2 230 262 | 10/1990 | United Kingdom |
| 2 271 774 | 4/1994 | United Kingdom |

OTHER PUBLICATIONS

Behun et al, *J. Org. Chem.* pp. 3379–3382 (1961).

*Primary Examiner*—Emily Bernhardt
*Attorney, Agent, or Firm*—Oblon, Spivak, McClelland, Maier & Neustadt, P.C.

[57] ABSTRACT

A piperazine compound of the formula:

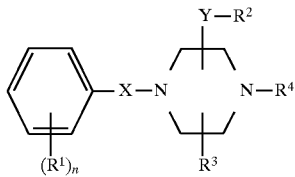

wherein:

X is carbonyl or sulfonyl;

Y is a direct bond or lower alkylene; and $R_1$, $R_2$, $R_3$, $R_4$ are as defined herein. The compounds are advantageously used as Tachykinin antagonists in the treatment of respiratory diseases, ophthalmic diseases and inflammatory diseases, for example.

4 Claims, No Drawings

PIPERAZINE DERIVATIVES

This application is a continuation of application Ser. No. 08/450,176, filed on May 25, 1995, now abandoned; which is a continuation in part of Ser. No. 08/348,176, filed Nov. 28, 1994, now U.S. Pat. No. 5,670,505.

The present invention relates to new piperazine derivatives and a pharmaceutically acceptable salt thereof.

More particularly, it relates to new piperazine derivatives and a pharmaceutically acceptable salt thereof which have pharmacological activities such as Tachykinin antagonism, especially Substance P antagonism, Neurokinin A antagonism, Neurokinin B antagonism, and the like, to a process for preparation thereof, to a pharmaceutical composition comprising the same, and to a use of the same as a medicament.

Accordingly, one object of the present invention is to provide new and useful piperazine derivatives and a pharmaceutically acceptable salt thereof which have pharmacological activities such as Tachykinin antagonism, especially Substance P antagonism, Neurokinin A antagonism, Neurokinin B antagonism, and the like.

Another object of the present invention is to provide a process for the preparation of said piperazine derivatives and a salt thereof.

A further object of the present invention is to provide a pharmaceutical composition comprising, as an active ingredient, said piperazine derivatives and a pharmaceutically acceptable salt thereof.

Still further object of the present invention is to provide a use of said piperazine derivatives or a pharmaceutically acceptable salt thereof as Tachykinin antagonist, especially Substance P antagonist, Neurokinin A antagonist or Neurokinin B antagonist, useful for treating or preventing Tachykinin-mediated diseases, for example, respiratory diseases such as asthma, bronchitis, rhinitis, cough, expectoration, and the like; ophthalmic diseases such as conjunctivitis, vernal conjunctivitis, and the like; cutaneous diseases such as contact dermatitis, atopic dermatitis, urticaria, and other eczematoid dermatitis, and the like; inflammatory diseases such as rheumatoid arthritis, osteoarthritis, and the like; pains or aches (e.g., migraine, headache, toothache, cancerous pain, back pain, etc.); and the like in human being or animals.

The object compound of the present invention can be represented by the following general formula (I):

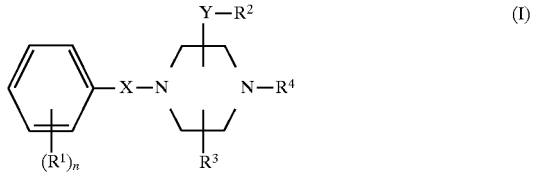

wherein
X is carbonyl or sulfonyl;
Y is bond or lower alkylene;
$R^1$ is halogen, lower alkyl, halo(lower)alkyl, aryloxy, nitro or amino which may have 1 or 2 and same or different substituent(s) selected from lower alkyl, acyl and lower alkanesulfonyl;
$R^2$ is aryl or an aromatic hetero(mono- or bi-)cyclic group, and each of which may have 1, 2 or 3 suitable substituent(s);
$R^3$ is hydrogen or lower alkyl;
$R^4$ is (i) a group of the formula $-SO_2-R^5$
in which $R^5$ is lower alkyl or aryl optionally substituted with lower alkyl or lower alkoxy,
(ii) a group of the formula

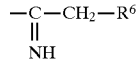

in which $R^6$ is aryl optionally substituted with lower alkyl or lower alkoxy, or
(iii) a group of the formula $-A-(Z)p$
in which
A is bond, lower alkylene, lower alkenylene or lower alkynylene,
Z is hydrogen, halogen, hydroxy, nitrile, amino, cyclo(lower)alkyl, aryl, aryloxy, acyl, acylamino, lower alkanesulfonylamino, arylsulfonylamino or an aromatic hetero(mono- or bi-)cyclic group, and each of the cyclic group may have 1, 2 or 3 suitable substituent(s), and p is 1, 2 or 3; and n is 0, 1 or 2;

provided that when n or p is more than 1, these $R^1$ and Z may be the same or different group respectively;

or its pharmaceutically acceptable salt.

According to the present invention, the object compound (I) or a salt thereof can be prepared by processes which are illustrated in the following schemes.

Process 1

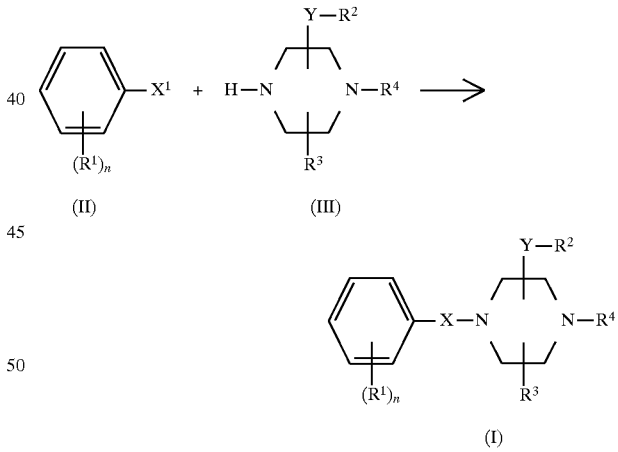

Process 2

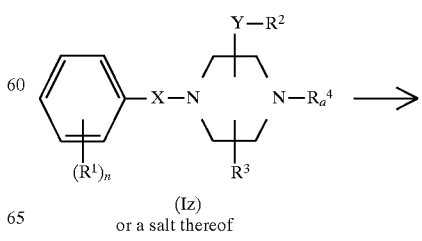

(Iz)
or a salt thereof

-continued
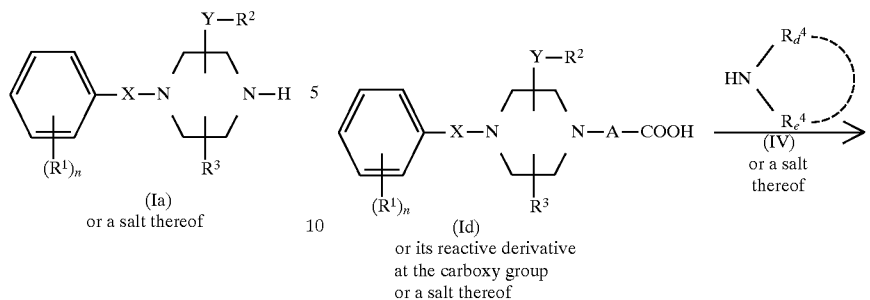
(Ia)
or a salt thereof
Process 3
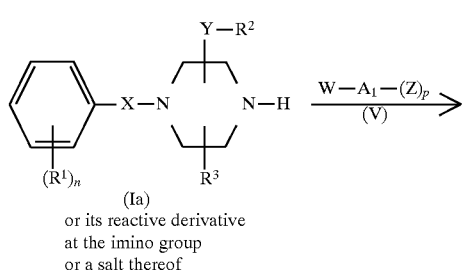
(Ia)
or its reactive derivative
at the imino group
or a salt thereof
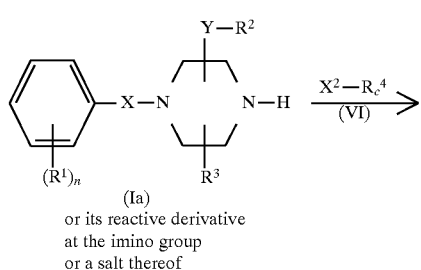
Process 4
Process 5
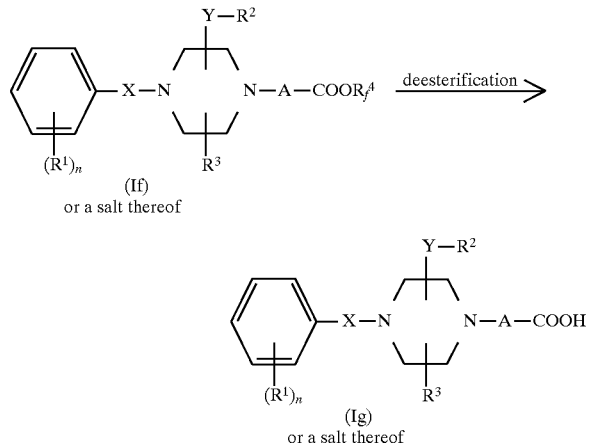
Process 6
Process 7

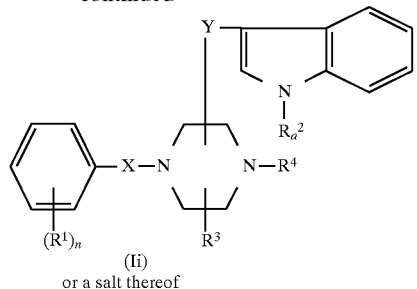

(Ii)
or a salt thereof wherein X, Y, Z, $R^1$, $R^2$, $R^3$, $R^4$, n and p are each as defined above;

$X^1$ is carboxy or its reactive derivative, or sulfo or its reactive derivative;

$X^2$ is a leaving group;

$R_a^2$ is lower alkyl;

$R_a^4$ is an imino-protective group;

$R_c^4$ is
(i) a group of the formula $-SO_2-R^5$
in which $R^5$ is lower alkyl or aryl optionally substituted with lower alkyl or lower alkoxy,
(ii) a group of the formula

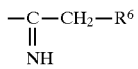

in which $R^6$ is aryl optionally substituted with lower alkyl or lower alkoxy, or
(iii) acyl;

$R_d^4$ and $R_e^4$ are independently hydrogen or an organic group, or $R_d^4$ and $R_e^4$ together with the nitrogen atom form a N containing saturated heterocyclic group which may be substituted by 1 to 3 and same or different suitable substituent(s);

$R_f^4$ is lower alkyl or ar(lower)alkyl;

$A_1$ is lower alkylene, lower alkenylene or lower alkynylene; and

W is a leaving group.

As to the starting compounds (II), (III), (IV), (V), (VI) and (VII), some of them are novel and can be prepared by the procedures described in the Preparations and Examples mentioned later or a conventional manner.

Throughout the present specification, the amino acid, peptides, protective groups, condensing agents, etc. are expressed by the abbreviations according to the IUPAC-IUB (Commission on Biological Nomenclature) which are in common use in the field of this art.

Suitable salts and pharmaceutically acceptable salts of the starting and object compounds are conventional nontoxic salt and include an acid addition salt such as an organic acid salt (e.g. acetate, trifluoroacetate, fumarate, maleate, tartrate, methanesulfonate, benzenesulfonate, formate, toluenesulfonate, etc.), an inorganic acid salt (e.g. hydrochloride, hydrobromide, hydroiodide, sulfate, nitrate, phosphate, etc.), or a salt with an amino acid (e.g. arginine, aspartic acid, glutamic acid, etc.), or a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), or the like.

In the above and subsequent descriptions of the present specification, suitable examples and illustrations of the various definitions which the present invention include within the scope thereof are explained in detail as follows.

The term "lower" is intended to mean 1 to 6, preferably 1 to 4 carbon atom(s), unless otherwise indicated.

Suitable "lower alkylene" is straight or branched one having 1 to 6 carbon atom(s) and may include methylene, ethylene, trimethylene, propylene, tetramethylene, methylmethylene, methyltrimethylene, hexamethylene, and the like, in which the preferred one is methylene, ethylene, trimethylene or methylmethylene.

The term "lower alkenylene" means one having one or two double bond(s) in the straight or branched lower alkylene group as defined above.

Suitable "lower alkenylene" may include one having 2 to 6 carbon atoms such as vinylene, 1-propenylene, 2-propenylene, 1,3-butadienylene, 1-methylvinylene, etc.

Suitable "lower alkynylene" may include one having 2 to 6 carbon atoms such as ethynylene, propynylene, 2-penten-4-ynylene, etc.

The term "halogen" is fluoro, chloro, bromo and iodo.

Suitable "lower alkyl" is straight or branched one having 1 to 6 carbon atom(s) and may include methyl, ethyl, propyl, isopropyl, butyl, isobutyl, pentyl, hexyl and the like.

Suitable "halo(lower)alkyl" may include chloromethyl, bromomethyl, fluoromethyl, iodomethyl, trifluoromethyl, dichloromethyl, 2-fluoroethyl, 1-chloroethyl, 2-chloroethyl and the like, in which the preferred one is trifluromethyl.

Suitable "cyclo(lower)alkyl" may include cyclopropyl, cyclobutyl, cyclopentyl, cyclohexyl and the like.

Suitable "aryl" may include phenyl, tolyl, xylyl, mesityl, cumenyl, biphenylyl, naphthyl, and the like, in which the preferred one is $C_6-C_{10}$ aryl and the most preferred one is phenyl.

Suitable "aryloxy" may include phenoxy, tolyloxy, naphthyloxy and the like.

Suitable "aromatic hetero(mono- or bi-)cyclic group" may include unsaturated monocyclic or bicyclic heterocyclic group containing at least one hetero atom such as nitrogen, oxygen and sulfur atoms.

Preferable "aromatic hetero(mono)cyclic group" may include 5- or 6-membered aromatic hetero(mono)cyclic group containing one to four hetero atoms selected from nitrogen, oxygen and sulfur atoms and may be exemplified pyrrolyl, pyridyl, furyl, thienyl, oxazolyl, isooxazolyl, thiazolyl, isothiazolyl, thiadiazolyl, tetrazolyl, pyrimidinyl, pyrazinyl, pyridazinyl and the like.

Preferable "aromatic hetero(bi)cyclic group" may include condensed aromatic heterocyclic group containing one, two or three hetero atoms selected from nitrogen, oxygen and sulfur atoms and may be exemplified benzothienyl, phthalimido, benzofuranyl, indolyl, indolizinyl, isoindolyl, indazolyl, purinyl, quinolizinyl, isoquinolyl, phthalazinyl, quinazolinyl, cinnolinyl, benzoisoxazolyl and the like.

The "aromatic hetero(mono- or bi-)cyclic group" in the definition of $R^2$ or Z may be bonded to the adjacent "Y" or "A" in the formula (I) at the carbon atom or the hetero atom in the heterocyclic ring.

The "aryl" and "aromatic hetero(mono- or bi-)cyclic group" in the definition of $R^2$ may be substituted by 1 to 3 and same or different suitable substituent(s).

Suitable substituents of the "aryl or an aromatic hetero (mono- or bi-)cyclic group" for $R^2$ may include lower alkyl, halogen, halo(lower)alkyl, oxo, amino, lower alkanoylamino (e.g., formylamino, acetylamino, etc.), (mono- or di-)lower alkylamino(lower)alkyl (e.g., 2-dimethylaminoethyl, etc.) and the like.

More preferable "aromatic hetero(mono- or bi-)cyclic group which may have 1, 2 or 3 suitable substituent(s)" may include 1H-1-(lower alkyl)indol-3-yl and the like.

Suitable "lower alkoxy" may include methoxy, ethoxy, isopropyloxy, butoxy and the like.

The "aryl" in the definition of $R^5$ and $R^6$ may be substituted by 1 to 3 and same or different substituent(s) selected from lower alkyl as defined above and lower alkoxy as defined above.

Suitable "lower alkanesulfonylamino" may include mesylamino, ethanesulfonylamino and the like.

Suitable "arylsulfonylamino" may include phenylsulfonylamino, naphthylsulfonylamino and the like.

The "amino" in the definition of $R^1$ may have 1 or 2 and same or different substituent(s) selected from lower alkyl as defined above, lower alkanesulfonyl (e.g., mesyl, ethanesulfonyl, and the like) and acyl as defined below (e.g., lower alkanoyl and the like).

Preferable "amino which may have 1 or 2 and same or different substituent(s)" may be exemplified methylamino, dimethylamino, formylamino, acetylamino, N-formyl-N-methylamino, mesylamino, and the like.

In the definition of "Z", the "cyclic group" such as "cyclo(lower)alkyl, aryl, aryloxy, arylsulfonylamino or an aromatic hetero(mono- or bi-)cyclic group" may have 1, 2 or 3 and same or different suitable substituent(s).

Preferable substituents of the "cyclic group" in the definition of "Z" may include halogen, lower alkyl, halo(lower)alkyl, lower alkoxy, lower alkanesulfonyl, lower alkanesulfonylamino and arylsulfonylamino as each as defined above, hydroxy, nitro, lower alkanoylamino, cyano, amino, acyl as defined below (e.g., carboxy, lower alkoxycarbonyl, carbamoyl, (mono- or di-)lower alkylcarbamoyl, lower alkanoyl, etc.), acylamino as defined below (e.g., lower alkanoylamino such as acetylamino, etc.), (mono- or di-) lower alkylamino (as described below), N-(lower)alkanoyl-N-(lower)alkylamino (e.g., N-acetyl-N-methylamino, N-propionyl-N-methylamino, etc.), and the like.

Suitable "acyl moiety" for the "acyl group and acylamino group" in the definition of "Z" may include an aliphatic acyl group, an aromatic acyl group and a saturated heterocyclic carbonyl group and each of which may be substituted by 1 to 3 and same or different suitable substituent(s).

Suitable example of said acyl moiety may include:

(a) aliphatic acyl group (a-1) optionally substituted carboxy or esterified carboxy group Preferable "ester moiety" in the term of "esterified carboxy group" includes the ones such as lower alkyl ester (e.g., methyl ester, ethyl ester, propyl ester, isopropyl ester, butyl ester, isobutyl ester, t-butyl ester, etc.), lower alkenyl ester (e.g., vinyl ester, allyl ester, etc.), lower alkynyl ester (e.g., ethynyl ester, propynyl ester, etc.), and the like, and each of which may be substituted by an aryl which may further be substituted by 1 to 3 and same or different substituent(s) selected from the "Substituent list M" as described below.

(a-2) optionally substituted lower alkanoyl group

Preferable lower alkanoyl group includes formyl, acetyl, propionyl, butyryl, isobutyryl, valeryl, isovaleryl, pivaloyl, etc. and each of which may have 1 to 3 and same or different substituent(s) selected from the "Substituent list Q" as described below.

(a-3) optionally substituted cyclo(lower)alkylcarbonyl group

Preferable cyclo(lower)alkylcarbonyl group includes cyclopropylcarbonyl, cyclobutylcarbonyl, cyclopentylcarbonyl, cyclohexylcarbonyl, etc. and each of which may have 1 to 3 and same or different substituent(s) selected from the "Substituent list M" as described below.

(a-4) optionally substituted lower alkenoyl group

Preferable lower alkenoyl group includes acryloyl, methacryloyl, crotonoyl, isocrotonoyl, etc. and each of which may have 1 to 3 and same or different substituent(s) selected from the "Substituent list Q" as described below.

(a-5) optionally substituted lower alkynoyl group

Preferable lower alkynoyl group includes ethynylcarbonyl, propynylcarbonyl, etc. and each of which may have 1 to 3 and same or different substituent(s) selected from the "Substituent list Q" as described below.

(a-6) carbamoyl derivative illustrated by the formula:

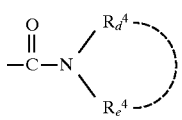

(wherein $R_d^4$ and $R_e^4$ are independently hydrogen or an organic group, or $R_d^4$ and $R_e^4$ together with the nitrogen atom form a "N containing saturated heterocyclic group" which may be substituted by 1 to 3 and same or different substituent(s) selected from the "Substituent list M" as stated below).

Preferable "organic group" for $R_d^4$ and $R_e^4$ is lower alkyl which may be substituted by a group selected from the "Substituent list Q" or a group selected from the "Substituent list Q" as stated below.

Preferable "carbamoyl derivative" includes carbamoyl group, lower alkyl carbamoyl group (e.g., methylcarbamoyl, ethylcarbamoyl, etc.), di-(lower alkyl)carbamoyl group (e.g., dimethylcarbamoyl, diethylcarbamoyl, etc.), and a group of the formula:

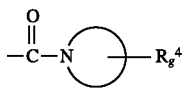

(wherein

is a N containing saturated heterocyclic group and $R_g^4$ is hydrogen or an organic group).

Preferable "organic group" for $R_g^4$ is a group selected from the "Substituent list M" as defined below.

More preferable "N containing saturated heterocyclic group" for

may include 5-, 6- or 7-membered heterocyclic group which contains at least one nitrogen atom as a hetero atom. Most preferable one is 1-pyrrolidinyl, 1-piperidyl, 4-morpholino, 1-piperazinyl, 1-homopiperazinyl, etc., and the heterocyclic group may be substitued by 1 to 3 and same or different substituent(s) selected from the "Substituent list M" as defined below.

(b) aromatic acyl group (b-1) optionally substituted aroyl group

Preferable "aroyl group" includes benzoyl, toluoyl, naphthoyl, etc.

The aroyl group may be substituted by 1 to 3 and same or different substituent(s) selected from the "Substituent list M" as described below.

(b-2) optionally substituted aromatic hetero(mono- or bi-)cyclic carbonyl group

Preferable "aromatic hetero(mono- or bi-)cyclic group moiety" in the "aromatic hetero(mono- or bi-)cyclic carbonyl group" is the one as exemplified before.

The "aromatic hetero(mono- or bi-)cyclic carbonyl group" may be substituted by 1 to 3 and same or different substituent(s) selected from the "Substituent list M" as described below.

(c) optionally substituted saturated heterocyclic carbonyl group

Preferable "saturated heterocyclic group moiety" in the "saturated heterocyclic carbonyl group" may include 5- or 6-membered heterocyclic group which contains at least one nitrogen atom as a hetero atom. Most preferable one is pyrrolidinyl, piperidyl, piperazinyl, etc. and the heterocyclic group may have 1 to 3 and same or different substituent(s) selected from the "Substituent list M" as described below.

Substituent list M aryl; aroyl; aryloxy; lower alkyl optionally substituted by hydroxy; ar(lower)alkyl; carbamoyl; cyclo(lower)alkyl; carboxy; cyano; halogen; hydroxy; lower alkanoyl; lower alkanoyloxy; lower alkoxy; amino optionally substituted by 1 or 2 and same or different substituent(s) selected from lower alkyl, aryl, lower alkanoyl, lower alkanesulfonyl and aroyl; oxo; nitro; lower alkoxycarbonyl; N containing saturated heterocyclic group; or aromatic hetero(mono- or bi-)cyclic group.

Substituent list Q aryl optionally substituted by 1 or 2 of amino, halogen, hydroxy, nitro, halo(lower)alkyl, lower alkoxy, lower alkyl, lower alkanoylamino or (mono- or di-)lower alkylamino; aryloxy; aroyl; lower alkoxy; halogen; hydroxy; carbamoyl; lower alkoxycarbonyl which may be substituted by aryl; amino optionally substituted by 1 or 2 and same or different substituent(s) selected from lower alkyl, aryl, lower alkanoyl, lower alkanesulfonyl and aroyl; ureido; N containing saturated heterocyclic group optionally substituted by lower alkyl, aryl or lower alkanoylamino; carboxy; cyclo(lower)alkyl; or aromatic hetero(mono- or bi-)cyclic group optionally substituted by amino, lower alkyl or lower alkanoylamino.

In the explanation of the above lists of substituent(s), suitable examples and illustrations of the each definitions are the same or equivalent one which are beforementioned, or the one described below:

"(mono- or di-)lower alkylamino" may include lower alkylamino and di(lower alkyl)amino.

suitable "lower alkylamino" may include straight or branched lower alkylamino such as methylamino, ethylamino, isopropylamino, etc., and the lower alkyl moiety may be substituted by 1 to 3 and same or different another substituent(s) selected from the "Substituent list Q", wherein more preferable lower alkylamino is methylamino and benzylamino, suitable "di(lower alkyl)amino" may include straight or branched di(lower alkyl)amino such as dimethylamino, diethylamino, methylethylamino, etc., and the lower alkyl moiety may be substituted by 1 to 3 and same or different another substituent(s) selected from the "Substituent list Q", wherein more preferable di(lower alkyl)amino is dimethylamino and N-methyl-N-benzylamino, etc., suitable "lower alkoxycarbonyl" may include methoxycarbonyl, ethoxycarbonyl, t-butoxycarbonyl, etc.

More preferable compounds of this invention may include the one having the following definition in the general formula (I), X is carbonyl;
Y is lower alkylene;
$R^1$ is halo(lower)alkyl, halogen or amino;
$R^2$ is an aromatic hetero(bi-)cyclic group;
$R^3$ is hydrogen;
$R^4$ is a group of the formula —A—Z in which A is lower alkylene and Z is acyl; and
n is 1 or 2;
or its pharmaceutically acceptable salt.

In the above definitions, each definition is the same as defined above, and acyl moiety for "Z" may include carbamoyl derivatives illustrated by the formula:

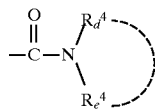

wherein $R_d^4$ and $R_e^4$ are the same as defined above.

Most preferable "acyl moiety" in the definition of "Z" is a group of the formula:

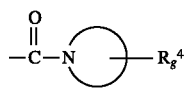

wherein

and $R_g^4$ are the same as defined above.

New piperazine derivatives of this invention may include the one having the following definition in the general formula (I), X is carbonyl;
Y is lower alkylene;
$R^1$ is halo(lower)alkyl;
$R^2$ is an aromatic hetero(bi-)cyclic group;
$R^3$ is hydrogen;
$R^4$ is a group of the formula —A—Z
in which
A is bond or lower alkylene and
Z is acyl or aromatic hetero(mono- or bi-)cyclic group and each of the cyclic group may have 1, 2 or 3 suitable substituent(s); and
n is 1 or 2;
or its pharmaceutically acceptable salt.

In the above definitions, each definition is the same as defined above.

Suitable "leaving group" may include hydroxy, reactive group derived from hydroxy and the like.

Suitable "reactive group derived from hydroxy" may include acid residue and the like.

Suitable "acid residue" may include halogen (e.g. fluoro, chloro, bromo, iodo), acyloxy (e.g. acetoxy, tosyloxy, mesyloxy, etc.) and the like.

Suitable "imino-protective group" may include ar(lower) alkyl such as benzyl, benzhydryl, phenethyl and the like.

The Processes 1 to 7 for preparing the object compound (I) of the present invention are explained in detail in the following.

Process 1

The object compound (I) or a salt thereof can be prepared by reacting a compound (II) or a salt thereof with a compound (III) or its reactive derivative at the imino group or a salt thereof.

Suitable reactive derivative at the imino group of the compound (III) may include Schiff's base type imino or its tautomeric enamine type isomer formed by the reaction of the compound (III) with a carbonyl compound such as aldehyde, ketone or the like; a silyl derivative formed by the reaction of the compound (III) with a silyl compound such as bis(trimethylsilyl)acetamide, mono(trimethylsilyl) acetamide, bis(trimethylsilyl)urea or the like; a derivative formed by reaction of the compound (III) with phosphorus trichloride or phosgene and the like.

Suitable reactive derivative at the carboxy group and the sulfo group of the compound (II) may include an acid halide, an acid anhydride, an activated amide, an activated ester, lower alkyl ester, and the like. Suitable examples of the reactive derivatives may be an acid chloride; an acid azide; a mixed acid anhydride within acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole or tetrazole; or an activated ester [e.g. cyanomethyl ester, methoxymethyl ester, dimethyliminomethyl

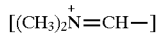

ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from the above according to the kind of the compound (II) to be used.

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound (II) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide; N,N'-diisopropylcarbodiimide; N-ethyl-N'-(3-dimethylaminopropyl)carbodiimide; pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; diphenyl phosphorylazide; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5- (m-sulfophenyl) isoxaozlium hydroxide intramolecular salt; 1-(p-chlorobenzenesulfonyloxy)-6-chloro-1H-benzotriazole; 2-chloro-1-methylpyridinium iodide; 1-(3-dimethylaminopropyl)-3-ethylcarbodiimide hydrochloride; so-called Vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, tri(lower)alkylamine, pyridine, N-(lower) alkylmorpholine, N,N-di(lower)alkylbenzylamine, or the like.

The reaction temperature is not critical, and the reaction is usually carried out under cooling to warming.

Process 2

The object compound (Ia) or a salt thereof can be prepared by subjecting the compound (Iz) or a salt thereof to elimination reaction of the imino-protective group.

In the present elimination reaction, all conventional methods used in the elimination reaction of the imino-protective group, for example, hydrolysis, reduction, elimination using base or acid, etc. are applicable.

Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.), picoline, N-methylpyrrolidine, N-methylmorpholine, 1,5-diazabicyclo[4.3.0]non-5-ene, 1,4-diazabicyclo[2.2.2] octane, 1,5-diazabicyclo[5.4.0]undecene-5 or the like. The hydrolysis using a base is often carried out in water or a hydrophilic organic solvent or a mixed solvent thereof.

Suitable acid may include an organic acid (e.g. formic acid, acetic acid, propionic acid, etc.) and an inorganic acid (e.g. hydrochloric acid, hydrobromic acid, sulfuric acid, etc.).

The present hydrolysis is usually carried out in an organic solvent, water or a mixed solvent thereof.

The reaction temperature is not critical, and it may suitably be selected in accordance with the kind of the imino-protective group and the elimination method.

The elimination using Lewis acid is preferable to eliminate substituted or unsubstituted ar(lower)alkyl ester and carried out by reacting the compound (Iz) or a salt thereof with Lewis acid such as boron trihalide (e.g. boron trichloride, boron trifluoride, etc.), titanium tetrahalide (e.g. titanium tetrachloride, titanium tetrabromide, etc.), tin tetrahalide (e.g. tin tetrachloride, tin tetrabromide, etc.), aluminum halide (e.g. aluminum chloride, aluminum bromide, etc.), trihaloacetic acid (e.g. trichloroacetic acid, trifluoroacetic acid, etc.) or the like. This elimination reaction is preferably carried out in the presence of cation trapping agents (e.g. anisole, phenol, etc.) and is usually carried out in a solvent such as nitroalkane (e.g. nitromethane, nitroethane, etc.), alkylene halide (e.g. methylene chloride, ethylene chloride, etc.), diethyl ether, carbon disulfide or any other solvent which does not adversely affect the reaction. These solvents may be used as a mixture thereof.

The reduction elimination can be applied preferably for elimination of the protective group such as halo(lower)alkyl (e.g. 2-iodoethyl, 2,2,2-trichloroethyl, etc.) ester, ar(lower)alkyl (e.g. benzyl, etc.) ester or the like.

The reduction method applicable for the elimination reaction may include, for example, reduction by using a combination of a metal (e.g. zinc, zinc amalgam, etc.) or a salt of chromium compound (e.g. chromous chloride, chromous acetate, etc.) and an organic or an inorganic acid (e.g. acetic acid, propionic acid, hydrochloric acid, etc.); and conventional catalytic reduction in the presence of a conventional metallic catalyst (e.g. palladium carbon, Raney nickel, etc.).

The reaction temperature is not critical, and the reaction is usually carried out under cooling, at ambient temperature or under warming.

Process 3

The object compound (Ib) or a salt thereof can be prepared by reacting the compound (Ia) or its reactive derivative at the imino group or a salt thereof with the compound (V) or a salt thereof.

Suitable example of the reactive derivative at the imino group of the compound (Ia) is the one as exemplified for compound (III) in the Process 1.

This reaction is usually carried out in a solvent such as alcohol [e.g. methanol, ethanol, etc.], dichloromethane, benzene, N,N-dimethylformamide, tetrahydrofuran, diethyl ether or any other solvent which does not adversely affect the reaction.

The reaction may be carried out in the presence of an inorganic or an organic base such as an alkali metal hydroxide [e.g. sodium hydroxide, potassium hydroxide, etc.], an alkali metal carbonate [e.g. sodium carbonate, potassium carbonate, etc.], an alkali metal bicarbonate [e.g. sodium bicarbonate, potassium bicarbonate, etc.], alkali metal hydride [e.g. sodium hydride, potassium hydride, etc.], tri(lower)alkylamine [e.g. trimethylamine, triethylamine, diisopropylethylamine, etc.], pyridine or its derivative [e.g. picoline, lutidine, 4-dimethylaminopyridine, etc.], or the like. In case that the base to be used in liquid, it can also be used as a solvent.

The reaction temperature is not critical, and the reaction can be carried out under cooling, at room temperature or under warming or heating.

Process 4

The object compound (Ic) or a salt thereof can be prepared by reacting the compound (Ia) or its reactive derivative at the imino group or a salt thereof with the compound (VI) or a salt thereof.

Suitable example of the reactive derivative at the imino group of the compound (Ia) is the one as exemplified in the Process 1.

This reaction can be carried out in substantially the same manner as the Process 1, and therefore the reaction mode and reaction conditions [e.g. solvents, reaction temperature, etc.] of this reaction are to be referred to those as explained in the Process 1.

Process 5

The compound (Ie) or a salt thereof can be prepared by reacting a compound (Id) or its reactive derivative at the carboxy group or a salt thereof with a compound (IV) or a salt thereof.

Suitable example of the reactive derivative at the carboxy group of the compound (Id) is the one as exemplified for compound (II) in the Process 1.

This reaction can be carried out in substantially the same manner as the Process 1, and therefore the reaction mode and reaction conditions [e.g. solvents, reaction temperature, etc.] of this reaction are to be referred to those as explained in the Process 1.

Process 6

The compound (Ig) or a salt thereof can be prepared by subjecting a compound (If) or a salt thereof to deesterification reaction.

The reaction is carried out in accordance with a conventional method such as hydrolysis, reduction or the like.

The hydrolysis is preferably carried out in the presence of a base or an acid including Lewis acid. Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, or the like. Suitable acid may include an organic acid [e.g. formic acid, acetic acid, propionic acid, trichloroacetic acid, trifluoroacetic acid, etc.], an inorganic acid [e.g. hydrochloric acid, hydrobromic acid, hydroiodic acid, sulfuric acid, etc.] and Lewis acid [e.g. boron tribromide, etc.].

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent. The reaction temperature is not critical, and the reaction can be usually carried out under cooling, at ambient temperature or under warming.

The reduction can be applied preferably for elimination of the ester moiety such as 4-nitrobenzyl, 2-iodoethyl, 2,2,2-trichloroethyl, or the like. The reduction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalyst [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.] or the like.

The reduction is usually carried out in a conventional solvent which does not adversely influence the reaction such as water, an alcohol [e.g. methanol, ethanol, propanol, etc.], N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical, and the reaction can be usually carried out under cooling, at ambient temperature or under warming.

Process 7

The object compound (Ii) or a salt thereof can be prepared by reacting the compound (Ih) or a salt thereof with the compound (VII) or a salt thereof.

This reaction can be carried out in substantially the same manner as the Process 3, and therefore the reaction mode and reaction conditions [e.g. solvents, reaction temperature, etc.] of this reaction are to be referred to those as explained in the Process 3.

It is to be noted that the compound (I) and the other compounds may include one or more stereoisomers due to asymmetric carbon atoms, and all of such isomers and mixture thereof are included within the scope of this invention.

The object compound (I) and a pharmaceutically acceptable salt thereof have pharmacological activities such as Tachykinin antagonism, especially Substance P antagonism, Neurokinin A antagonism or Neurokinin B antagonism, and therefore are useful for treating or preventing Tachykinin-mediated diseases, particularly Substance P-mediated diseases, for example, respiratory diseases such as asthma, bronchitis (e.g. chronic bronchitis, acute bronchitis and diffuse panbronchiolitis, etc.), rhinitis, cough, expectoration, and the like; ophthalmic diseases such as conjunctivitis, vernal conjunctivitis, and the like; cutaneous diseases such as contact dermatitis, atopic dermatitis, urticaria, and other eczematoid dermatitis, and the like; inflammatory diseases such as rheumatoid arthritis, osteoarthritis, and the like; pains or aches (e.g. migraine, headache, cluster headache, toothache, cancerous pain, back pain, neuralgia, etc.); and the like.

Further, it is expected that the object compound (I) and a pharmaceutically acceptable salt thereof of the present invention are useful for treating or preventing ophthalmic diseases such as glaucoma, uveitis, and the like; gastrointestinal diseases such as ulcer, ulcerative colitis, irritable bowel syndrome, food allergy, and the like; inflammatory diseases such as nephritis, and the like; circulatory diseases such as hypertension, angina pectoris, cardiac failure, thrombosis, Raynaud's disease, and the like; epilepsy; spastic paralysis; pollakiuria; cystitis; bladder detrusor hyperreflexia; urinary incontinence; dementia; AIDS related dementia; Alzheimer's diseases; Down's syndrome; Huntington's chorea; carcinoid syndrome; disorders related to immune enhancement or suppression; and the like.

It is furthermore expected that the object compound (I) and a pharmaceutically acceptable salt thereof of the present invention are useful for treating or preventing chronic obstructive pulmonary diseases, particularly chronic pulmonary emphysema; iritis; proliferative vitreoretinopathy; psoriasis; inflammatory intestinal diseases, particularly Crohn's diseases; hepatitis; superficial pain on congelation, burn, herpes zoster or diabetic neuropathy; tenalgia attended to hyperlipidemia; postoperative neuroma, particularly of mastectomy; vulvar vestibulitis; hemodialysis-associated itching; lichen planus; laryngopharyngitis; bronchiectasis; coniosis; whooping cough; pulmonary tuberculosis; cystic fibrosis; emesis; mental diseases, particularly anxiety, depression, dysthymic disorders and schizophrenia; demyelinating diseases such as multiple sclerosis and amyotrophic lateral sclerosis; attenuation of morphine withdrawal; oedema, such as oedema caused by thermal injury; small cell carcinomas, particularly small cell lung cancer (SCLC); hypersensitivity disorders such as poison ivy; fibrosing and collagen diseases such as scleroderma and eosinophilic fascioliasis; reflex sympathetic dystrophy such as shoulder/hand syndrome; addiction disorders such as alcoholism; stress related somatic disorders; rheumatic diseases such as fibrositis; and the like.

For therapeutic purpose, the compound (I) and a pharmaceutically acceptable salt thereof of the present invention can be used in a form of pharmaceutical preparation containing one of said compound, as an active ingredient, in admixture with a pharmaceutically acceptable carrier such as an organic or inorganic solid or liquid excipient suitable for oral, parenteral, external including topical, enteral, intravenous, intramuscular, inhalant, nasal, intraarticular, intraspinal, transtracheal or transocular administration. The pharmaceutical preparations may be solid, semi-solid or solutions such as capsules, tablets, pellets, dragees, powders, granules, suppositories, ointments, creams, lotions, inhalants, injections, cataplasms, gels, tapes, eye drops, solution, syrups, aerosols, suspension, emulsion, or the like. If desired, there may be included in these preparations, auxiliary substances, stabilizing agents, wetting or emulsifying agents, buffers and other commonly used additives.

While the dosage of the compound (I) will vary depending upon the age and condition of a patient, an average single dose of about 0.1 mg, 1 mg, 10 mg, 50 mg, 100 mg, 250 mg, 500 mg and 1000 mg of the compound (I) may be effective for treating Tachykinin-mediated diseases such as asthma and the like. In general, amounts between 0.1 mg/body and about 1,000 mg/body may be administered per day.

In order to illustrate the usefulness of the object compound (I) and a pharmaceutically acceptable salt thereof, the pharmacological test data of some representative compounds of the present invention is shown in the following.

All of the following Test Compounds showed more than 90% inhibition rate of $^3$H-Substance P binding to guinea pig lung membranes at the concentration of 1 μg/ml.

Test Compounds

The object compounds of the Examples 7-7, 17-1, 17-2, 17-4, 17-5, 17-10, 17-11, 17-24, 19-1, 19-4, 19-10, 24-4 and 24-8

$^3$H-Substance P Binding to Guinea Pig Lung Membranes

Test Method $^3$H-Substance P Binding to Guinea Pig Lung Membranes (a) Crude lung membrane preparation Male Hartly strain guinea pigs were stunned and bled. The trachea and lung were removed and homogenized in ice-cold buffer (0.25M sucrose, 50 mM Tris-HCl pH 7.5, 0.1 mM EDTA) by using Polytoron (Kinematica). The homogenate was centrifuged (1000×g, 10 minutes) to remove tissue clumps and the supernatant was centrifuges (35000×g, 20 minutes) to yield pellet. The pellet was resuspended in buffer (5 mM Tris-HCl pH 7.5), homogenized with a teflon homogenizer and centrifuged (35000×g, 20 minutes) to yield pellet which was referred to as crude membrane fractions. The obtained pellet was resuspended in buffer (50 mM Tris-HCl pH 7.5) and stored at −70° C. until use.

(b) ³H-Substance P binding to preparation membrane

Frozen crude membrane fractions were thawed and resuspended in Medium 1 (50 mM Tris-HCl pH 7.5, 1 mM $MnCl_2$, 0.02% BSA, 2 μg/ml chymostatin, 4 μg/ml leupeptin, 40 μg/ml bacitracin, 10 μM phosphoramidon). ³H-Substance P (1 nM) was incubated with 100 μl of the membrane preparations with or without test compounds in Medium 1 at 25° C. for 30 minutes in a final volume of 500 μl. At the end of the incubation period, 5 ml ice-cold 50 mM Tris-HCl buffer was added to each tube and its content was quickly filtered over a Wahtman GF/B glass filter (pretreated with 0.1% polyethylene imine for 3 hours prior to use) under aspiration. Each of the filters was then washed four times with 5 ml of ice-cold buffer (50 mM Tris-HCl pH 7.5). The radioactivity was counted in 5 ml of Aquazol-2 in Packerd scintillation counter (Packerd TRI-CARB 4530). All data presented are specific binding defined as that displaceable by 5 μM unlabeled Substance P.

All of the following Test Compounds showed more than 90% inhibition rate of ¹²⁵I-BH-Substance P binding to h-$NK_1$ receptors at the concentration of 0.1 μg/ml.

Test Compounds

The object compounds of the Examples 17-50, 17-56, 17-57, 17-60, 19-13, 21-3, 25-2, 26, 77, 79-4 and 79-6

¹²⁵I-BH-Substance P Binding to h-$NK_1$ Receptors Test Method

¹²⁵I-BH-Substance P Binding to h-$NK_1$ Receptors (a) Crude CHO cell membrane preparation CHO cells permanently expressing h-$NK_1$ receptors were harvested and homogenized with a Dounce homogenizer at 4° C. in a buffer (0.25M sucrose, 25 mM Tris-HCl pH 7.4, 10 mM $MgCl_2$, 1 mM EDTA, 5 μg/ml p-APMSF). The homogenate was centrifuged (500×g, 10 minutes), and the pellet was resuspended in the same buffer, homogenized, and centrifuged. The two supernatants were combined and centrifuged (100,000×g, 1 hour). The crude cell membranes thus isolated were resuspended in buffer (25 mM Tris-HCl pH 7.4, 10 mM $MgCl_2$, 1 mM EDTA, 5 μg/ml p-APMSF) and stored at −80° C. until use.

(b) ¹²⁵I-BH-Substance P binding to preparation membrane Cell membranes (6 μg/ml) were incubated with ¹²⁵I-BH-Substance P (0.1 nM) with or without test compounds in 0.25 ml of Medium 2(50 mM Tris-HCl pH 7.4, 5 mM $MnCl_2$, 20 μg/ml chymostatin, 40 μg/ml bacitracin, 4 μg/ml leupeptin, 5 μg/ml p-APMSF, 200 μg/ml BSA) at 22° C. for 90 minutes. At the end of the incubation period, the content was quickly filtered over a Wahtman GF/C glass filter (pretreated with 0.1% polyethylene imine for 3 hours prior to use) under aspiration. Each of the filters was then washed four times with 5 ml of buffer (50 mM Tris-HCl pH 7.4, 5 mM $MnCl_2$). The radioactivity was counted by using Auto Gamma counter (Packerd RIASTAR 5420A). All data presented are specific binding defined as that displaceable by 3 μM unlabeled Substance P.

The following Preparations and Examples are given for the purpose of illustrating this invention.

Preparation 1

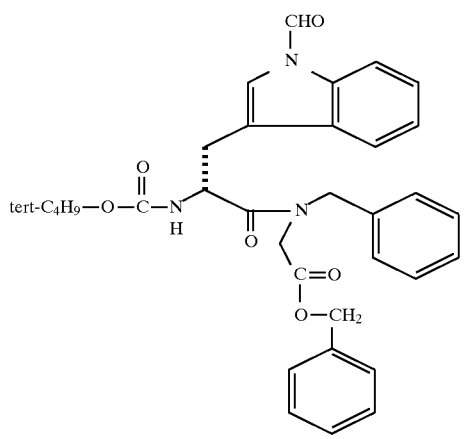

To a mixture of $N^2$-(tert-butoxycarbonyl)-$N^1$-formyl-D-tryptophan (3.99 g) and N-benzyl glycin benzyl ester hydrochloride (3.50 g) in dichloromethane (70 ml) was added triethylamine (5.85 ml) under nitrogen atmosphere. To the mixture was added 2-chloro-1-methylpyridinium iodide (3.67 g) at room temperature, and the resulting mixture was stirred for 2 hours. After the reaction was completed, dichloromethane (30 ml) and water (30 ml) were added. The organic layer was separated, washed with 0.5N hydrochloric acid (10 ml), water (10 ml), aqueous sodium bicarbonate solution (10 ml) and brine (20 ml) successively and dried over magnesium sulfate. After evaporation of the solvent, the residue was purified on a silica gel column (140 g) eluting with a mixture of toluene and ethyl acetate (4:1) to give (2R)-N-benzyl-N-benzyloxycarbonylmethyl-2-(tert-butoxycarbonylamino)-3-(N-formyl-1H-indol-3-yl) propanamide (6.41 g) as an oil.

IR ($CHCl_3$): 3300, 2970, 1740, 1700, 1644, 1604 $cm^{-1}$

NMR (DMSO-$d_6$, δ): 0.89, 1.22 and 1.29 (9H, 3 s); 2.80–3.10 (2H, m); 3.95–4.25 (2H, m); 4.40–4.90 (3H, m); 4.95–5.20 (2H, m); 7.05–7.75 (15H, m); 7.98 and 8.22 (1H, 2 br s); 9.22 and 9.61 (1H, 2 br s)

MASS: 570 (M+1)

Preparation 2

The following compounds were obtained according to a similar manner to that of Preparation 1.

1) (2R)-N-Benzyl-N-benzyloxycarbonylmethyl-2-(tert-butoxycarbonylamino)-3-(3,4-dimethylphenyl)-propanamide IR (Neat): 3300, 1740, 1700, 1645, 1500, 1360 $cm^{-1}$ NMR ($CDCl_3$, δ): 1.40 (9H, s); 2.2–2.3 (6H, m); 2.8–3.2 (2H, m); 3.7–4.2 (2H, m); 4.5–5.0 (3H, m); 5.1–5.2 (2H, m); 5.2–5.3 (1H, m); 6.9–7.1 (5H, m); 7.2–7.5 (8H, m)

MASS: 531 (M+1), 475, 431

2) (2S) -N-Benzyl-N-benzyloxycarbonylmethyl-2-(tert-butoxycarbonylamino)-3-(N-formyl-1H-indol-3-yl) propanamide IR (Neat): 3300, 1700, 1650, 1460 $cm^{-1}$

MASS: 570 (M+1), 514, 470

3) (2R)-N-Benzyl-N-benzyloxycarbonylmethyl-2-(tert-butoxycarbonylamino)-3-phenylpropanamide IR (Neat): 3300, 1750–1630, 1150, 1013, 725 $cm^{-1}$ NMR ($CDCl_3$, δ): 1.38 and 1.62 (9H, 2 br s); 2.87–3.16 (2H, m); 3.74–4.73 (5H, m); 4.94–5.28 (3H, m); 7.02–7.37 (15H, m)

4) (2R)-N-Benzyl-N-benzyloxycarbonylmethyl-2- (tert-butoxycarbonylamino)- 3-(3,4-dichlorophenyl)-propanamide mp: 171°–172° C.

IR (Nujol): 3250, 1730, 1680, 1645, 1520, 1360 cm$^{-1}$

NMR (DMSO-d$_6$, δ): 1.2–1.4 (9H, m); 2.7–3.0 (2H, m); 3.9–4.3 (2H, m); 4.4–4.8 (3H, m); 5.12 (2H, s); 7.0–7.5 (14H, m)

MASS: 571 (M+1), 515, 471, 363

5) (2R)-N-Benzyl-N-benzyloxycarbonylmethyl-2-(tert-butoxycarbonylamino)-3-(benzo[b]thiophen-3-yl)propanamide IR (Neat): 3400, 3300, 1725, 1700, 1640, 1490, 1440, 1380, 1360 cm$^{-1}$ NMR (CDCl$_3$, δ): 1.1–1.4 (9H, m); 3.2–3.5 (2H, m); 3.6–4.8 (4H, m); 4.8–5.4 (4H, m); 6.8–7.1 (2H, m); 7.1–7.4 (11H, m); 7.7–8.0 (2H, m)

MASS: 559 (M+1), 503, 459, 351

6) (2S)-N-Benzyl-N-benzyloxycarbonylmethyl-2-(tert-butoxycarbonylamino)-3-(3,4-dimethylphenyl)-propanamide IR (Neat): 3300, 2960, 2920, 1742, 1700, 1646 cm$^{-1}$ NMR (CDCl$_3$, δ): 1.40 (9H, s); 2.18, 2.21 and 2.22 (6H, 3 s); 2.78–3.14 (2H, m); 3.73–4.15 (2H, m); 4.44–5.35 (5H, m); 6.85–7.40 (14H, m)

MASS: 531 (M+1)

7) (2R, 3R)-N-Benzyl-N-benzyloxycarbonylmethyl-2-(tert-butoxycarbonylamino)-3-(N-methyl-1H-indol-3-yl)-butanamide IR (Neat): 3400, 3300, 1740, 1700, 1640, 1480, 1450, 1360 cm$^{-1}$ NMR (CDCl$_3$, δ): 1.3–1.5 (9H, m); 3.6–5.4 (15H, m); 7.0–7.8 (15H, m)

MASS: 570 (M+1), 538, 514, 471

Preparation 3

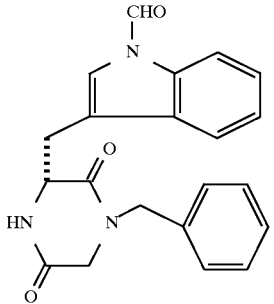

To an ice-cooled solution of the object compound of Preparation 1 (6.39 g) in dichloromethane (50 ml) was added 4N hydrogen chloride in dioxane solution (50 ml). The mixture was stirred at the same temperature for 30 minutes and at room temperature for 1 hour. After evaporation of the solvent, the residue was partitioned between dichloromethane (50 ml) and aqueous sodium bicarbonate solution (30 ml). The organic layer was separated, dried over magnesium sulfate and filtered. To the filtrate was added triethylamine (1.67 ml) at room temperature, and the mixture was stirred for 1.5 hours. After evaporation, the residue was triturated with diisopropyl ether, collected by filtration and dried to give (3R)-1-benzyl-3-(N-formyl-1H-indol-3-yl-methyl)piperazine-2,5-dione (3.93 g).

mp: 176°–178° C.

IR (Nujol): 3250, 1709, 1648, 1630 cm$^{-1}$

NMR (DMSO-d$_6$, δ): 2.95–3.30 and 3.35–3.70 (4H, 2 m); 4.22 (1H, d, J=14.6 Hz); 4.30–4.40 (1H, m); 4.54 (1H, d, J=14.9 Hz); 6.80–7.75 (9H, m); 7.95–8.50 (2H, m); 9.20 and 9.65 (1H, 2 br s)

MASS: 362 (M+1)

Preparation 4

The following compounds were obtained according to a similar manner to that of Preparation 3.

1) (3R)-1-Benzyl-3-(3,4-dimethylbenzyl)piperazine-2,5-dione mp: 191°–192° C. [α]$_D$$^{25}$: −23.3° (C=1, DMF)

IR (Nujol): 3180, 1640, 1500, 1340 cm$^{-1}$

NMR (DMSO-d$_6$, δ) 2.11 and 2.16 (3H, 2 s); 2.82(1H, dd, J=4.8 and 13.5 Hz); 3.13 (1H, dd, J=4.2 and 13.5 Hz); 2.76 (1H, d, J=17.1 Hz); 3.46 (1H, d, J=17.1 Hz); 4.22 (1H, d, J=14.5 Hz); 4.55 (1H, d, J=14.5 Hz); 4.2–4.3 (1H, m); 6.7–6.9 (3H, m); 7.0–7.1 (2H, m); 7.2–7.3 (3H, m); 8.31 (1H, s)

MASS: 323 (M+1)

2) (3S)-1-Benzyl-3-(N-formyl-1H-indol-3-yl-methyl)-piperazine-2,5-dione mp: 183°–184° C.

IR (Nujol): 3250, 1710, 1650 cm$^{-1}$

NMR (DMSO-d$_6$, δ): 3.0–4.6 (7H, m); 6.9–8.5 (10H, m); 8.4 (1H, s); 9.2 (1H, s); 10.9 (1H, s)

MASS: 362 (M+1)

3) (3R)-1-Benzyl-3-benzylpiperazine-2,5-dione mp: 180°–181° C.

IR (Nujol): 3240, 1675–1630, 1315, 1205, 1183, 1101, 1058, 740, 700 cm$^{-1}$

NMR (CDCl$_3$, δ): 2.92–3.56 (4H, m); 4.34–4.40 (1H, m); 4.48 (2H, s); 6.66 (1H, s); 7.13–7.36 (10H, m)

4) (3R)-1-Benzyl-3-(3,4-dichlorobenzyl)piperazine-2,5-dione mp: 167°–168° C.

[α]$_D$$^{25}$: −12.8° (C=1.0, DMF)

IR (Nujol): 3250, 1670, 1645, 1440, 1320 cm$^{-1}$

NMR (DMSO-d$_6$, δ): 2.94 (1H, dd, J=4.8 and 13.4 Hz); 3.18 (1H, dd, J=4.8 and 13.4 Hz); 3.19 (1H, d, J=17.4 Hz); 3.67 (1H, d, J=17.4 Hz); 4.19 (1H, d, J=14.6 Hz); 4.3–4.4 (1H, m); 4.72 (1H, d, J=14.6 Hz); 7.0–7.2 (3H, m); 7.3–7.4 (3H, m)); 7.4–7.5 (2H, m); 8.35–8.45 (1H, m)

MASS: 363 (M+1)

5) (3R)-1-Benzyl-3-(benzo [b]thiophen-3-yl-methyl)-piperazine-2,5-dione mp: 213°–215° C.

[α]$_D$$^{25}$: +73.5° (C=1.0, DMF)

IR (Nujol): 3250, 1675, 1645, 1430, 1340, 1315 cm$^{-1}$

NMR (DMSO-d$_6$, δ): 2.94 (1H, d, J=17.3 Hz); 3.21 (1H, dd, J=4.5 and 14.5 Hz); 3.43 (1H, dd, J=4.5 and 14.5 Hz); 3.46 (1H, d, J=17.3 Hz); 4.23 (1H, d, J=14.5 Hz); 4.38 (1H, d, J=14.5 Hz); 4.3–4.4 (1H, m); 6.9–7.1 (2H, m); 7.2–7.5 (6H, m); 7.8–8.1 (2H, m); 8.41 (1H, s)

MASS: 351 (M+1)

6) (3S)-1-Benzyl-3 -(3,4-dimethylbenzyl)piperazine-2,5-dione mp: 188°–189° C.

[α]$_D$$^{21}$: +22.7° (C=1.0, DMF)

IR (Nujol): 3200, 1653 cm$^{-1}$

NMR (DMSO-d$_6$, δ): 2.11 (3H, s); 2.16 (3H, s);
2.77 (1H, d, J=17.0 Hz); 2.83 (1H, dd, J=13.5, 4.8 Hz); 3.07 (1H, dd, J=13.5, 4.2 Hz); 3.45 (1H, d, J=17.2 Hz); 4.22 (1H, m); 4.23 (1H, d, J=14.4 Hz); 4.55 (1H, d, J=14.6 Hz); 6.74–6.95 (3H, m); 7.04–7.38 (5H, m); 8.30 (1H, s)

MASS: 323 (M+1)

7) (3R)-1-Benzyl-3-[(1R)-1-(N-methyl-1H-indol-3-yl) ethyl]piperazine-2,5-dione mp: >240° C.

[α]$_D$$^{25}$: +4.6° (C=1.0, DMF)

IR (Nujol): 3250, 1670, 1650, 1330, 1310 cm$^{-1}$

NMR (DMSO-d$_6$, δ): 1.39 (3H, d, J=7.4 Hz); 2.22 (1H, d, J=17.2 Hz); 3.09 (1H, d, J=17.2 Hz); 3.67 (3H, s); 3.7–3.8 (1H, m); 3.78 (1H, d, J=14.8 Hz); 4.0–4.1 (1H, m); 4.28 (1H, d, J=14.8 Hz); 6.7–6.9 (2H, m); 7.0–7.2 (6H, m); 7.40 (1H, d, J=8.1 Hz); 7.52 (1H, d, J=7.9 Hz); 8.60 (1H, d, J=1.0 Hz)

MASS: 362 (M+1), 339

Preparation 5

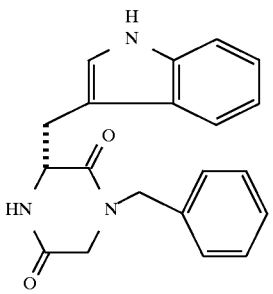

To an ice-cooled solution of the object compound of Preparation 3 (3.89 g) in a mixture of methanol (175 ml) and tetrahydrofuran (50 ml) was added aqueous 0.1N sodium hydroxide solution (108 ml). The mixture was stirred at the same temperature for 30 minutes and at room temperature for 1.5 hours. After evaporation of the solvent, the residue was extracted with dichloromethane. The organic layer was washed with water and an aqueous sodium chloride solution, and dried over magnesium sulfate. Evaporation of the solvent gave (3R)-1-benzyl-3-(1H-indol-3-yl-methyl)piperazine-2,5-dione (3.68 g).

mp: 207°–208° C.

IR (Nujol): 3402, 1650 cm$^{-1}$

NMR (DMSO-d$_6$, δ): 2.68 (1H, d, J=17.2 Hz); 3.04 (1H, dd, J=14.4 and 4.4 Hz); 3.20–3.40 (2H, m); 4.24 (1H, s); 4.10–4.40 (2H, m); 6.75–7.60 (10H, m); 8.35 (1H, s); 10.94 (1H, s)

MASS: 334 (M+1)

Preparation 6

The following compounds were obtained according to a similar manner to that of Preparation 5.

1) (3S)-1-Benzyl-3-(1H-indol-3-yl-methyl)piperazine-2,5-dione mp: 210°–211° C.

[α]$_D^{25}$: +48.1° (C=1.0, DMF)

IR (Nujol): 3400, 3225, 1650, 1455 cm$^{-1}$

NMR (DMSO-d$_6$, δ): 3.0–3.4 (3H, m); 4.2 (4H, s); 6.8–7.6 (10H, m); 8.4 (1H, s)

MASS: 334 (M+1)

2) (3R, 6R)-1-Benzyl-3-(1H-indol-3-yl-methyl)-6-methyl-piperazine-2,5-dione

[α]$_D^{19}$: +5.9° (C=1.0, MeOH)

IR (Neat): 3250, 1675, 1635, 1450, 1320 cm$^{-1}$

NMR (DMSO-d$_6$, δ): 0.35 (3H, d, J=7 Hz); 3.00–4.86 (6H, m); 6.95–8.32 (11H, m); 10.94 (1H, s)

MASS: 348 (M+1)

3) (3R, 6S)-1-Benzyl-3-(1H-indol-3-yl-methyl)-6-piperazine-2,5-dione

IR (Neat): 3260, 1670, 1450, 1320 cm$^{-1}$

MASS: 348 (M+1)

Preparation 7

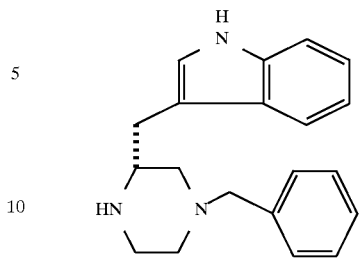

To a suspension of lithium aluminum hydride (0.77 g) in tetrahydrofuran (40 ml) was added dropwise a solution of the object compound of Preparation 5 (3.40 g) in tetrahydrofuran (40 ml) at 0° C. under nitrogen atmosphere. The mixture was stirred at room temperature for 50 minutes and at refluxing temperature for 1 hour. The resulting mixture was diluted with tetrahydrofuran (60 ml) and cooled to 0° C. Water (3.0 ml) and aqueous 15% sodium hydroxide solution (0.8 ml) were added slowly. The resulting insoluble inorganic material was removed by filtration and washed with tetrahydrofuran. The filtrate and the washing were combined and evaporated under reduced pressure to give (3R)-1-benzyl-3-(1H-indol-3-yl-methyl)piperazine (3.68 g) as an oil.

IR (CHCl$_3$): 3240, 3040, 2900 cm$^{-1}$

NMR (DMSO-d$_6$, δ): 1.70–2.00 and 2.30–2.45 (2H, 2 m); 2.50–3.00 (7H, m); 3.25–3.60 (3H, m); 6.80–7.60 (10H, m); 10.80 (1H, s)

MASS: 306 (M+1)

Preparation 8

The following compounds were obtained according to a similar manner to that of Preparation 7.

1) (3R)-1-Benzyl-3-(3,4-dimethylbenzyl) piperazine

IR (Neat): 3000–2750, 1670, 1500, 1450, 1360, 1320 cm$^{-1}$

NMR (CDCl$_3$, δ): 2.26 (6H, m); 1.8–3.0 (9H, m); 3.4–3.6 (2H, m); 6.9–7.1 (3H, m); 7.2–7.5 (5H, m)

MASS: 295 (M+1)

2) (3R)-1,3-Dibenzylpiperazine

IR (Neat): 3020, 2850, 2800, 1600, 1493, 1453, 1322, 1134, 1027, 735, 697 cm$^{-1}$ NMR (CDCl$_3$, δ): 1.68–2.15 (4H, m); 2.48–3.00 (6H, m); 3.43–3.58 (2H, m); 7.18–7.33 (10H, m)

3) (3S)-1-Benzyl-3-(1H-indol-3-yl-methyl)piperazine

[α]$_D^{25}$: +13.0° (C=1.0, DMF)

IR (Neat): 3400, 3150, 3025, 1450 cm$^{-1}$

NMR (DMSO-d$_6$, δ): 1.7–3.4 (9H, m); 6.9–7.5 (10H, m); 10.8 (1H, s)

MASS: 306 (M+1)

4) (3R)-1-Benzyl-3-(3,4-dichlorobenzyl)piperazine

IR (Neat): 3200 (br), 3100–2700, 1660, 1590, 1550, 1490, 1460, 1450, 1400, 1320 cm$^{-1}$ NMR (CDCl$_3$, δ): 1.8–2.2 (3H, m); 2–4–3.0 (7H, m); 3.4–3.6 (2H, m); 7.02 (1H, dd, J=2.0 and 8.2 Hz); 7.2–7.4 (7H, m)

MASS: 335 (M+1)

5) (3R)-1-Benzyl-3-(benzo[b]thiophen-3-yl-methyl)-piperazine

IR (Neat): 2600–3100, 1660, 1490, 1450, 1425 cm$^{-1}$

NMR (CDCl$_3$, δ): 1.8–2.2 (4H, m) ; 2.7–3.3 (6H, m ); 3.4–3.6 (2H, m); 7.1–7.5 (8H, m); 7.7–8.0 (2H, m)

MASS: 323 (M+1)

6) (3S)-1-Benzyl-3-(3,4-dimethylbenzyl)piperazine

IR (Neat): 3310–3250, 3020, 2930, 2800, 1668 cm$^{-1}$

NMR (CDCl$_3$, δ): 1.70 (1H, br s); 1.80–3.60 (11H, m); 2.23 (6H, s); 6.83–7.40 (8H, m)

MASS: 295 (M+1)

7) (3R)-1-Benzyl-3-[(1R)-1-(N-methyl-1H-indol-3-yl)-ethyl]piperazine 8) (3R,6R)-1-Benzyl-3-(1H-indol-3-yl-methyl)-6-methyl-piperazine

[α]$_D^{19}$: −21.2° (C=1.0, MeOH)

IR (Neat): 3400, 3200, 1650, 1450 cm$^{-1}$

NMR (DMSO-d$_6$, δ): 1.02 (3H, d, J=7 Hz); 2.25–4.10 (10H, m), 6.91–7.51 (11H, m); 10.74 (1H, d, J=14 Hz)

MASS: 320 (M+1)

9) (3R, 6S)-1-Benzyl-3-(1H-indol-3-yl-methyl)-6-methyl-piperazine

[α]$_D^{19}$: +30.0° (C=1.0, MeOH)

IR (Neat): 3400, 3125, 1450, 1330 cm$^{-1}$

NMR (DMSO-d$_6$, δ): 1.02 (3H, d, J=7 Hz); 2.10–4.10 (10H, m); 6.91–7.47 (10H, m); 10.76 (1H, s)

MASS: 320 (M+1)

10) (2S)-1-Benzyl-2-(2-naphthylmethyl)piperazine

[α]$_D^{19}$: +0.9° (C=1.0, CHCl$_3$)

IR (Neat): 2600–3100, 1650, 1600 cm$^{-1}$

NMR (CDCl$_3$, δ): 2.2–4.3 (10H, m); 3.48 (1H, d, J=13.5 Hz); 4.16 (1H, d, J=13.5 Hz); 7.0–7.9 (12H, m)

MASS: 317 (M+1)

11) (3S)-3-Benzyl-1-(3-phenylpropyl)piperazine

[α]$_D^{20}$: +12.35° (C=1.075, MeOH)

IR (Neat): 3230, 3020, 2940, 2800 cm$^{-1}$

NMR (DMSO-d$_6$, δ): 1.50–1.95 (4H, m); 2.19 (2H, t, J=7.2 Hz); 2.55–3.45 (10H, m); 7.00–7.20 (10H, m)

MASS: 295 (M+1)

Preparation 9

A solution of N-(tert-butoxycarbonyl)-D-alanine (3 g) in dimethylformamide (5 ml) was added dropwise to a stirred solution mixture of 60% sodium hydride (1.4 g) in dimethylformamide (5 ml) at ice-bath temperature. After stirring for 30 minutes at the same temperature, benzyl bromide (4.14 ml) was added and then the mixture was stirred for 1 hour at the same temperature and then for 6 hours at room temperature. The reaction mixture was poured into a mixture of dilute hydrochloric acid and ice-water, and extracted with diisopropyl ether. The extract was washed with aqueous sodium bicarbonate solution and brine successively and dried over magnesium sulfate. After evaporation of the solvent in vacuo, the residue was purified by column chromatography on silica gel eluting with a mixture of n-hexane and ethyl acetate (2:1) to give an oily product, which was dissolved in dichloromethane (40 ml). To the solution was added 4N hydrogen chloride in dioxane solution (7 ml) at ice-bath temperature. The resulting mixture was stirred for 1.5 hours at room temperature and then concentrated under reduced pressure to give benzyl (2R)-2-(N-benzylamino) propionate hydrochloride (2.2 g).

[α]$_D^{19}$: +6.6° (C=1.0, MeOH)

IR (Nujol): 2700, 2600, 2500, 2375, 1740, 1460 cm$^{-1}$

NMR (DMSO-d$_6$, δ): 1.55 (3H, d, J=7 Hz); 4.1–4.28 (3H, m); 5.25 (2H, s); 7.4–7.56 (10H, m); 9.8 (1H, br s); 10.25 (1H, br s)

MASS: 270 (M+1) (free)

Preparation 10

The following compound was obtained according to a similar manner to that of Preparation 9.

Benzyl (2S)-(N-benzylamino)propionate hydrochloride

IR (Neat): 3300, 1730, 1450, 1175, 1150 cm$^{-1}$

NMR (CDCl$_3$, δ): 1.33 (3H, d, J=7 Hz); 3.43 (1H, q, J=7 Hz); 3.72 (2H, q, J=14 Hz); 5.17 (2H, s); 7.2–7.36 (10H, m)

MASS: 270 (M+1) (free)

Preparation 11

1) N,N-Diisopropylethylamine (8.26 ml) was added to a stirred mixture of N-(tert-butoxycarbonyl)-L-naphthylalanine (10.0 g) and benzyl bromide (4.52 ml) in dimethylformamide (100 ml) at 5° C. The mixture was stirred for 4.5 hours at room temperature and then poured into ice-water (500 ml). The desired product was extracted with ethyl ether and the extract was washed successively with dilute hydrochloric acid, aqueous sodium bicarbonate solution and brine, and dried over magnesium sulfate. After evaporation of the solvent, the residue was triturated with diisopropyl ether to give benzyl (2S)-2-[N-(tert-butoxycarbonyl) amino]-3-(2-naphthyl)propionate (13.4 g).

mp: 90°–91° C.

IR (Nujol) 3380, 1735, 1690, 1520, 1320 cm$^{-1}$

2) A solution of benzyl (2S)-2-[N-(tert-butoxycarbonyl) amino]-3-(2-naphthyl)propionate (5.0 g) in dimethylformamide (50 ml) was added dropwise to a stirred mixture of 60% sodium hydride (0.6 g) and dimethylformamide (50 ml) at ice-bath temperature. After the addition was completed, the reaction mixture was stirred at the same temperature for 30 minutes. Benzyl bromide (1.76 ml) was added and then the whole mixture was stirred for 3.5 hours. Additional benzyl bromide (0.4 ml) was added and then stirred for 2.5 hours. The reaction mixture was poured into ice-water and extracted with ethyl acetate. The extract was washed successively with 1N hydrochloric acid, aqueous sodium bicarbonate solution and brine and dried over magnesium sulfate. After evaporation of the solvent in vacuo, the residue was purified by column chromatography on silica gel eluting with a mixture of n-hexane and ethyl acetate (4:1) to give benzyl (2S)-2-[N-(tert-butoxycarbonyl)-N-benzylamino]-3-(2-naphthyl)propionate (3.53 g).

IR (Neat): 3100–2800, 1740, 1690, 1600 cm$^{-1}$

NMR (CDCl$_3$, δ): 1.1–1.5 (9H, m); 3.2–4.6 (5H, m); 4.9–5.1 (2H, m); 6.9–7.9 (17H, m)

Preparation 12

To a mixture of N$^2$-(tert-butoxycarbonyl)-N$^1$-formyl-D-tryptophan (2.17 g) and benzyl (2R)-2-(N-benzylamino) propionate hydrochloride (2.0 g) in dichloromethane (30 ml) was added triethylamine (2.3 ml) under nitrogen atmosphere. To the mixture was added 2-chloro-1-methylpyridinium iodide (1.84 g) at room temperature, and the resulting mixture was stirred for 2 hours and left overnight. The reaction mixture was washed successively with dilute hydrochloric acid, aqueous sodium bicarbonate solution and brine, and dried over magnesium sulfate. After evaporation of the solvent, the residue was dissolved in dichloromethane (30 ml). A solution of 4N hydrogen chloride in dioxane solution (10 ml) was added thereto at ice-bath temperature and-then the resulting mixture was stirred for 1 hour at room temperature. The reaction mixture was concentrated under reduced pressure. The residue was partitioned between dichloromethane and aqueous saturated sodium bicarbonate solution. The organic layer was separated, washed with brine, dried over magnesium sulfate and filtered. To the filtrate was added triethylamine (1 ml) and the resulting mixture was stirred for 1 hour at room temperature. The reaction mixture was concentrated under reduced pressure. The residue was purified on a silica gel column (60 g) eluting with a mixture of n-hexane and ethyl acetate (2:1) to give (3R,6R)-1-benzyl-3-(N-formyl-1H-indol-3-yl-methyl)-6-methylpiperazine-2,5-dione (1.3 g).

IR (Neat): 3200, 1700, 1675, 1650, 1460 cm$^{-1}$

NMR (DMSO-d$_6$, δ): 0.64 (3H, d, J=7 Hz); 3.09–4.83 (6H, m); 7.1–8.4 (10H, m)

MASS: 376 (M+1)

Preparation 13

The following compound was obtained according to a similar manner to that of Preparation 12.

(3R, 6S)-1-Benzyl-3-(N-formyl-1H-indol-3-yl-methyl)-6-methylpiperazine-2,5-dione IR (Neat): 3200, 1675, 1450, 1370, 1320 cm$^{-1}$
NMR (DMSO-d$_6$, δ): 1.26 (3H, d, J=7 Hz); 3.08–3.44 (3H, m); 3.94–4.04 (1H, m); 4.52–4.64 (1H, m); 4.97–5.10 (1H, m); 6.83–7.81 (10H, m); 8.37 (1H, s)
MASS: 376 (M+1)

Preparation 14

Benzyl (2S)-2-[N-(tert-butoxycarbonyl)-N-benzylamino]-3-(2-naphthyl)propionate (10.5 g) was dissolved in methanol (100 ml) and aqueous 1N sodium hydroxide solution (20 ml) was added at ice-bath temperature. The mixture was stirred at room temperature overnight. The reaction mixture was poured into ice-water and extracted with diisopropyl ether. The aqueous layer was adjusted to pH 3 by adding dilute hydrochloric acid and extracted with ethyl acetate. The extract was washed with brine and dried over magnesium sulfate. Evaporation of the solvent gave N-benzyl-N-(tert-butoxycarbonyl)-3-(2-naphthyl)-L-alanine (3.0 g).

NMR (CDCl$_3$, δ): 1.4–1.6 (9H, m); 3.2–4.6 (5H, m); 5.6–6.4 (1H, br s); 6.7–7.8 (12H, m)
MASS: 404 (M-1)

Preparation 15

To a stirred mixture of N-benzyl-N-(tert-butoxycarbonyl)-3-(2-naphthyl)-L-alanine (2.9 g), glycine methyl ester hydrochloride (0.9 g) and 1-hydroxybenzotriazole hydrate (1.06 g) in dichloromethane (50 ml) was added dropwise 1-(3-dimethylaminopropyl)-3-ethylcarbodiimide (1.43 ml) at ice-bath temperature. The resulting mixture was stirred at room temperature for 2 days and then evaporated under reduced pressure. The residue was partitioned between ethyl acetate and aqueous sodium bicarbonate solution. The organic layer was separated, washed with dilute hydrochloric acid and brine, and dried over magnesium sulfate. Evaporation of the solvent gave (2S)-2-[N-benzyl-N-(tert-butoxycarbonyl)amino]-N-methoxycarbonylmethyl-3-(2-naphthyl)propanamide.

IR (Neat): 3350, 3100–2800, 1750, 1680, 1660, 1600, 1530 cm$^{-1}$
NMR (CDCl$_3$, δ): 1.3–1.5 (9H, m); 3.2–4.7 (8H, m); 3.69 (3H, s); 6.8–7.9 (12H, m)
MASS: 477 (M+1), 421, 337

Preparation 16

To a stirred solution of the object compound of Preparation 15 (3.1 g) in dichloromethane (30 ml) was added dropwise 4N hydrogen chloride in dioxane solution (30 ml) at ice-bath temperature. The resulting mixture was stirred at room temperature for 1 hour and then evaporated under reduced pressure to give an oil, which was partitioned between ethyl acetate and aqueous sodium bicarbonate solution. The ethyl acetate layer was washed with brine and dried over magnesium sulfate. Evaporation of the solvent in vacuo gave a syrup, which was dissolved in a mixture of acetic acid (25 ml) and toluene (25 ml). The resulting mixture was heated at reflux temperature for 3 hours and concentrated under reduced pressure. The residue was triturated with a mixed solvent of water and diisopropyl ether to afford (2S)-1-benzyl-2-(2-naphthylmethyl)piperazine-3,6-dione (1.6 g).

mp 160°–161° C.
[α]$_D$$^{19}$: +0.7° (C=1.0, MeOH)
IR (Nujol): 3250, 1670, 1650, 1430, 1350 cm$^{-1}$
NMR (DMSO-d$_6$, δ): 2.5–2.6 (2H, m); 3.1–3.5 (2H, m); 4.03 (1H, t, J=4.8 Hz); 4.11 (1H, d, J=15.1); 5.16 (1H, d, J=15.1 Hz); 7.2–8.0 (12H, m); 8.09 (1H, br s)
MASS: 345 (M+1)

Preparation 17

A solution of di-tert-butyl dicarbonate (218 mg) in acetone (2 ml) was added dropwise to a stirred mixture of (3R)-1-benzyl-3-(1H-indol-3-yl-methyl)piperazine (305 mg) and triethylamine (150 mg) in a mixed solvent of acetone (3 ml) and water (3 ml) at ice-bath temperature. The resulting mixture was stirred at room temperature for 1 hour and evaporated under reduced pressure. The residue was partitioned between ethyl acetate and water. The organic layer was separated, washed successively with dilute hydrochloric acid, aqueous sodium bicarbonate solution and brine, and dried over magnesium sulfate. After evaporation of the solvent in vacuo, the residue was dissolved in ethanol (10 ml) and then treated with ammonium formate (315 mg) in the presence of 10% Pd charcoal at 90° C. under nitrogen atmosphere. After stirring for 30 minutes, the reaction mixture was filtered and concentrated under reduced pressure to give (2R)-1-(tert-butoxycarbonyl)-2-(1H-indol-3-yl-methyl)piperazine (310 mg).

IR (Neat): 3300, 1660, 1410 cm$^{-1}$
NMR (DMSO-d$_6$, δ) 1.1 (9H, s); 2.4–4.4 (9H, m); 6.9–7.6 (5H, m); 10.8 (1H, s)
MASS: 316 (M+1)

Preparation 18

To a stirred mixture of (2R)-1-(tert-butoxycarbonyl)-2-(1H-indol-3-yl-methyl)piperazine (250 mg) and potassium carbonate (165 mg) in dimethylformamide (1 ml) was added trans-cinnamoyl chloride (150 mg) at room temperature. The resulting mixture was stirred for 3 hours and then poured into water. Extraction with ethyl acetate followed by drying over magnesium sulfate and evaporation in vacuo gave a syrup, which was dissolved in dichloromethane (2 ml). A solution of 4N hydrogen chloride in dioxane solution (1 ml) was added to the solution at ice-bath temperature and the resulting mixture was stirred for 1 hour at room temperature. The reaction mixture was concentrated under reduced pressure. The residue was partitioned between ethyl acetate and aqueous saturated sodium bicarbonate solution. The organic layer was separated, washed with brine and dried over magnesium sulfate. Evaporation of the solvent in vacuo gave (3R)-1-(transcinnamoyl)-3-(1H-indol-3-yl-methyl)piperazine (166 mg).

[α]$_D$$^{26}$: -37.5° (C=1.0, MeOH)
IR (Neat) 3250, 1640, 1590, 1435 cm$^{-1}$
NMR (DMSO-d$_6$, δ): 2.3–4.4 (9H, m); 6.9–7.7 (13H, m); 10.9 (1H, s)
MASS: 346 (M+1) (to be continued on the next page)

Example 1

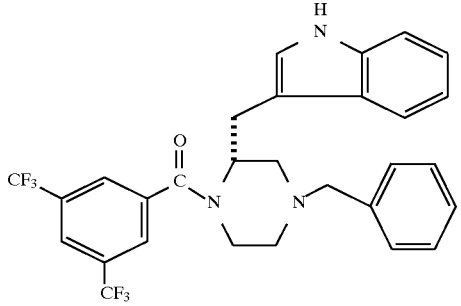

To a mixture of 3,5-bis(trifluoromethyl)benzoic acid (1.15 g) and (3R)-1-benzyl-3-(1H-indol-3-yl-methyl)piperazine (1.61 g) in dichloromethane (80 ml) was added triethylamine (1.55 ml) at room temperature under nitrogen atmosphere. 2-Chloro-1-methylpyridinium iodide (1.37 g) was added, and the mixture was stirred at room temperature for 2.5 hours. The resulting mixture was poured into water (20 ml). The organic layer was washed successively with 0.5N hydrochloric acid, water, aqueous sodium bicarbonate solution and brine, and dried over magnesium sulfate. After evaporation under reduced pressure, the residue was chromatographed on silica gel with toluene—ethyl acetate (4:1) as an eluent to give (2R)-4-benzyl-1-[3,5-bis(trifluoromethyl)benzoyl]-2-(1H-indol-3-yl-methyl)piperazine (0.87 g) as a syrup.

IR (CHCl$_3$): 3430, 3300, 3000, 2910, 2800, 1630–1610 cm$^{-1}$

NMR (DMSO-d$_6$, δ): 1.90–2.40 (2H, m); 2.70–3.90 (8H, m); 4.25–4.40 and 4.75–4.90 (1H, m); 6.50–7.45 (10H, m); 7.50–8.25 (3H, m); 10.77 (1H, s)

MASS: 546 (M+1)

Example 2

The following compounds were obtained according to a similar manner to that of Example 1.

1) (2R)-4-Benzyl-1-[3,5-bis(trifluoromethyl)benzoyl]-2-(3,4-dimethylbenzyl)piperazine IR (Neat): 3000–2700, 1640, 1500, 1430, 1350 cm$^{-1}$ NMR (CDCl$_3$, δ): 2.1–2.3 (6H, m); 2.1–2.2 (2H, m); 2.6–3.7 (8H, m); 4.5–5.1 (1H, m); 6.5–6.7 (2H, m); 6.9–7.6 (7H, m); 7.8–7.9 (2H, m)

MASS: 535 (M+1)

2) (2R)-4-Benzyl-1-(3,5-dimethylbenzoyl)-2-(1H-indol-3-yl-methyl)piperazine

IR (Nujol): 3200, 1600 cm$^{-1}$

NMR (DMSO-d$_6$, δ) 1.95–4.40 (9H, m); 2.17 (6H, s); 6.6–7.7 (13H, m); 10.74 (1H, s)

MASS: 438 (M+1)

Example 3

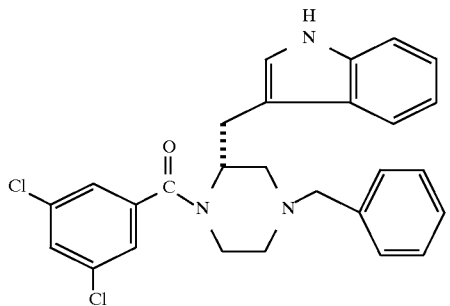

To an ice-cooled mixture of (3R)-1-benzyl-3-(1H-indol-3-yl-methyl)piperazine (305 mg) and potassium carbonate (207 mg) in dimethylformamide (1 ml) was added 3,5-dichlorobenzoyl chloride (210 mg). The mixture was stirred at room temperature for 1 hour. Ethyl acetate and water were added. The organic layer was washed successively with aqueous sodium bicarbonate solution and brine and dried over magnesium sulfate. After evaporation of the solvent, the residue was dissolved in ethyl ether. After insoluble material was removed by filtration, the filtrate was concentrated under reduced pressure and the residue was triturated with diisopropyl ether, collected by filtration and dried to give (2R)-4-benzyl-1-(3,5-dichlorobenzoyl)-2-(1H-indol-3-yl-methyl)piperazine.

mp: 93°–98° C.

IR (Nujol): 3225, 1600 cm$^{-1}$

NMR (DMSO-d$_6$, δ): 1.9–4.8 (9H, m); 6.7–7.8 (13H, m); 10.79 (1H, s)

MASS: 478 (M+1)

Example 4

The following compounds were obtained according to a similar manner to that of Example 3.

1) (2R)-4-Benzyl-1-benzoyl-2-(1H-indol-3-yl-methyl)-piperazine mp: 165°–167° C.

IR (Nujol): 3200, 1600, 1440, 1425 cm$^{-1}$

NMR (DMSO-d$_6$, δ): 1.9–4.8 (9H, m); 6.5–7.7 (15H, m); 10.7 (1H, s)

MASS: 410 (M+1)

2) (2R)-4-Benzyl-1-benzenesulfonyl-2-(1H-indol-3-yl-methyl)piperazine mp: 120°–123° C.

IR (Nujol): 3560, 3450, 3225, 1310, 1160 cm$^{-1}$

NMR (DMSO-d$_6$, δ): 1.6–1.9 (2H, m); 2.5–2.8 (2H, m); 3.16–4.03 (5H, m); 6.72–7.83 (15H, m); 10.76 (1H, s)

MASS: 446 (M+1)

3) (2R)-2,4-Dibenzyl-1-[3,5-bis(trifluoromethyl)-benzoyl]piperazine $[\alpha]_D^{28}$: −13.0° (C=1.0, MeOH)

IR (Neat): 3020, 2930, 2800, 1635, 1430, 1270, 1125, 900, 740 cm$^{-1}$

NMR (DMSO-d$_6$, δ): 1.99–2.30 (2H, m); 2.60–3.70 (8H, m); 4.30–4.90 (1H, m); 6.80–8.17 (13H, m)

MASS: 507 (M+1)

4) (2S)-4-Benzyl-1-[3,5-bis(trifluoromethyl)benzoyl]-2-(1H-indol-3-yl-methyl)piperazine IR (Neat): 3275, 1625, 1430 cm$^{-1}$ NMR (DMSO-d$_6$, δ): 1.9–4.8 (11H, m); 6.6–8.4 (13H, m); 10.8 (1H, m)

MASS: 546 (M+1)

5) (2R)-4-Benzyl-1-[2,5-bis(trifluoromethyl)benzoyl]-2-(1H-indol-3-yl-methyl)piperazine mp 186°–187° C.

IR (Nujol): 3200, 1625, 1330, 1310 cm$^{-1}$

NMR (DMSO-d$_6$, δ): 1.8–4.9 (11H, m); 6.6–8.2 (13H, m); 10.7–10.9 (1H, m)

MASS: 546 (M+1)

6) (2R)-4-Benzyl-1-[2,4-bis(trifluoromethyl)benzoyl]-2-(1H-indol-3-yl-methyl)piperazine IR (Neat) 3250, 1620, 1340 cm$^{-1}$ NMR (DMSO-d$_6$, δ) 2.6–4.9 (11H, m); 6.6–8.3 (13H, m); 10.8–10.9 (1H, m)

MASS: 546 (M+1)

7) (2R)-4-Benzyl-1-(3-phenoxybenzoyl)-2-(1H-indol-3-yl-methyl)piperazine mp: 165°–167° C.

IR (Nujol) 3200, 1600, 1450 cm$^{-1}$

NMR (DMSO-d$_6$, δ): 1.9–4.8 (11H, m); 6.7–7.8 (19H, m); 10.7 (1H, s)

MASS: 502 (M+1)

8) (2R)-4-Benzyl-1-[2,6-bis(trifluoromethyl)benzoyl]-2-(1H-indol-3-yl-methyl)piperazine IR (Neat): 3300, 1640, 1590, 1430 cm$^{-1}$ NMR (DMSO-d$_6$, δ) 1.7–3.6 (11H, m); 6.8–8.4 (13H, m); 10.8 (1H, s)

MASS: 546 (M+1)

Example 5

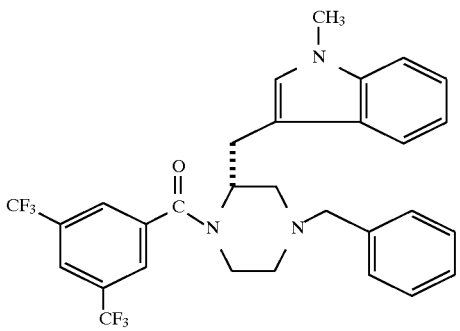

To an ice-cooled solution of (2R)-4-benzyl-1-[3,5-bis(trifluoromethyl)benzoyl]-2-(1H-indol-3-yl-methyl)piperazine (1.15 g) in dimethylformamide (60 ml) was added 60% sodium hydride (0.1 g) under nitrogen atmosphere, and the mixture was stirred for 5 minutes. After addition of methyl iodide (0.13 ml), the reaction mixture was stirred for 40 minutes. The reaction was quenched with 0.5N hydrochloric acid (60 ml) and diluted with dichloromethane (80 ml). The organic layer was washed with water, aqueous sodium bicarbonate solution and brine, and dried over magnesium sulfate. After removal of the solvent, the residue was purified on a silica gel column eluting with a mixture of toluene and ethyl acetate (10:1) to give (2R)-4-benzyl-1-[3,5-bis(trifluoromethyl)benzoyl]-2-(N-methyl-1H-indol-3-yl-methyl)piperazine (1.12 g) as a syrup.

IR (CHCl$_3$): 3010, 2930, 2800, 2760, 1635 cm$^{-1}$

NMR (DMSO-d$_6$, δ): 1.88–2.35 (2H, m); 2.59–3.15 (4H, m); 3.15–3.48 (2H, m); 3.58 and 3.64 (3H, 2 s); 3.48–3.80 (2H, m); 4.28–4.44 and 4.67–4.85 (1H, 2 m); 6.50–7.48 (10H, m); 7.20, 7.99, 8.06 and 8.20 (3H, 4 m)

MASS: 560 (M+1)

Example 6

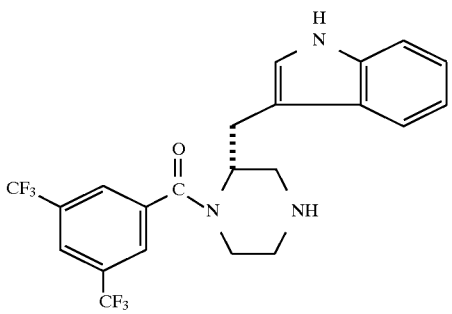

A mixture of (2R)-4-benzyl-1-[3,5-bis(trifluoro-methyl)benzoyl]-2-(1H-indol-3-yl-methyl)piperazine (5.20 g), ammonium formate (1.50 g) and 10% Pd charcoal (0.52 g) in ethanol (50 ml) was refluxed for 7.5 hours under nitrogen atmosphere. The reaction mixture was cooled to room temperature and filtered through Celite pad. The filtrate was concentrated under reduced pressure and the residue was purified on a silica gel column eluting with a mixture of dichloromethane and methanol (20:1) to give (2R)-1-[3,5-bis(trifluoromethyl)benzoyl]-2-(1H-indol-3-yl-methyl)piperazine (2.67 g, 61.5%) as a syrup.

IR (CHCl$_3$): 3280, 2900, 1622 cm$^{-1}$

NMR (DMSO-d$_6$, δ): 2.50–3.50 (9H, m); 3.6–4.8 (1H, m); 6.55–7.40 (5H, m); 7.50–8.22 (3H, m); 10.84 (1H, s)

MASS: 456 (M+1)

Example 7

The following compounds were obtained according to a similar manner to that of Example 6.

1) (2R)-1-[3,5-Bis(trifluoromethyl)benzoyl]-2-(3,4-dimethylbenzyl)piperazine

IR (Neat): 3320, 3050–2750, 1630, 1500, 1430, 1350, 1320 cm$^{-1}$

NMR (CDCl$_3$, δ) 2.24 (6H, s); 2.2–2.3 (2H, m); 2.6–3.8 (9H, m); 4.4–5.2 (1H, m); 6.6–7.9 (6H, m)

MASS: 445 (M+1)

2) (2R)-1-[3,5-Bis(trifluoromethyl)benzoyl]-2-(N-methyl-1H-indol-3-yl-methyl)piperazine IR (CHCl$_3$): 3320, 2940, 2830, 1628 cm$^{-1}$ NMR (DMSO-d$_6$, δ): 2.50–3.59 (9H, m); 3.69, 3.70 (3H, s); 4.15–4.35, 4.65–4.84 (1H, m); 6.64–8.22 (8H, m)

MASS: 470 (M+1)

3) (2R)-1-Benzoyl-2-(1H-indol-3-yl-methyl)piperazine mp: 211°–213° C.

[α]$_D^{25}$: +51.4° (C=1.0, MeOH)

IR (Nujol): 3200, 1600, 1590 cm$^{-1}$

NMR (DMSO-d$_6$, δ) 2.5–4.7 (9H, m); 6.6–7.9 (10H, m); 10.8 (1H, s)

MASS: 320 (M+1)

4) (2R)-1-Benzenesulfonyl-2-(1H-indol-3-yl-methyl)-piperazine mp: 152–154° c

[α]$_D^{25}$: −1.70 (C=1.0, MeOH)

IR (Nujol): 3350, 1290, 1150 cm$^{-1}$

NMR (DMSO-d$_6$, δ): 2.25–3.60 (8H, m); 3.95–4.0 (1H, m); 6.96–7.84 (10H, m); 10.86 (1H, s)

MASS: 355 (M+1)

5) (2R)-1-(3,5-Dimethylbenzoyl)-2-(1H-indol-3-yl-methyl)piperazine

[α]$_D^{25}$: +44.4° (C=1.0, MeOH)

IR (Neat): 3225, 1600, 1430, 1330 cm$^{-1}$

NMR (DMSO-d$_6$, δ): 2.18 (6H, s); 2.5–4.8 (9H, m); 6.55–7.34 (8H, m); 10.85 (1H, s)

MASS: 348 (M+1)

6) (2R)-1-(3,5-Dichlorobenzoyl)-2-(1H-indol-3-yl-methyl)piperazine

[α]$_D^{25}$: +34.7° (C=1.0, MeOH)

IR (Nujol): 3200, 1620, 1610 cm$^{-1}$

NMR (DMSO-d$_6$, δ) 2.9–4.5 (9H, m); 6.7–7.5 (9H, m); 10.96 (1H, s)

MASS: 388 (M+1), 354, 320

7) (2R)-2-Benzoyl-1-[3,5-bis(trifluoromethyl)benzoyl]-piperazine

[α]$_D^{28}$: −17.6° (C=1.0, MeOH)

IR (Neat): 3320, 2750, 1620, 1430, 1270, 1120, 900 cm$^{-1}$

NMR (DMSO-d$_6$, δ): 2.50–3.50 (9H, m); 4.19–4.90 (1H, m); 6.80–7.00 (1H, m); 7.15–7.40 (5H, m); 7.63 (1H, s); 8.10 (1H, m)

MASS: 417 (M+1)

8) (2S)-1-[3,5-Bis(trifluoromethyl)benzoyl]-2-(1H-indol-3-yl-methyl)piperazine

IR (Neat): 3250, 1625, 1430 cm$^{-1}$

NMR (DMSO-d$_6$, δ): 2.6–4.9 (9H, m); 6.6–8.2 (8H, m); 8.4 (1H, s); 10.9 (1H, s)

MASS: 456 (M+1)

Example 8

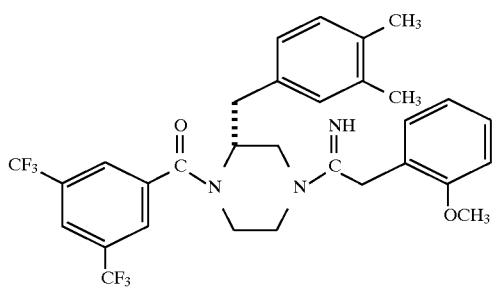

To a stirred mixture of (2R)-1-[3,5-bis(trifluoromethyl)benzoyl]-2-(3,4-dimethylbenzyl)piperazine (0.1 g) and triethylamine (0.125 ml) in dimethylformamide (0.6 ml) was added ethyl 2-methoxybenzenecarboximidate hydrochloride (62 mg) at room temperature. The resulting mixture was heated at 100° C. for 1 hour. The mixture was poured into ice-water, and extracted by ethyl acetate. The extract was purified on a silica gel column (dichloromethane/methanol) and treatment with 4N hydrogen chloride in ethyl acetate solution gave (2R)-1-[3,5-bis(trifluoromethyl)benzoyl]-2-(3,4-dimethylbenzyl)-4-[1-imino-2-(2-methoxyphenyl)ethyl]piperazine hydrochloride.

mp: 237°–238° C.

$[\alpha]_D^{25}$: −16.2° (C=0.88, MeOH)

IR (Nujol): 3400–3200, 1680, 1620, 1490, 1330, 1270 cm$^{-1}$

NMR (DMSO-d$_6$, δ): 2.1–2.2 (6H, m); 2.6–4.5 (14H, m); 6.4–6.6 (1H, m); 6.9–7.5 (8H, m); 8.1–8.2 (1H, m); 9.3–9.6 (1H, m); 9.8–9.1 (1H, m)

MASS: 592 (M+1) (free), 445

Example 9

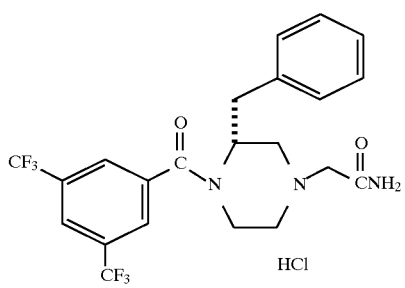

(2R)-2-Benzyl-1-[3,5-bis(trifluoromethyl)benzoyl]-4-(methoxycarbonylmethyl)piperazine (0.2 g) was treated with 20% ammonia methanol solution (5 ml), and the resulting mixture was left overnight in a refrigerator. The reaction mixture was concentrated under reduced pressure and the residue was purified on a silica gel column (7 g) eluting with a mixture of dichloromethane and methanol (10:1) to give (2R)-2-benzyl-1-[3,5-bis(trifluoromethyl)benzoyl]-4-(carbamoylmethyl)-piperazine. This compound was treated with 4N hydrogen chloride in ethyl acetate solution to give the corresponding hydrochloride (0.18 g) as a white powder.

mp: 166°–169° C.

$[\alpha]_D^{26}$: −6.4° (C=1.0, MeOH)

IR (Nujol): 3600–3050, 2700–2000, 1685, 1635, 1275, 1128, 900 cm$^{-1}$

NMR (DMSO-d$_6$, δ): 2.70–5.15 (13H, m); 6.90–7.00 (1H, m); 7.10–7.50 (5H, m); 7.65–7.85 (1H, m); 8.10–8.25 (1H, m)

MASS: 474 (M+1) (free), 417

Example 10

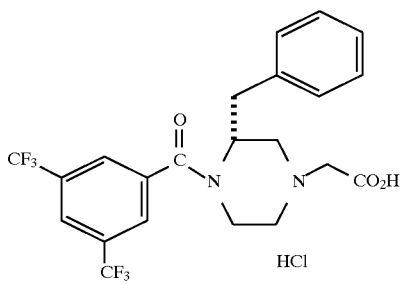

To a solution of (2R)-2-benzyl-1-[3,5-bis(trifluoromethyl)benzoyl]-4-(methoxycarbonylmethyl)-piperazine (0.18 g) in methanol (18 ml) was added aqueous 1N sodium hydroxide solution (4.3 ml), and the mixture was stirred at room temperature for 50 minutes. The reaction mixture was evaporated under reduced pressure and the residue was diluted with water (4 ml). 1N Hydrochloric acid (4.3 ml) was added to the solution at 0° C. and the resulting precipitate was collected by filtration and washed with water. The obtained carboxylic acid was converted to the corresponding hydrochloride by treatment with 4N hydrogen chloride in ethyl acetate solution to give (2R)-2-benzyl-1-[3,5-bis(trifluoromethyl)benzoyl]-4-(carboxymethyl)piperazine hydrochloride (0.12 g).

mp: 158°–161° C.

$[\alpha]_d^{25}$: −11.5° (C=1.0, MeOH)

IR (Nujol): 3650–3100, 2700–2100, 1730, 1630, 1276, 1130, 903 cm$^{-1}$

NMR (DMSO-d$_6$, δ): 2.70–5.15 (11H, m); 6.90–8.25 (8H, m)

MASS: 475 (M+1) (free), 417

Example 11

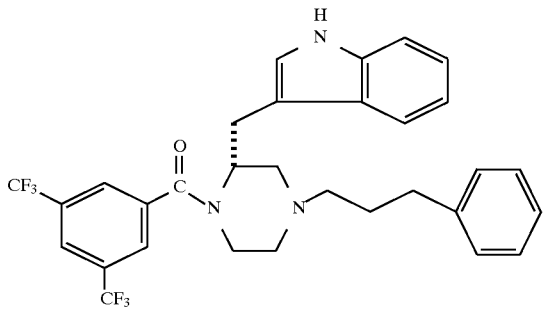

A mixture of (2R)-1-[3,5-bis(trifluoromethyl)-benzoyl]-2-(1H-indol-3-yl-methyl)piperazine (0.17 g), 1-bromo-3-phenylpropane (0.08 g) and potassium carbonate (0.15 g) in dry dimethylformamide (10 ml) was stirred at room temperature under nitrogen atmosphere. After 2 hours, additional 1-bromo-3-phenylpropane (0.14 ml) and potassium carbonate (0.15 g) were added, and the mixture was stirred overnight. Water (50 ml) and dichloromethane (50 ml) were added to the mixture. The dichloromethane layer was washed with brine and dried over magnesium sulfate. After evaporation of the solvent, the residue was purified on a silica gel column (10 g) eluting with a mixture of toluene and ethyl acetate (4:1) to give (2R)-1-[3,5-bis (trifluoromethyl)benzoyl]-2-(1H-indol-3-yl-methyl)-4-(3-phenylpropyl)piperazine (0.17 g) as a syrup.

IR (CHCl$_3$): 3300, 2930, 1686, 1630 cm$^{-1}$

NMR (DMSO-d$_6$, δ): 1.62–2.44 (6H, m); 2.67 (2H, t); 2.80–3.30 (5H, m); 3.75–4.40, 4.80–4.95 (2H, m); 6.53–7.35 (10H, m); 7.40–8.20 (3H, m); 10.85 (1H, s)

MASS: 574 (M+1)

Example 12

The following compounds were obtained according to a similar manner to that of Example 11.

1) (2R)-1-[3,5-Bis(trifluoromethyl)benzoyl)-2-(3,4-dimethylbenzyl)-4-(3-phenylpropyl)piperazine IR (Neat): 3000–2750 (bra), 1630, 1500, 1440, 1350 cm$^{-1}$ NMR (CDCl$_3$, δ): 1.82 (2H, sext, J=7.4 Hz); 2.35 (2H, t, J=7.4 Hz); 2.71 (2H, t, J=7.4 Hz); 2.1–2.2 (6H, m); 2.1–2.5 (2H, m); 2.7–3.7 (6H, m); 4.5–5.2 (1H, m); 6.6–7.5 (10H, m); 7.28 (1H, s)

MASS: 563 (M+)

2) (2R)-2-Benzyl-1-[3,5-bis(trifluoromethyl)benzoyl]-4-(trans-cinnamyl)piperazine hydrochloride mp: 187°–190° C.

[α]$_D^{27}$: +0.4° (C=1.0, MeOH)

IR (Nujol): 3700–3100, 2700–2000, 1650, 1278, 1185, 1120, 900 cm$^{-1}$

NMR (DMSO-d$_6$, δ): 2.85–5.20 (13H, m); 6.45–6.65 (1H, m); 6.80–7.05 (2H, m); 7.15–8.30 (10H, m)

MASS: 533 (M+1) (free)

3) (2R)-2-Benzyl-1-[3,5-bis(trifluoromethyl)benzoyl]-4-(5-phenylpentyl)piperazine hydrochloride mp: 80°–88° C.

[α]$_D^{26}$: +0.4° (C=1.0, MeOH)

IR (Nujol): 3350, 2700–2100, 1635, 1275, 1170, 1125, 900 cm$^{-1}$

NMR (DMSO-d$_6$, δ): 1.30–1.40 (2H, m); 1.50–1.90 (4H, m); 2.50–2.70 (2H, m); 2.80–4.10 (10H, m); 4.50–5.20 (1H, m); 6.90–7.00 (1H, m); 7.10–7.50 (10H, m); 7.70 (1H, s); 8.17–8.22 (1H, m); 10.80–11.20 (2H, m)

MASS: 563 (M+1) (free)

4) (2R)-2-Benzyl-1-[3,5-bis(trifluoromethyl)benzoyl]-4-(4-phenylbutyl)piperazine hydrochloride mp: 88°–91° C.

[α]$_D^{26}$: +2.9° (C=1.0, MeOH)

IR (Nujol): 3600–3100, 2700–2000, 1635, 1275, 1170, 1130, 900 cm$^{-1}$

NMR (DMSO-d$_6$, δ): 1.50–1.90 (4H, m); 2.50–2.70 (2H, m); 2.70–4.10 (10H, m); 4.70–5.20 (1H, m); 6.90–7.00 (1H, m); 7.20–7.50 (10H, m); 7.72 (1H, s); 8.15–8.22 (1H, m); 10.90–11.25 (1H, m)

MASS: 549 (M+1) (free)

5) (2R)-2-Benzyl-1-[3,5-bis(trifluoromethyl)benzoyl]-4-methylpiperazine hydrochloride

[α]$_D^{26}$: -2.6° (C=1.0, MeOH)

IR (Nujol): 3370, 2750–2100, 1635, 1278, 1178, 1130, 900 cm$^{-1}$

NMR (DMSO-d$_6$, δ): 2.82 (3H, s); 2.80–4.10 (8H, m); 4.50–5.20 (1H, m); 6.95–6.98 (1H, m); 7.20–7.60 (5H, m); 7.66 (1H, s); 8.17–8.22 (1H, m); 11.00–11.40 (1H, m)

MASS: 431 (M+1) (free)

6) (2R)-2-Benzyl-1-[3,5-bis(trifluoromethyl)benzoyl]-4-ethylpiperazine hydrochloride mp: >220° C.

[α]$_D^{26}$: -1.2° (C=1.0, MeOH)

IR (Nujol): 3400, 2600, 1615, 1273, 1185, 1140, 904 cm$^{-1}$

NMR (DMSO-d$_6$, δ): 1.34 (3H, t, J=7.4 Hz); 2.80–4.15 (11H, m); 4.50–5.20 (1H, m); 6.90–7.00 (1H, m); 7.20–7.45 (5H, m); 7.72 (1H, s); 8.17–8.23 (1H, m); 10.90–11.40 (1H, m)

MASS: 445 (M+1) (free)

7) (2R)-2-Benzyl-1-[3,5-bis(trifluoromethyl)benzoyl]-4-isopropylpiperazine hydrochloride mp: 218°–221° C.

[α]$_D^{26}$: +1.1° (C=1.0, MeOH)

IR (Nujol): 3530, 3390, 2700–2300, 1640, 1272, 1134, 904 cm$^{-1}$

NMR (DMSO-d$_6$, δ): 1.26–1.40 (6H, m); 2.80–4.10 (9H, m); 4.50–5.20 (1H, m); 6.90–7.00 (1H, m); 7.20–7.60 (5H, m); 7.81 (1H, m); 8.17–8.23 (1H, m)

MASS: 459 (M+1) (free)

8) (2R)-2-Benzyl-1-[3,5-bis(trifluoromethyl)benzoyl]-4-(diphenylmethyl)piperazine hydrochloride mp: 118°–120° C.

[α]$_D^{26}$: +40.3° (C=1.0, MeOH)

IR (Nujol): 3500–3100, 2700–2100, 1640, 1277, 1175, 1133, 900 cm$^{-1}$

NMR (DMSO-d$_6$, δ): 2.60–5.69 (10H, m); 6.90–8.30 (18H, m); 12.10 (1H, br s)

MASS: 583 (M+1) (free), 417, 167

9) (2R)-2-Benzyl-1-[3,5-bis(trifluoromethyl)benzoyl]-4-[2-(1H-indol-3-yl)ethyl]piperazine hydrochloride mp: 155° C. (dec.)

[α]$_D^{26}$: -3.0° (C=1.0, MeOH)

IR (Nujol): 3700–3100, 2800–2100, 1635, 1276, 1170, 1130 cm$^{-1}$

NMR (DMSO-d$_6$, δ): 2.73–4.15 (12H, m); 4.75–5.25 (1H, m); 7.01–8.24 (13H, m); 11.00 (1H, s); 11.30 (1H, br s)

MASS: 560 (M+1) (free), 417

10) (2R)-2-Benzyl-1-[3,5-bis(trifluoromethyl)benzoyl]-4-(4-phenoxybutyl)piperazine hydrochloride mp: 153°–156° C.

[α]$_D^{26}$: +0.5° (C=1.0, MeOH)

IR (Nujol): 3600–3100, 2700–2000, 1640, 1280, 1122, 903 cm$^{-1}$

NMR (DMSO-d$_6$, δ): 1.70–2.15 (4H, m); 2.80–4.15 (12H, m); 4.55–5.20 (1H, m); 6.94–8.23 (13H, m)

MASS: 565 (M+1) (free)

11) (2R)-2-Benzyl-1-[3,5-bis(trifluoromethyl)benzoyl]-4-(3-phenoxypropyl)piperazine hydrochloride mp: 84°–87° C.

[α]$_D^{26}$: -0.2° (C=1.0, MeOH)

IR (Nujol): 3600–3100, 2700–2000, 1635, 1275, 1130, 900 cm$^{-1}$

NMR (DMSO-d$_6$, δ): 2.20–2.40 (2H, m); 2.80–4.20 (12H, m); 4.50–5.20 (1H, m); 6.90–7.70 (12H, m); 8.17–8.23 (1H, m); 11.00–11.30 (1H, m)

MASS: 551 (M+1) (free)

12) (2R)-2-Benzyl-1-[3,5-bis(trifluoromethyl)benzoyl]-4-(2-phenoxyethyl)piperazine hydrochloride mp: 145°–148° C.

[α]$_D^{26}$: -6.4° (C=1.0, MeOH)

IR (Nujol): 3700–3100, 2750–2000, 1635, 1275, 1125, 900 cm$^{-1}$

NMR (DMSO-d$_6$, δ): 2.85–5.20 (13H, m); 6.97–7.74 (12H, m); 8.18–8.23 (1H, m)

MASS: 537 (M+1) (free)

13) (2R)-2-Benzyl-1-[3,5-bis(trifluoromethyl)benzoyl]-4-[3-(1H-indol-3-yl)propyl]piperazine hydrochloride mp: 163° C. (dec.)

[α]$_D^{27}$: +1.4° (C=1.0, MeOH)

IR (Nujol): 3600–3100, 2700–2000, 1634, 1275, 1130, 900 cm$^{-1}$

NMR (DMSO-d$_6$, δ): 2.10–2.35 (2H, m); 2.70–5.20 (13H, m); 6.90–7.80 (12H, m); 8.15–8.22 (1H, m); 10.80–11.30 (2H, m)

MASS: 574 (M+1) (free), 417

14) (2R)-2-Benzyl-1-[3,5-bis(trifluoromethyl)benzoyl]-4-[(4-fluoro-2-methoxybenzoyl)methyl]piperazine hydrochloride mp: 176°–180° C.

[α]$_D^{24}$: +5.5° (C=1.0, MeOH)

IR (Nujol): 3600–3100, 2800–2100, 1650, 1605, 1280, 1130, 900 cm$^{-1}$

NMR (DMSO-d$_6$, δ): 2.73–5.20 (14H, m); 6.94–8.30 (11H, m)

MASS: 583 (M+1) (free), 417

15) (2R)-1-[3,5-Bis(trifluoromethyl)benzoyl]-4-methyl-2-(N-methyl-1H-indol-3-yl-methyl)piperazine IR (CHCl$_3$): 2930, 2830, 2780, 1683 cm$^{-1}$ NMR (DMSO-d$_6$, δ): 1.78–2.44 (2H, m); 2.24 (3H, s); 2.64–3.97 (6H, m); 3.69 and 3.72 (3H, 2 s); 4.17–4.96 (1H, m); 6.64–8.30 (8H, m)

MASS: 484 (M+1)

Example 13

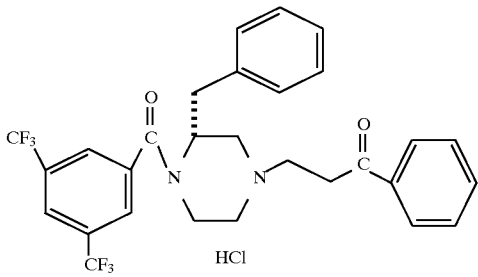

To an ice-cooled mixture of (2R)-2-benzyl-1-[3,5-bis(trifluoromethyl)benzoyl]piperazine (0.3 g) and potassium carbonate (0.20 g) in dimethylformamide (3 ml) was added a solution of 3-chloro-1-phenyl-1-propane (0.18 g) in dimethylformamide (1 ml) under nitrogen atmosphere. The resulting mixture was stirred at the same temperature for 1.5 hours and then at room temperature for 30 minutes. The mixture was poured into a mixture of water and ethyl acetate. The organic layer was separated, washed with brine and evaporated. The residue was purified by chromatography on a silica gel (toluene/ethyl acetate=30:1) to afford object compound, which was converted to the corresponding hydrochloride, (2R)-2-benzyl-1-[3,5-bis(trifluoromethyl)benzoyl]-4-(2-benzoylethyl)piperazine hydrochloride, by treatment with 4N hydrogen chloride in ethyl acetate solution.

mp: 218°–220° C.

[α]$_D^{26}$: +7.2° (C=1.0, DMF)

IR (Nujol): 2400, 1680, 1640, 1277, 1122, 900 cm$^{-1}$

NMR (DMSO-d$_6$, δ): 2.80–4.20 (12H, m); 4.50–5.20 (1H, m); 6.90–7.00 (1H, m); 7.10–7.45 (5H, m); 7.50–7.80 (4H, m); 8.00–8.10 (2H, m); 8.10–8.25 (1H, m); 10.55–11.10 (1H, m)

MASS: 549 (M+1) (free), 417

Example 14

To an ice-cooled mixture of (2R)-2-benzyl-1-[3,5-bis(trifluoromethyl)benzoyl]piperazine (0.3 g) and triethylamine (0.39 ml) in dimethylformamide (8 ml) was added 3-(chloromethyl)pyridine hydrochloride (0.12 g). The reaction mixture was stirred at the same temperature for 30 minutes and then at room temperature for 2 hours. Additional triethylamine (0.39 ml) and 3-(chloromethyl)pyridine hydrochloride (0.12 g) were added and the resulting mixture was stirred overnight. The reaction mixture was filtered and the filtrate was concentrated and subjected to a chromatography on a silica gel eluting with a mixture of toluene and ethyl acetate (5:1). The eluent was treated with 4N hydrogen chloride in ethyl acetate solution to give (2R)-2-benzyl-1-[3,5-bis(trifluoromethyl)benzoyl]-4-(pyridin-3-yl-methyl)piperazine dihydrochloride.

mp: 164°–168° C.

[α]$_D^{25}$: +9.1° (C=1.0, MeOH)

IR (Nujol): 3700–3100, 2700–2000, 1630, 1270, 1120, 900 cm$^{-1}$

NMR (DMSO-d$_6$, δ): 2.80–5.40 (11H, m); 6.85–6.90 (1H, m); 7.10–7.40 (4H, m); 7.46 (1H, s); 7.75 (1H, s); 7.90–8.00 (1H, m); 8.19–8.23 (1H, m); 8.66–8.70 (1H, m); 8.88–8.91 (1H, m); 9.09 (1H, s)

MASS: 508 (M+1) (free)

Example 15

The following compounds were obtained according to a similar manner to that of Example 14.

1) (2R)-2-Benzyl-1-[3,5-bis(trifluoromethyl)benzoyl]-4-(methoxycarbonylmethyl)piperazine IR (Neat): 3700–3300, 2940, 1740, 1637, 1430, 1270, 1120, 900 cm$^{-1}$ NMR (DMSO-d$_6$, δ): 2.30–5.00 (14H, m); 6.90–7.00 (1H, m); 7.10–7.70 (6H, m); 8.10–8.20 (1H, m)

MASS: 489 (M+1), 417

2) (2R)-1-[3,5-Bis(trifluoromethyl)benzoyl]-2-(1H-indol-3-yl-methyl)-4-(methoxycarbonylmethyl)piperazine

[α]$_D^{24}$: −8.3° (C=1.0, MeOH)

IR (Neat): 3300, 1737, 1628, 1276, 1130, 900, 737 cm$^{-1}$

NMR (DMSO-d$_6$, δ): 2.30–5.00 (14H, m); 6.60–8.20 (8H, m); 10.87 (1H, s)

MASS: 528 (M+1)

3) (2R)-1-[3,5-Bis(trifluoromethyl)benzoyl]-2-(3,4-dimethylbenzyl)-4-(methoxycarbonylmethyl)piperazine IR (Neat): 3000–2700, 1745, 1645, 1500, 1430, 1380, 1350, 1330 cm$^{-1}$ NMR (CDCl$_3$, δ): 2.1–2.3 (6H, m), 2.4–3.8 (10H, m); 3.74 (3H, s); 4.5–5.2 (1H, m); 6.6–7.5 (5H, m); 7.8–7.9 (1H, m)

MASS: 517 (M+1), 445

Example 16

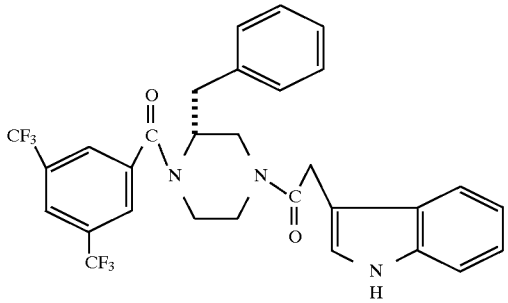

To a stirred mixture of (2R)-2-benzyl-1-[3,5-bis(trifluoromethyl)benzoyl]piperazine (0.3 g) and 2-(1H-indol-3-yl)acetic acid (0.13 g) in dichloromethane (8 ml) containing triethylamine (0.25 ml) was added 2-chloro-1- methylpyridinium iodide (0.22 g) at room temperature under nitrogen atmosphere. After being stirred for 5 hours, the reaction mixture was diluted with dichloromethane and washed with 0.1N hydrochloric acid, aqueous saturated sodium bicarbonate solution and brine, and dried over magnesium sulfate. After removal of the solvent, the residue was purified by column chromatography on silica gel using chloroform-methanol (50:1) as eluent to give (2R)-2-benzyl-1-[3,5-bis(trifluoromethyl)benzoyl]-4-[2-(1H-indol-3-yl) acetyl]piperazine (0.34 g) as a white powder.

mp: 201°–210° C.

$[\alpha]_D^{27}$: +27.6° (C=1.0, MeOH)

IR (Nujol): 3270, 1630, 1276, 1115, 900, 737 cm$^{-1}$

NMR (DMSO-d$_6$, δ): 2.60–5.00 (11H, m); 6.70–7.70 (12H, m); 8.10–8.20 (1H, m); 10.85–11.10 (1H, m)

MASS: 574 (M+1), 417

Example 17

The following compounds were obtained according to a similar manner to that of Example 16.

1) (2R)-1-[3,5-Bis(trifluoromethyl)benzoyl]-2-(1H-indol-3-yl-methyl)-4-(trans-cinnamoyl)piperazine mp: 118°–119° C.

$[\alpha]_D^{25}$: −34.7° (C=1.0, MeOH)

IR (Nujol): 3550–3100, 1635, 1275, 1130, 900 cm$^{-1}$

NMR (DMSO-d$_6$, δ): 2.80–5.20 (11H, m); 6.50–8.20 (14H m)

MASS: 586 (M+1), 452

2) (2R)-1-[3,5-Bis(trifluoromethyl)benzoyl]-2-(1H-indol-3-yl-methyl)-4-(4-fluoro-trans-cinnamoyl)piperazine mp: 116°–120° C.

$[\alpha]_D^{26}$: −31.5° (C=1.0, MeOH)

IR (Nujol): 3500–3100, 1635, 1595, 1277, 1130, 900 cm$^{-1}$

NMR (DMSO-d$_6$, δ): 2.80–5.15 (10H, m); 6.50–8.30 (12H, m); 10.80–10.95 (1H, m)

MASS: 604 (M+1)

3) (2R)-1-[3,5-Bis(trifluromethyl)benzoyl]-2-(1H-indol-3-yl-methyl)-4-[2-(N,N-dimethylamino)acetyl]-piperazine IR (Nujol): 3200, 1655, 1635 cm$^{-1}$ NMR (DMSO-d$_6$, δ): 2.10–2.50 (6H, m); 2.74–4.65 and 4.80–5.15 (11H, 2 m), 6.54–7.55 (5H, m); 7.60–8.30 (3H, m); 10.92 (1H, s)

MASS: 541 (M+1)

4) (2R)-2-Benzyl-1-[3,5-bis(trifluoromethyl)benzoyl]-4-(3-phenylpropionyl)piperazine $[\alpha]_D^{25}$: +14.1° (C=1.0, MeOH)

IR (Neat): 3700–3300, 3000, 2800, 1630, 1420, 1270, 1120, 900, 695 cm$^{-1}$

NMR (DMSO-d$_6$, δ): 2.50–5.10 (13H, m); 6.85–6.95 (1H, m); 7.10–7.45 (10H, m); 7.59–7.68 (1H, m); 8.12–8.18 (1H, m)

MASS: 549 (M+1), 417

5) (2R)-2-Benzyl-1-[3,5-bis(trifluoromethyl)benzoyl]-4-(4-phenylbutyryl)piperazine $[\alpha]_D^{27}$: +13.3° (C=1.0, MeOH)

IR (Neat): 3700–3300, 3010, 2920, 1640, 1420, 1270, 1122, 900, 695 cm$^{-1}$

NMR (DMSO-d$_6$, δ): 1.80–1.95 (2H, m); 2.60–4.50 (13H, m); 6.90–7.80 (12H, m); 8.10–8.20 (1H, m)

MASS: 563 (M+1), 417

6) (2R)-2-Benzyl-1-[3,5-bis(trifluoromethyl)benzoyl]-4-(5-phenylvaleryl)piperazine $[\alpha]_D^{27}$: +13.1° (C=1.0, MeOH)

IR (Neat): 3700–3300, 3010, 2820, 1635, 1425, 1275, 1125, 900, 695 cm$^{-1}$

NMR (DMSO-d$_6$, δ): 1.50–1.70 (4H, m); 2.60–4.50 (13H, m); 6.90–7.80 (12H, m); 8.10–8.20 (1H, m)

MASS: 577 (M+1), 417

7) (2R)-2-Benzyl-1-[3,5-bis(trifluoromethyl)benzoyl]-4-(trans-cinnamoyl)piperazine mp: 144°–145° C.

$[\alpha]_D^{28}$: +13.90° (C=1.0, MeOH)

IR (Nujol): 3700–3100, 1634, 1607, 1281, 1184, 1128, 905 cm$^{-1}$

NMR (DMSO-d$_6$, δ): 2.60–5.10 (11H, m); 6.80–7.80 (12H, m); 8.14–8.20 (1H, m)

MASS: 547 (M+1), 417

8) (2R)-2-Benzyl-1-[3,5-bis(trifluoromethyl)benzoyl]-4-[2-(4-fluorophenyl)acetyl]piperazine $[\alpha]_D^{27}$: +14.9° (C=1.0, MeOH)

IR (Neat): 3700–3300, 3020, 2900, 1630, 1508, 1425, 1270, 1125, 900 cm$^{-1}$

NMR (DMSO-d$_6$, δ): 2.60–5.10 (11H, m); 6.85–7.00 (1H, m); 7.10–7.75 (10H, m); 8.10–8.22 (1H, m)

MASS: 553 (M+1), 417

9) (2R)-2-Benzyl-1-[3,5-bis(trifluoromethyl)benzoyl]-4-[(1H-indol-3-yl)carbonyl]piperazine mp: 130°–131° C.

$[\alpha]_D^{28}$: +31.8° C. (C=1.0, MeOH)

IR (Nujol): 3550–3000, 1670–1570, 1275, 1130, 995, 900 cm$^{-1}$

NMR (DMSO-d$_6$, δ): 2.90–5.00 (9H, m); 6.80–8.30 (13H, m); 11.66 (1H, br s)

MASS: 560 (M+1), 417

10) (2R)-2-Benzyl-1-[3,5-bis(trifluoromethyl)benzoyl]-4-[3-(1H-indol-3-yl)propionyl]piperazine mp: 93°–95° C.

$[\alpha]_D^{28}$: −30.6° (C=1.0, MeOH)

IR (Nujol): 3450–3100, 1630, 1275, 1130, 900, 739 cm$^{-1}$

NMR (DMSO-d$_6$, δ): 2.60–5.00 (13H, m); 6.80–7.70 (12H, m); 8.12–8.18 (1H, m); 10.82 (1H, s)

MASS: 588 (M+1), 417

11) (2R)-2-Benzyl-1-[3,5-bis(trifluoromethyl)benzoyl]-4-[4-(1H-indol-3-yl)butyryl]piperazine mp: 88°–90° C.

$[\alpha]_D^{28}$: +11.0° (C=1.0, MeOH)

IR (Nujol): 3400–3100, 1630, 1275, 1130, 900, 737 cm$^{-1}$

NMR (DMSO-d$_6$, δ): 1.85–2.10 (2H, m); 2.30–5.10 (13H, m); 6.90–7.75 (12H, m); 8.10–8.20 (1H, m); 10.77 (1H, s)

MASS: 602 (M+1), 417

12) (2R)-2-Benzyl-1-[3,5-bis(trifluoromethyl)benzoyl]-4-[(3-phenyl)propioloyl]piperazine mp: 177–179° C.

$[\alpha]_D^{25}$: +10.80 (C=1.0, MeOH)

IR (Nujol): 2200, 1630, 1610, 1284, 1129, 906 cm$^{-1}$

NMR (DMSO-d$_6$, δ): 2.60–5.15 (9H, m); 6.95–7.80 (12H, m); 8.10–8.25 (1H, m)

MASS: 545 (M+1), 417

13) (2R)-2-Benzyl-1-[3,5-bis(trifluoromethyl)benzoyl]-4-(3-cyclohexylpropionyl)piperazine $[\alpha]_D^{25}$: +12.9° (C=1.0, MeOH)

IR (Neat): 3700–3300, 1635, 1272, 1126, 1005, 900, 700 cm$^{-1}$

NMR (DMSO-d$_6$, δ): 0.80–1.05 (2H, m); 1.05–1.38 (4H, m); 1.38–1.60 (2H, m); 1.60–1.85 (5H, m); 2.20–5.05 (11H, m); 6.90–7.05 (1H, m); 7.10–7.80 (6H, m); 8.10–8.20 (1H, m)

MASS: 555 (M+1), 417

14) (2R)-2-Benzyl-1-[3,5-bis(trifluoromethyl)benzoyl]-4-[2 (E)-benzylidenepropionyl]piperazine mp: 69°–73° C.

$[\alpha]_D^{25}$: +9.1° (C=1.0, MeOH)

IR (Neat): 3700–3300, 1620, 1274, 1125, 1008, 903, 697 cm$^{-1}$

NMR (DMSO-d$_6$, δ): 2.06 (3H, s); 2.60–5.10 (9H, m); 6.62 (1H, s); 6.95–7.05 (1H, m); 7.15–7.80 (11H, m); 8.10–8.20 (1H, m)

MASS: 561 (M+1), 417

15) (2R)-2-Benzyl-1-[3,5-bis(trifluoromethyl)benzoyl]-4-[3-(1H-indol-3-yl)-trans-acryloyl]piperazine mp: 125° C. (dec.)

[α]$_D^{24}$: +19.0° (C=1.0, MeOH)

IR (Nujol): 3500–3000, 1642, 1575, 1277, 1133, 900 cm$^{-1}$

NMR (DMSO-d$_6$, δ): 2.60–5.10 (9H, m); 6.90–8.30 (15H, m); 11.66 (1H, s)

MASS: 586 (M+1), 417

16) (2R)-2-Benzyl-1-[3,5-bis(trifluoromethyl)benzoyl]-4-(4-methyl-trans-cinnamoyl)piperazine mp: 152°–153° C.

[α]$_D^{24}$: +12.4° (C=1.0, MeOH)

IR (Nujol): 1634, 1604, 1510, 1286, 1185, 1128, 904 cm$^{-1}$

NMR (DMSO-d$_6$, δ): 2.34 (3H, s); 2.60–5.10 (9H, m); 6.80–7.80 (13H, m); 8.14–8.20 (1H, m)

MASS: 561 (M+1), 417

17) (2R)-2-Benzyl-1-[3,5-bis(trifluoromethyl)benzoyl]-4-(4-methoxy-trans-cinnamoyl)piperazine mp: 133°–134° C.

[α]$_D^{24}$: +12.5° (C=1.0, MeOH)

IR (Nujol): 1634, 1600, 1510, 1284, 1186, 1128, 903 cm$^{-1}$

NMR (DMSO-d$_6$, δ): 2.60–5.10 (12H, m); 6.96–7.80 (13H, m); 8.14–8.20 (1H, m)

MASS: 577 (M+1), 417

18) (2R)-2-Benzyl-1-[3,5-bis(trifluoromethyl)benzoyl]-4-(4-chloro-trans-cinnamoyl)piperazine mp: 135°–136° C.

[α]$_D^{24}$: +11.0° (C=1.0, MeOH)

IR (Nujol): 1633, 1601, 1490, 1275, 1175, 1035, 898 cm$^{-1}$

NMR (DMSO-d$_6$, δ): 2.60–5.10 (9H, m); 6.80–7.85 (13H, m); 8.14–8.20 (1H, m)

MASS: 581 (M+1), 417

19) (2R)-2-Benzyl-1-[3,5-bis(trifluoromethyl)benzoyl]-4-(4-N,N-dimethylamino-trans-cinnamoyl)piperazine mp: 114°–118° C.

[α]$_D^{24}$: +12.1° (C=1.0, MeOH)

IR (Nujol): 1634, 1605, 1521, 1280, 1170, 1127 cm$^{-1}$

NMR (DMSO-d$_6$, δ): 2.60–5.10 (15H, m); 6.70–6.74 (2H, m); 6.95–7.73 (11H, m); 8.14–8.20 (1H, m)

MASS: 590 (M+1), 417

20) (2R)-2-Benzyl-1-[3,5-bis(trifluoromethyl)benzoyl]-4-(4-phenyl-trans-cinnamoyl)piperazine mp: 159–160° C.

[α]$_D^{24}$: +9.9° (C=1.0, MeOH)

IR (Nujol): 1640, 1601, 1282, 1180, 1130, 906 cm$^{-1}$

NMR (DMSO-d$_6$, δ): 2.60–5.10 (9H, m); 6.85–7.95 (18H, m); 8.14–8.20 (1H, m)

MASS: 623 (M+1)

21) (2R)-2-Benzyl-1-[3,5-bis(trifluoromethyl)benzoyl]-4-(4-fluoro-trans-cinnamoyl)piperazine mp: 114°–116° C.

[α]$_D^{24}$: +13.60° (C=1.0, MeOH)

IR (Nujol): 1630, 1608, 1508, 1283, 1190, 1127, 905 cm$^{-1}$

NMR (DMSO-d$_6$, δ): 2.60–5.10 (9H, m); 6.80–7.90 (13H, m); 8.14–8.19 (1H, m)

MASS: 565 (M+1), 417

22) (2R)-2-Benzyl-1-[3,5-bis(trifluoromethyl)benzoyl]-4-(4-trifluoromethyl-trans-cinnamoyl)piperazine mp: 124°–126° C.

[α]$_D^{24}$: +12.9° (C=1.0, MeOH)

IR (Nujol): 1628, 1610, 1274, 1200, 1125, 905 cm$^{-1}$

NMR (DMSO-d$_6$, δ): 2.60–5.10 (9H, m); 6.85–8.10 (13H, m); 8.14–8.20 (1H, m)

MASS: 615 (M+1), 417

23) (2R)-2-Benzyl-1-[3,5-bis(trifluoromethyl)benzoyl]-4-[1-oxo-5-phenyl-2(E),4(E)-pentadienyl]piperazine mp: 103°–105° C.

[α]$_D^{24}$: +17.1° (C=1.0, MeOH)

IR (Nujol): 1631, 1600, 1285, 1184, 1130, 996, 902 cm$^{-1}$

NMR (DMSO-d$_6$, δ): 2.60–5.15 (9H, m); 6.70–7.80 (16H, m); 8.13–8.19 (1H, m)

MASS: 573 (M+1), 417

24) (2R)-2-Benzyl-1-[3,5-bis(trifluoromethyl)benzoyl]-4-(4-nitro-trans-cinnamoyl)piperazine mp: 141°–144° C.

[α]$_D^{25}$: +14.0° (C=1.0, MeOH)

IR (Nujol): 1645, 1610, 1510, 1350, 1327, 1280, 1177, 1128, 903 cm$^{-1}$

NMR (DMSO-d$_6$, δ): 2.60–5.10 (9H, m); 6.80–8.30 (14H, m)

MASS: 592 (M+1), 417

25) (2R)-2-Benzyl-1-[3,5-bis(trifluoromethyl)benzoyl]-4-[3-(3-pyridyl)-trans-acryloyl]piperazine mp: 139°–141° C.

[α]$_D^{25}$: +14.2° (C=1.0, MeOH)

IR (Nujol): 1632, 1608, 1280, 1190, 1125, 905 cm$^{-1}$

NMR (DMSO-d$_6$, δ): 2.60–5.10 (9H, m); 6.80–7.80 (10H, m); 8.14–8.19 (2H, m); 8.56 (1H, s); 8.90 (1H, s)

MASS: 548 (M+1), 417

26) (2R)-2-Benzyl-1-[3,5-bis(trifluoromethyl)benzoyl]-4-[3-(3-furyl)-trans-acryloyl]piperazine mp: 83°–85° C.

[α]$_D^{25}$: +11.8° (C=1.0, MeOH)

IR (Nujol): 1635, 1605, 1278, 1179, 1134, 902 cm$^{-1}$

NMR (DMSO-d$_6$, δ): 2.60–5.10 (9H, m); 6.90–8.20 (13H, m)

MASS: 537 (M+1), 417

27) (2R)-1-[3,5-Bis(trifluoromethyl)benzoyl]-2-(3,4-dimethylbenzyl)-4-(3-phenylpropionyl)piperazine

[α]$_D^{26}$: −4.8° (C=1.0, MeOH)

IR (Neat): 3450, 3050–2800, 1630, 1500, 1430, 1350, 1340 cm$^{-1}$

NMR (CDCl$_3$, δ): 2.1–2.3 (6H, m); 2.4–3.5 (11H, m); 3.6–4.1 (1H, m); 4.4–5.3 (1H, m); 6.5–7.5 (10H, m); 7.8–7.9 (1H, m)

MASS: 577 (M+1), 445

28) (2R)-2-Benzyl-1-[3,5-bis(trifluoromethyl)benzoyl]-4-(3-benzoyl-trans-acryloyl)piperazine mp: 110°–118° C.

[α]$_D^{22}$: +19.1° (C=1.0, MeOH)

IR (Nujol): 1636, 1280, 1181, 1130, 904 cm$^{-1}$

NMR (DMSO-d$_6$, δ): 2.60–5.10 (9H, m); 6.80–8.25 (15H, m)

MASS: 575 (M+1), 417

29) (2R)-2-Benzyl-1-[3,5-bis(trifluoromethyl)benzoyl]-4-[4-phenyl-3(E)-butenoyl]piperazine mp: 85°–87° C.

[α]$_D^{22}$: +19.5° (C=1.0, MeOH)

IR (Nujol): 1635, 1285, 1189, 1126, 903 cm$^{-1}$

NMR (DMSO-d$_6$, δ): 2.60–5.15 (11H, m); 6.30–6.60 (2H, m); 6.90–7.65 (12H, m); 8.13–8.20 (1H, m)

MASS: 561 (M+1), 417

30) (2R)-2-Benzyl-1-[3,5-bis(trifluoromethyl)benzoyl]-4-[3-(2-thienyl)-trans-acryloyl]piperazine mp: 118°–122° C.

[α]$_D^{22}$: +16.3° (C=1.0, MeOH)

IR (Nujol): 1633, 1499, 1281, 1183, 1127, 905 cm$^{-1}$
NMR (DMSO-d$_6$, δ): 2.60–5.10 (9H, m); 6.80–7.15 (2H, m); 7.15–7.85 (10H, m); 8.14–8.20 (1H, m)
MASS: 553 (M+1), 417

31) (2R)-4-[3-[2-(N-Acetylamino)thiazol-4-yl]-trans-acryloyl]-2-benzyl-1-[3,5-bis(trifluoromethyl)-benzoyl]piperazine
mp: 90°–94° C.
$[α]_D^{22}$: +11.3° (C=0.5, MeOH)
IR (Nujol): 1635, 1540, 1278, 1175, 1130, 900 cm$^{-1}$
NMR (DMSO-d$_6$, δ): 2.16 (3H, s); 2.60–4.60 (9H, m); 6.15–6.39 (1H, m); 6.98–7.80 (9H, m); 8.14–8.20 (1H, m); 12.28 (1H, br s)
MASS: 611 (M+1), 391

32) (2R)-2-Benzyl-1-[3,5-bis(trifluoromethyl)benzoyl]-4-(4-hydroxy-trans-cinnamoyl)piperazine
mp: 103°–105° C.
$[α]_D^{26}$: +12.3° (C=1.0, MeOH)
IR (Nujol): 3550–3000, 1636, 1600, 1511, 1277, 1130, 903 cm$^{-1}$
NMR (DMSO-d$_6$, δ): 2.60–5.15 (9H, m); 6.16–6.39 (1H, m); 6.78–7.80 (12H, m); 8.14–8.20 (1H, m); 9.88 (1H, s)
MASS: 563 (M+1), 417

33) (2R)-2-Benzyl-1-[3,5-bis(trifluoromethyl)benzoyl]-4-(2-naphthoyl)piperazine
mp: 87°–90° C.
$[α]_D^{22}$: +21.8° (C=1.0, MeOH)
IR (Nujol): 1635, 1276, 1175, 1129, 900 cm$^{-1}$
NMR (DMSO-d$_6$, δ): 2.60–4.70 (9H, m); 6.70–8.25 (15H, m)
MASS: 571 (M+1), 417

34) (2R)-2-Benzyl-1-[3,5-bis(trifluoromethyl)benzoyl]-4-(2-methoxy-trans-cinnamoyl)piperazine
mp: 104°–106° C.
$[α]_D^{26}$: +12.9° (C=1.0, MeOH)
IR (Nujol): 1634, 1610, 1287, 1184, 1128, 905 cm$^{-1}$
NMR (DMSO-d$_6$, δ): 2.60–5.10 (12H, m); 6.85–7.95 (13H, m); 8.14–8.20 (1H, m)
MASS: 577 (M+1), 417

35) (2R)-1-[3,5-Bis(trifluoromethyl)benzoyl]-2-(1H-indol-3-yl-methyl)-4-(4-nitro-trans-cinnamoyl)piperazine
mp: 128°–131° C.
$[α]_D^{22}$: -32.3° (C=1.0, MeOH)
IR (Nujol): 3260, 1637, 1608, 1516, 1277, 1175, 1140, 900 cm$^{-1}$
NMR (DMSO-d$_6$, δ): 2.80–5.20 (9H, m); 6.50–8.35 (14H, m); 10.87 (1H, br s)
MASS: 631 (M+1)

36) (2R)-1-[3,5-Bis(trifluoromethyl)benzoyl]-2-(1H-indol-3-yl-methyl)-4-(3-cyclohexylpropionyl)piperazine
mp: 190°–192° C.
$[α]_D^{26}$: -4.5° (C=1.0, MeOH)
IR (Nujol): 3280, 1649, 1627, 1276, 1170, 1130, 898 cm$^{-1}$
NMR (DMSO-d$_6$, δ): 0.60–1.80 (11H, m); 2.20–5.20 (13H, m); 6.60–8.30 (8H, m); 10.88 (1H, s)
MASS: 594 (M+1)

37) (2R)-2-Benzyl-1-[3,5-bis(trifluoromethyl)benzoyl]-4-(2-methoxyacetyl)piperazine
$[α]_D^{24}$: +13.0° (C=1.0, MeOH)
IR (Neat): 3650–3200, 1635, 1275, 1125, 903, 700 cm$^{-1}$
NMR (DMSO-d$_6$, δ): 2.60–5.10 (14H, m); 6.90–7.75 (7H, m); 8.10–8.20 (1H, m)
MASS: 489 (M+1), 417

38) (2R)-1-[3,5-Bis(trifluoromethyl)benzoyl]-2-(3,4-dimethylbenzyl)-4-[3-(3-pyridyl)-trans-acryloyl]-piperazine
mp: 81°–85° C.
$[α]_D^{21}$: -2.1° (C=1.0, MeOH)
IR (Nujol): 1635, 1610, 1450, 1350, 1320 cm$^{-1}$
NMR (CDCl$_3$, δ): 2.17 and 2.22 (6H, 2 s); 2.6–5.3 (9H, m); 6.4–8.0 (10H, m); 8.60 (1H, d, J=4.2 Hz); 8.7–8.9 (1H, m)

39) (2R)-1-[3,5-Bis(trifluoromethyl)benzoyl]-4-(4-chloro-trans-cinnamoyl)-2-(3,4-dimethylbenzyl)piperazine
mp: 68°–70° C.
$[α]_D^{23}$: -3.6° (C=1.0, MeOH)
IR (Nujol): 1645, 1605, 1490, 1450, 1370, 1350, 1320 cm$^{-1}$
NMR (CDCl$_3$, δ): 2.0–2.3 (6H, m); 2.6–3.5 (5H, m); 3.6–4.3 (2H, m); 4.6–5.3 (2H, m); 6.5–8.0 (12H, m)
MASS: 609 (M+1)

40) (2R)-1-[3,5-Bis(trifluoromethyl)benzoyl]-2-(3,4-dimethylbenzyl)-4-(4-fluoro-trans-cinnamoyl)piperazine
mp: 78°–80° C.
$[α]_D^{23}$: -3.5° (C=1.0, MeOH)
IR (Nujol): 1645, 1600, 1350, 1320 cm$^{-1}$
NMR (CDCl$_3$, δ): 2.0–2.3 (6H, m); 2.6–3.5 (5H, m); 3.6–4.3 (2H, m); 4.6–5.3 (2H, m); 6.5–8.0 (12H, m)
MASS: 593 (M+1), 445

41) (2R)-1-[3,5-Bis(trifluoromethyl)benzoyl]-2-(3,4-dimethylbenzyl)-4-(4-nitro-trans-cinnamoyl)piperazine
mp: 101°–105° C.
$[α]_D^{23}$: -3.3° (C=1.0, MeOH)
IR (Nujol): 1645, 1610, 1515, 1340, 1320 cm$^{-1}$
NMR (CDCl$_3$, δ): 2.0–2.3 (6H, m); 2.6–3.5 (5H, m); 3.6–4.5 (2H, m); 4.6–5.4 (2H, m); 6.6–8.0 (9H, m); 8.2–8.4 (3H, m)
MASS: 620 (M+1)

42) (2R)-1-[3,5-Bis(trifluoromethyl)benzoyl]-4-[3-cyclohexylpropionyl)-2-(3,4-dimethylbenzyl)piperazine
$[α]_D^{24}$: -5.5° (C=1.0, MeOH)
IR (Neat): 1635, 1500, 1430, 1380, 1350, 1320 cm$^{-1}$
NMR (CDCl$_3$, δ): 0.8–1.9 (13H, m); 2.1–3.1 (13H, m); 3.2–3.5 (2H, m); 3.7–4.2 (1H, m); 4.4–5.3 (1H, m); 6.5–7.5 (5H, m); 7.8–7.9 (1H, m)
MASS: 583 (M+1)

43) (2R)-2-Benzyl-1-[3,5-bis(trifluoromethyl)benzoyl]-4-[2-(3-pyridyl)acetyl]piperazine hydrochloride
$[α]_D^{22}$: +22.2° (C=1.0, MeOH)
IR (Neat): 3700–3100, 2700–2100, 1620, 1270, 1120, 901 cm$^{-1}$
NMR (DMSO-d$_6$, δ): 2.60–5.20 (11H, m); 6.90–8.88 (12H, m)
MASS: 536 (M+1) (free), 417

44) (2R)-4-(Benzofuran-2-yl-carbonyl)-2-benzyl-1-[3,5-bis(trifluoromethyl)benzoyl]piperazine
mp: 143°–145° C.
$[α]_D^{22}$: +7.3° (C=1.0, MeOH)
IR (Nujol): 1634, 1565, 1274, 1170, 1127, 894 cm$^{-1}$
NMR (DMSO-d$_6$, δ): 2.60–5.15 (9H, m); 6.90–7.80 (12H, m); 8.15–8.21 (1H, m)
MASS: 561 (M+1)

45) (2R)-2-Benzyl-1-[3,5-bis(trifluoromethyl)benzoyl]-4-[(3-pyridyl)carbonyl]piperazine hydrochloride
$[α]_D^{22}$: +17.8° (C=1.0, MeOH)
IR (Neat): 3700–3150, 2800–2100, 1630, 1275, 1125, 902 cm$^{-1}$
NMR (DMSO-d$_6$, δ): 2.60–5.20 (9H, m); 6.80–7.50 (6H, m); 7.60–8.00 (2H, m); 8.10–8.55 (2H, m); 8.85–9.15 (2H, m)
MASS: 522 (M+1) (free), 417

46) (2R)-1-[3,5-Bis(trifluoromethyl)benzoyl]-4-(4-chloro-trans-cinnamoyl)-2-(1H-indol-3-yl-methyl)piperazine
mp: 125°–138° C.

[α]$_D^{24}$: −34.8° (C=1.0, MeOH)
IR (Nujol): 3450–3100, 1638, 1605, 1277, 1175, 1130, 900 cm$^{-1}$
NMR (DMSO-d$_6$, δ): 2.60–5.15 (9H, m); 6.60–8.25 (14H, m); 10.80–11.00 (1H, m)
MASS: 620 (M+1)

47) (2R)-1-[3,5-Bis(trifluoromethyl)benzoyl]-4-(3-fluoro-trans-cinnamoyl)-2-(1H-indol-3-yl-methyl)piperazine
mp: 120°–130° C.
[α]$_D^{24}$: −32.2° (C=1.0, MeOH)
IR (Nujol): 3500–3100, 1635, 1605, 1275, 1175, 1130, 900 cm$^{-1}$
NMR (DMSO-d$_6$, δ): 2.70–5.20 (9H, m); 6.50–8.20 (14H, m); 10.87 (1H, s)
MASS: 604 (M+1)

48) (2R)-1-[3,5-Bis(trifluoromethyl)benzoyl]-4-(2-fluoro-trans-cinnamoyl)-2-(1H-indol-3-yl-methyl)piperazine
mp: 110°–114° C.
[α]$_D^{24}$: −29.8° (C=1.0, MeOH)
IR (Nujol): 3500–3100, 1637, 1608, 1276, 1175, 1130, 900 cm$^{-1}$
NMR (DMSO-d$_6$, δ): 2.80–5.20 (9H, m); 6.50–8.25 (14H, m); 10.87 (1H, s)
MASS: 604 (M+1)

49) (2R)-1-[3,5-Bis(trifluoromethyl)benzoyl]-4-(3-cyclopentylpropionyl)-2-(1H-indol-3-yl-methyl)piperazine
mp 180°–183° C.
[α]$_D^{20}$: −2.9° (C=1.0, MeOH)
IR (Nujol): 3280, 1650, 1628, 1277, 1212, 1170, 1131, 900 cm$^{-1}$
NMR (DMSO-d$_6$, δ): 0.85–1.35 (2H, m); 1.40–2.00 (9H, m); 2.20–5.15 (11H, m); 6.60–8.25 (8H, m); 10.88 (1H, s)
MASS: 580 (M+1)

50) (2R)-1-[3,5-Bis(trifluoromethyl)benzoyl]-4-[(3-cyclohexyl)-trans-acryloyl]-2-(1H-indol-3-yl-methyl)-piperazine
mp: 198°–200° C.
[α]$_D^{24}$: −19.0° (C=0.1, MeOH)
IR (Nujol): 3280, 1655, 1628, 1275, 1170, 1132, 900, 750 cm$^{-1}$
NMR (DMSO-d$_6$, δ): 0.65–1.25 (5H, m); 1.35–2.15 (6H, m); 2.55–5.00 (9H, m); 5.85–8.10 (10H, m); 10.60–10.80 (1H, m)
MASS: 592 (M+1)

51) (2R)-1-[3,5-Bis(trifluoromethyl)benzoyl]-4-(4-fluorobenzoyl)-2-(1H-indol-3-yl-methyl)piperazine
mp: 164°–165° C.
IR (Nujol): 3280, 1626, 1510 cm$^{-1}$
NMR (DMSO-d$_6$, δ): 2.55–5.05 (9H, m); 6.45–8.25 (12H, m); 10.84 (1H, s)
MASS: 578 (M+1)

52) (2R)-1-[3,5-Bis(trifluoromethyl)benzoyl]-2-(1H-indol-3-yl-methyl)-4-(3-nitro-trans-cinnamoyl)piperazine
mp: 127°–133° C.
[α]$_D^{24}$: −19.6° (C=1.0, MeOH)
IR (Nujol): 3450–3100, 1635, 1608, 1527, 1276, 1175, 1130, 900 cm$^{-1}$
NMR (DMSO-d$_6$, δ): 2.80–5.20 (9H, m); 6.55–8.80 (14H, m); 10.80–11.00 (1H, m)
MASS: 631 (M+1)

53) (2R)-1-[3,5-Bis(trifluoromethyl)benzoyl]-2-(1H-indol-3-yl-methyl)-4-(2-nitro-trans-cinnamoyl)piperazine
mp: 125°–133° C.
[α]$_D^{24}$: −18.9° (C=1.0, MeOH)
IR (Nujol): 3450–3100, 1637, 1607, 1520, 1278, 1175, 1130, 900 cm$^{-1}$
NMR (DMSO-d$_6$, δ): 2.80–5.20 (9H, m); 6.55–8.30 (14H, m); 10.80–10.95 (1H, m)
MASS: 631 (M+1), 456

54) (2R)-1-[3,5-Bis(trifluoromethyl)benzoyl]-2-(1H-indol-3-yl-methyl)-4-[(3-pyridyl)carbonyl]piperazine hydrochloride
mp: 150°–160° C.
[α]$_D^{24}$: +1.7° (C=1.0, MeOH)
IR (Nujol): 3650–3100, 2800–2000, 1625, 1280, 1180, 1127, 903 cm$^{-1}$
NMR (DMSO-d$_6$, δ): 2.80–5.20 (9H, m); 6.40–9.20 (12H, m)
MASS: 561 (M+1) (free)

55) (2R)-4-[2-(Benzoylamino)acetyl]-1-[3,5-bis(trifluoromethyl)benzoyl]-2-(1H-indol-3-yl-methyl)piperazine
mp: 123°–135° C.
[α]$_D^{24}$: −6.6° (C=0.5, MeOH)
IR (Nujol): 3600–3100, 1636, 1278, 1175, 1133, 903 cm$^{-1}$
NMR (DMSO-d$_6$, δ): 2.60–5.20 (11H, m); 6.55–8.21 (13H, m); 8.65–8.75 (1H, m); 10.80–11.00 (1H, m)
MASS: 617 (M+1), 456

56) (2R)-1-[3,5-Bis(trifluoromethyl)benzoyl]-4-(cyclopropylcarbonyl)-2-(1H-indol-3-yl-methyl)piperazine
mp: 109°–114° C.
[α]$_D^{20}$: −8.2° (C=1.0, MeOH)
IR (Nujol): 3500–3100, 1630, 1276, 1175, 1130, 902 cm$^{-1}$
NMR (DMSO-d$_6$, δ): 0.78 (4H, br s), 2.60–5.20 (10H, m); 6.60–8.25 (8H, m); 10.87 (1H, s)
MASS: 524 (M+1)

57) (2R)-1-[3,5-Bis(trifluoromethyl)benzoyl]-2-(1H-indol-3-yl-methyl)-4-[3-(3-pyridyl)-trans-acryloyl]-piperazine
mp: 86.5°–89.5° C.
[α]$_D^{24}$: −25.0° (C=1.0, MeOH)
IR (Nujol): 3600–3100, 1637, 1278, 1130, 900 cm$^{-1}$
NMR (DMSO-d$_6$, δ): 2.70–5.20 (9H, m); 6.15–8.35 (12H, m); 8.50–8.62 (1H, m); 8.75–9.05 (1H, m); 10.85–10.90 (1H, m)
MASS: 587 (M+1), 457

58) (2R)-1-[3,5-Bis(trifluoromethyl)benzoyl]-2-(3,4-dimethylbenzyl)-4-[4-trifluoromethyl-trans-cinnamoyl]piperazine
mp: 74°–76° C.
[α]$_D^{21}$: −2.3° (C=1.0, MeOH)
IR (Nujol): 1640, 1610, 1500, 1440, 1350, 1330 cm$^{-1}$
NMR (CDCl$_3$, δ): 2.12 and 2.22 (6H, 2 s); 2.7–5.3 (9H, m); 6.6–8.0 (12H, m)
MASS: 643 (M+1), 473, 455

59) (2R)-1-[3,5-Bis(trifluoromethyl)benzoyl]-2-(3,4-dimethylbenzyl)-4-(phenylpropioloyl)piperazine
mp: 72°–74° C.
[α]$_D^{21}$: +1.2° (C=1.0, MeOH)
IR (Nujol): 2200, 1625, 1490, 1450, 1350, 1320 cm$^{-1}$
NMR (CDCl$_3$, δ): 2.1–2.3 (6H, m); 2.6–5.4 (9H, m); 6.6–7.9 (11H, m)
MASS: 573 (M+1), 445

60) (2R)-1-[3,5-Bis(trifluoromethyl)benzoyl]-2-(3,4-dimethylbenzyl)-4-(3-cyclohexyl-trans-acryloyl)piperazine
mp: 78°–83° C.
[α]$_D^{21}$: −5.3° (C=1.0, MeOH)
IR (Nujol): 1640, 1620, 1500, 1430, 1340, 1320 cm$^{-1}$
NMR (CDCl$_3$, δ): 1.0–1.5 (5H, m); 1.6–1.9 (5H, m); 2.0–2.3 (7H, m); 2.5–5.3 (9H, m); 6.0–7.6 (7H, m); 7.87 (1H, br s)
MASS: 581 (M+1)

61) (2R)-1-[3,5-Bis(trifluoromethyl)benzoyl]-2-(3,4-dimethylbenzyl)-4-(3-pyridylcarbonyl)piperazine hydrochloride mp: 98°–100° C.
$[\alpha]_D^{24}$: +2.3° (C=1.0, MeOH)
IR (Neat): 2700–2300, 1635, 1500, 1430, 1370, 1350, 1340, 1330 cm$^{-1}$
NMR (DMSO-d$_6$, δ): 2.0–2.3 (6H, m); 2.8–5.2 (9H, m); 6.4–9.1 (11H, m)
MASS: 550 (M+1) (free)

Example 18

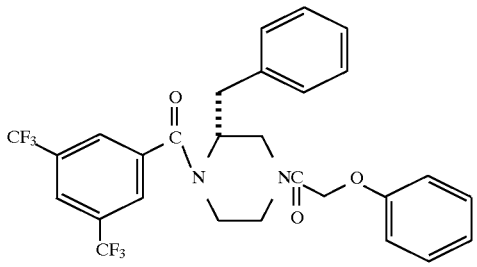

To a stirred solution of (2R)-2-benzyl-1-[3,5-bis(trifluoromethyl)benzoyl]piperazine (0.3 g) in dry dimethylformamide (3 ml) containing dry pyridine (0.06 ml) was added a solution of 2-phenoxyacetyl chloride (0.12 g) in dry dimethylformamide (1 ml) at 0° C., and the mixture was stirred at the same temperature for 30 minutes and then at room temperature for 30 minutes. Additional pyridine (0.02 ml) and a solution of 2-phenoxyacetyl chloride (0.025 g) in dry dimethylformamide (0.3 ml) were added to the reaction mixture. After being stirred for 30 minutes, the mixture was poured into water (43 ml) and extracted with ethyl acetate. The extract was washed with brine and dried over magnesium sulfate. After evaporation of the solvent, the residue was purified by a silica gel column chromatography. Elution with toluene-ethyl acetate afforded (2R)-2-benzyl-1-[3,5-bis(trifluoromethyl)benzoyl]-4-(2-phenoxyacetyl)piperazine (0.34 g) as a white powder.

$[\alpha]_D^{25}$: +28.9° (C=1.0, MeOH)
IR (Neat): 3700–3100, 1635, 1274, 1170, 1126, 900, 748 cm$^{-1}$
NMR (DMSO-d$_6$, δ): 2.80–5.20 (11H, m); 6.90–7.70 (12H, m); 8.12–8.22 (1H, m)
MASS: 551 (M+1), 417

Example 19

The following compounds were obtained according to a similar manner to that of Example 18.
1) (2R)-1-[3,5-Bis(trifluoromethyl)benzoyl]-2-(1H-indol-3-yl-methyl) -4-(N,N-dimethylaminocarbonyl)piperazine
IR (Nujol): 3230, 1621 cm$^{-1}$
NMR (DMSO-d$_6$, δ): 2.73 (1H, s); 2.82 (6H, s); 2.89 (1H, s); 2.70–4.98 (7H, m); 6.55–7.40 (5H, m); 7.40–8.24 (3H, m); 10.86 (1H, s)
MASS: 527 (M+1)
2) (2R)-2-Benzyl-1-[3,5-bis(trifluoromethyl)benzoyl]-4-mesylpiperazine
mp: 165°–166° C.
$[\alpha]_D^{26}$: +7.5° (C=1.0, MeOH)
IR (Nujol): 1652, 1325, 1282, 1165, 1128, 904, 790 cm$^{-1}$
NMR (DMSO-d$_6$, δ): 2.60–5.10 (12H, m); 6.95–7.05 (1H, m); 7.10–7.80 (6H, m); 8.15–8.25 (1H, m)
MASS: 495 (M+1), 417
3) (2R)-2-Benzyl-1-[3,5-bis(trifluoromethyl)benzoyl]-4-(2-phenylacetyl)piperazine
mp: 60°–65° C.
$[\alpha]_D^{26}$: +14.1° (C=1.0, MeOH)
IR (Neat): 3700–3200, 1635, 1275, 1175, 1125, 900, 700 cm$^{-1}$
NMR (DMSO-d$_6$, δ): 2.70–5.10 (11H, m); 6.80–7.00 (1H, m); 7.10–7.70 (11H, m); 8.10–8.20 (1H, m)
MASS: 535 (M+1), 417
4) (2R)-2-Benzyl-1-[3,5-bis(trifluoromethyl)benzoyl]-4-(N,N-dimethylcarbamoyl)piperazine
$[\alpha]_D^{27}$: –22.6° (C=1.0, MeOH)
IR (Neat): 3700–3300, 2900, 1630, 1490, 1430, 1275, 1125, 900 cm$^{-1}$
NMR (DMSO-d$_6$, δ): 2.60–5.10 (15H, m); 6.90–7.00 (1H, m); 7.10–7.75 (6H, m); 7.90–8.20 (1H, m)
MASS: 488 (M+1), 445
5) (2R)-2-Benzyl-1-[3,5-bis(trifluoromethyl)benzoyl]-4-acetylpiperazine
$[\alpha]_D^{25}$: +10.0° (C=1.0, MeOH)
IR (Neat): 3700–3150, 1635, 1275, 1125, 900, 700 cm$^{-1}$
NMR (DMSO-d$_6$, δ): 2.03–2.16 (3H, m); 2.60–5.10 (9H, m); 6.90–8.25 (8H, m)
MASS: 459 (M+1), 417
6) (2R)-2-Benzyl-1-[3,5-bis(trifluoromethyl)benzoyl]-4-(trifluoromethylcarbonyl)piperazine
mp: 57°–62° C.
$[\alpha]_D^{26}$: +10.3° (C=1.0, MeOH)
IR (Nujol): 1690, 1636, 1277, 1130, 900 cm$^{-1}$
NMR (DMSO-d$_6$, δ): 2.60–5.20 (9H, m); 6.90–8.30 (8H, m)
MASS: 513 (M+1), 417
7) (2R)-2-Benzyl-1-[3,5-bis(trifluoromethyl)benzoyl]-4-propionylpiperazine
mp: 52°–56° C.
$[\alpha]_D^{26}$: +11.3° (C=1.0, MeOH)
IR (Neat): 3700–3400, 1630, 1275, 1125, 1053, 1000, 903, 700 cm$^{-1}$
NMR (DMSO-d6, o): 0.99–1.10 (3H, m); 2.30–5.10 (11H, m); 6.90–7.05 (1H, m); 7.10–7.75 (6H, m); 8.10–8.25 (1H, m)
MASS: 473 (M+1), 417
8) (2R)-2-Benzyl-1-[3,5-bis(trifluoromethyl)benzoyl]-4-[2 (E)-butenoyl]piperazine
$[\alpha]_D^{25}$: +11.0° (C=1.0, MeOH)
IR (Neat): 3600–3300, 1680–1580, 1274, 1124, 900, 700 cm$^{-1}$
NMR (DMSO-d$_6$, δ): 1.86 (3H, d, J=6.0 Hz); 2.52–5.05 (9H, m); 6.40–8.00 (9H, m); 8.10–8.20 (1H, m)
MASS: 485 (M+1), 417
9) (2R)-2-Benzyl-1-[3,5-bis(trifluoromethyl)benzoyl]-4-butyrylpiperazine
$[\alpha]_D^{24}$: +15.1° (C=1.0, MeOH)
IR (Neat): 3650–3300, 1635, 1274, 1125, 1005, 900, 698 cm$^{-1}$
NMR (DMSO-d$_6$, δ): 0.86–0.97 (3H, m); 1.55 (2H, q, J=7.2 Hz); 2.29–5.10 (11H, m); 6.90–7.00 (1H, m); 7.15–7.80 (6H, m); 8.12–8.18 (1H, m)
MASS: 487 (M+1), 417
10) (2R)-4-Acetyl-1-[3,5-bis(trifluoromethyl)benzoyl]-2-(3,4-dimethylbenzyl)piperazine
$[\alpha]_D^{24}$: –12.1° (C=0.9, MeOH)
IR (Neat): 1650, 1630, 1450, 1350, 1320, 1270 cm$^{-1}$
NMR (CDCl$_3$, δ): 2.12 (3H, s); 2.25 (6H, s); 2.2–2.4 (2H, m); 2.6–3.5 (5H, m); 3.6–3.8 (1H, m); 4.6–4.8 (1H, m); 6.6–7.4 (4H, m); 7.8–8.0 (2H, m)
MASS: 487 (M+1), 445
11) (2R)-1-[3,5-Bis(trifluoromethyl)benzoyl]-2-(3,4-dimethylbenzyl)-4-(trans-cinnamaoyl)piperazine
mp: 87°–91° C.

$[\alpha]_D^{24}$: -3.0° (C=0.8, MeOH)

IR (Nujol): 1635, 1605, 1430 cm$^{-1}$

NMR (CDCl$_3$, δ): 2.0–2.3 (6H, m); 2.6–3.5 (5H, m); 3.6–4.5 (2H, m); 4.6–5.4 (2H, m); 6.6–7.7 (11H, m); 7.78 (1H, d, J=15.2 Hz); 7.90 (1H, br s)

MASS: 575 (M+1), 445

12) (2R)-1-[3,5-Bis(trifluoromethyl)benzoyl]-2-(1H-indol-3-yl-methyl)-4-propionylpiperazine mp: 177°–178° C.

$[\alpha]_D^{22}$: -8.7° (C=1.0, MeOH)

IR (Nujol): 3300, 1635, 1282, 1224, 1124, 905, 748 cm$^{-1}$

NMR (DMSO-d$_6$, δ): 0.90–1.15 (3H, m); 2.20–5.15 (11H, m); 6.75–8.25 (8H, m); 10.87 (1H, s)

MASS: 512 (M+1)

13) (2R)-1-[3,5-Bis(trifluoromethyl)benzoyl]-2-(1H-indol-3-yl-methyl)-4-mesylpiperazine mp: >225° C.

$[\alpha]_D^{21}$: +20.6° (C=1.0, DMF)

IR (Nujol): 3390, 1634, 1318, 1280, 1139, 964, 898, 747 cm$^{-1}$

NMR (DMSO-d$_6$, δ): 2.80–5.10 (12H, m); 6.55–8.25 (8H, m); 10.91 (1H, s)

MASS: 534 (M+1), 456

Example 20

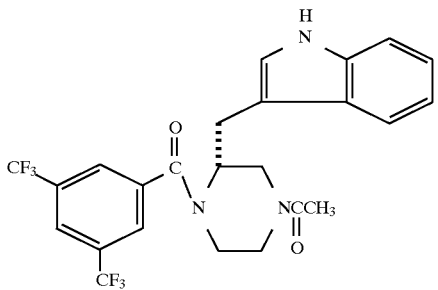

To a stirred mixture of (2R)-1-[3,5-bis(trifluoro-methyl)benzoyl]-2-(1H-indol-3-yl-methyl)piperazine (0.15 g) and potassium carbonate (0.14 g) in dimethylformamide (10 ml) was added acetyl chloride (0.04 ml) at room temperature. After being stirred for 3 hours, the reaction mixture was quenched with water (50 ml) and extracted with dichloromethane (50 ml). The organic layer was washed with aqueous sodium bicarbonate solution and brine, and dried over magnesium sulfate. After evaporation of the solvent, the residue was purified on a silica gel column (10 g) eluting with a mixture of dichloromethane and methanol (20:1). The fractions containing object compound were collected and evaporated under reduced pressure. To the resulting oily product was added a mixed solvent of ethyl ether and diisopropyl ether, and the mixture was concentrated under reduced pressure. The obtained powder was collected by filtration and dried in vacuo to give (2R)-4-acetyl-1-[3,5-bis(trifluoromethyl)benzoyl]-2-(1H-indol-3-yl-methyl) piperazine (0.09 g) as a powder.

IR (CHCl$_3$): 3270, 2990, 2900, 1630 cm$^{-1}$

NMR (DMSO-d$_6$, δ): 1.9–2.2 (3H, m); 2.73 (1H, s); 2.89 (1H, s); 2.65–3.12 (3H, m); 3.15–3.48 (1H, m), 3.65–4.10 (2H, m); 4.20–4.68 (1H, m); 6.58–7.48 (5H, m); 7.60–8.26 (3H, m); 10.88 (1H, s)

MASS: 498 (M+1)

Example 21

The following compounds were obtained according to a similar manner to that of Example 20.

1) (2R)-4-Acetyl-1-[3,5-bis(trifluoromethyl)benzoyl]-2-(N-methyl-1H-indol-3-yl-methyl)piperazine IR (CHCl$_3$): 3460, 3000, 2920, 1620 cm$^{-1}$ NMR (DMSO-d$_6$, δ): 1.9–2.2 (3H, m); 2.73 (1H, s); 2.89 (1H, s); 2.68–3.14 (2H, m); 2.68–3.56 (2H, m); 3.71–3.75 (3H, s); 3.60–4.10 (2H, m); 4.10–4.65 (1H, m); 6.60–8.28 (8H, m)

MASS: 512 (M+1)

2) (2R)-4-[3-[2-(Acetylamino)thiazol-4-yl]-trans-acryloyl]-1-[3,5-bis(trifluoromethyl)benzoyl]-2-(3,4-dimethylbenzyl)piperazine mp: 145°–149° C.

$[\alpha]_D^{21}$: -0.7° (C=1.0, MeOH)

IR (Nujol): 3200, 1690, 1635, 1605, 1545, 1500, 1350, 1340, 1320 cm$^{-1}$

NMR (CDCl$_3$, δ): 2.14 and 2.20 (6H, 2 s); 2.28 (3H, s); 2.6–5.3 (9H, m); 6.5°–7.4 (6H, m); 7.10 (1H, m); 7.66 (1H, d, J=14.8 Hz); 7.86 (1H, br s); 9.2–9.7 (1H, m)

MASS: 639 (M+1), 445

3) (2R)-4-[3-[2-(Acetylamino)thiazol-4-yl]-trans-acryloyl]-1-[3,5-bis(trifluoromethyl)benzoyl]-2-(1H-indol-3-yl-methyl)piperazine mp: 167°–172° C.

$[\alpha]_D^{20}$: -45.1° (C=1.0, MeOH)

IR (Nujol): 3550–3100, 1685, 1635, 1545, 1276, 1175, 1130, 900 cm$^{-1}$

NMR (DMSO-d$_6$, δ): 2.16 (3H, s); 2.75–5.15 (9H, m); 6.60–8.25 (11H, m); 10.88 (1H, s); 12.20–12.45 (1H, m)

MASS: 650 (M+1)

Example 22

To a mixture of (2R)-2-benzyl-1-[3,5-bis(trifluoromethyl)benzoyl]piperazine (0.3 g) and acetic acid (1.2 ml) in dioxane (1.2 ml) was added 37% formalin (0.05 ml) at room temperature. The resulting mixture was cooled to 0° C., and then a solution of indole (0.08 g) in dioxane (1.2 ml) was added. The mixture was stirred at room temperature for 30 minutes and then quenched with water (6 ml). The pH of the resulting mixture was adjusted to 8.0 by addition of aqueous sodium bicarbonate solution. The mixture was extracted with ethyl acetate and the extract was washed with brine, and dried over magnesium sulfate. After evaporation of the solvent, the residue was purified or a silica gel column (15 g) eluting with a mixture of toluene and ethyl acetate (5:1). The eluate was concentrated and treated with 4N hydrogen chloride in ethyl acetate solution to give (2R)-2-benzyl-1-[3,5-bis(trifluoromethyl)benzoyl]-4-(1H-indol-3-yl-methyl)piperazine hydrochloride (0.31 g) as a powder like a foam.

mp: 168°–170° C.

$[\alpha]_D^{28}$: +0.7° (C=1.0, MeOH)

IR (Nujol): 3200, 2520, 1639, 1275, 1126, 903 cm$^{-1}$

NMR (DMSO-d$_6$, δ): 2.80–5.10 (11H, m); 6.84–6.87 (1H, m); 7.05–7.90 (11H, m); 8.16–8.20 (1H, m); 11.00–11.40 (1H, m); 11.57 (1H, s)

MASS: 546 (M+l) (free), 417, 130

Example 23

To a solution of (2R)-1-[3,5-bis(trifluoromethyl)-benzoyl]-2-(1H-indol-3-yl-methyl)piperazine (0.1 g) in dichloromethane (10 ml) was added 4N hydrogen chloride in dioxane solution (0.05 ml) at 0° C. The resulting mixture was stirred at the same temperature for 50 minutes and then concentrated under reduced pressure. The obtained powder was collected by filtration and washed with ethyl ether to give (2R)-1-[3,5-bis(trifluoromethyl)-benzoyl]-2-(1H-indol-3-yl-methyl)piperazine hydrochloride (0.1 g).

IR (Nujol): 3340, 1648 cm$^{-1}$

NMR (DMSO-d$_6$, δ): 2.9–3.9 (8H, m); 3.9–5.2 (1H, m); 6.57–7.50 (5H, m); 7.50–8.30 (3H, m); 9.40–10.00 (2H, m); 10.96 (1H, s)

MASS: 456 (M+1) (free)

Example 24

The following compounds were obtained according to a similar manner to that of Example 23.

1) (2R)-4-Benzyl-1-[3,5-bis(trifluoromethyl)benzoyl]-2-(1H-indol-3-yl-methyl)piperazine hydrochloride NMR (DMSO-d$_6$, δ): 2.80–4.30 (9H, m); 4.40–4.75 and 4.95–5.15 (2H, 2 m); 6.45–8.30 (13H, m); 10.85 (1H, s); 11.10–11.65 (1H, m)

2) (2R)-1-[3,5-Bis(trifluoromethyl)benzoyl]-2-(1H-indol-3-yl-methyl)-4-(3-phenylpropyl)piperazine hydrochloride IR (Nujol): 3200, 1636 cm$^{-1}$ NMR (DMSO-d$_6$, δ): 2.00–2.25 (2H, m); 2.55–2.77 (2H, m); 2.90–4.16 (11H, m); 6.80–7.48 (10H, m); 7.55–8.28 (3H, m); 10.94 (1H, s); 11.26, 11.40 (1H, br s)

MASS: 574 (M+1) (free)

3) (2R)-1-[3,5-Bis(trifluoromethyl)benzoyl]-2-(N-methyl-1H-indol-3-yl-methyl)-4-methylpiperazine hydrochloride mp: 221°–226° C.

IR (Nujol): 3340, 2700, 1624 cm$^{-1}$

NMR (DMSO-d$_6$, δ): 2.78 and 2.82 (3H, 2 s); 2.97–3.83 and 4.00–4.18 (8H, 2 s); 3.71, 3.76 (3H, s); 4.48–4.69 and 4.98–5.16 (1H, 2 m); 6.62–8.29 (8H, m); 11.36, 11.49 (1H, br s)

MASS: 484 (M+1) (free)

4) (2R)-1-[3,5-Bis(trifluoromethyl)benzoyl]-2-(1H-indol-3-yl-methyl)-4-[2-(N,N-dimethylamino)acetyl]-piperazine hydrochloride IR (Nujol): 3300–3200, 2700, 1625 cm$^{-1}$ NMR (DMSO-d$_6$, δ): 2.5–2.8 (6H, m); 2.84–4.46 (11H, m); 6.50–8.29 (8H, m); 8.41 and 8.80 (1H, 2 br s); 11.00 (1H, s)

MASS: 541 (M+1) (free)

5) (2R)-4-Benzyl-1-[3,5-bis(trifluoromethyl)benzoyl]-2-(N-methyl-1H-indol-3-yl-methyl)piperazine hydrochloride

[α]$_D^{28}$: +13.1° (C=1.0, CHCl$_3$)

IR (Nujol): 3360, 2550, 1636 cm$^{-1}$

NMR (DMSO-d$_6$, δ): 2.90–3.52 (4H, m); 3.59 and 3.64 (3H, 2 s); 3.52–4.29 (5H, m); 4.47–4.74 and 4.90–5.10 (2H, 2 m); 6.50–8.30 (13H, m)

MASS: 560 (M+1) (free)

6) (2R)-2-Benzyl-1-[3,5-bis(trifluoromethyl)benzoyl]-4-(methoxycarbonylmethyl) piperazine hydrochloride mp: 126°–129° C.

[α]$_D^{25}$: –12.1° (C=1.0, MeOH)

IR (Nujol): 3650, 3100, 2700–2100, 1745, 1635, 1277, 1130, 900 cm$^{-1}$

NMR (DMSO-d$_6$, δ): 2.80–5.20 (14H, m); 6.91–7.80 (7H, m); 8.19–8.23 (1H, m)

MASS: 489 (M+1) (free), 417

7) (2R)-4-Benzyl-1-[3,5-bis(trifluoromethyl)benzoyl]-2-(3,4-dimethylbenzyl)piperazine hydrochloride mp: 146°–150° C.

[α]$_D^{28}$: –17.1° (C=1.0, MeOH)

IR (Nujol): 3350, 2700–2300 (br), 1640 cm$^{-1}$

NMR (DMSO-d$_6$, δ): 2.0–2.2 (6H, m); 2.8–4.3 (9H, m); 4.4–5.0 (2H, m); 6.5–7.1 (3H, m); 7.4–7.8 (7H, m); 8.1–8.2 (1H, m)

MASS: 535 (M+1) (free)

8) (2R)-1-[3,5-Bis(trifluoromethyl)benzoyl]-2-(3,4-dimethylbenzyl) piperazine hydrochloride mp: 125°–130° C.

[α]$_D^{28}$: –30.4° (C=1.0, MeOH)

IR (Nujol): 3350, 2700–2500 (br), 1640, 1500, 1360, 1330 cm$^{-1}$

NMR (DMSO-d$_6$, δ): 2.0–2.2 (6H, m); 2.6–5.0 (9H, m); 6.6–7.7 (5H, m); 8.1–8.2 (1H, m); 9.2–9.6 (1H, br m)

MASS: 445 (M+1) (free)

9) (2R)-1-[3,5-Bis(trifluoromethyl)benzoyl]-2-(3,4-dimethylbenzyl)-4-(3-phenylpropyl)piperazine hydrochloride mp: 211°–212° C.

[α]$_D^{27}$: –16.6° (C=1.0, MeOH)

IR (Nujol): 3350, 2700–2400 (br), 1630, 1500, 1360 cm$^{-1}$

NMR (DMSO-d$_6$, δ): 2.0–2.3 (8H, m); 2.6–4.0 (12H, m); 4.5–5.2 (1H, m); 6.7–7.7 (10H, m); 8.1–8.2 (1H, m); 11.0–11.4 (1H, m)

MASS: 563 (M+1) (free)

10) (2R)-1-[3,5-Bis(trifluoromethyl)benzoyl]-2-(1H-indol-3-yl-methyl)-4-(methoxycarbonylmethyl)piperazine hydrochloride mp: 167°–169° C.

[α]$_D^{25}$: –30.0° (C=1.0, MeOH)

IR (Nujol): 3700–3100, 2750–2000, 1749, 1638, 1278, 1175, 1130, 903 cm$^{-1}$

NMR (DMSO-d$_6$, δ): 2.60–5.15 (14H, m); 6.60–8.30 (8H, m); 10.97 (1H, s)

MASS: 528 (M+1) (free)

11) (2R)-2,4-Dibenzyl-1-[3,5-bis(trifluoromethyl)-benzoyl]piperazine hydrochloride mp: 213°–217° C.

[α]$_D^{28}$: –3.6° (C=1.0, MeOH)

IR (Nujol): 2700–2000, 1640, 1272, 1135 cm$^{-1}$

NMR (DMSO-d$_6$, δ): 2.90–4.30 (8H, m); 4.40–5.10 (3H, m); 6.80–7.60 (9H, m); 7.70–8.30 (4H, m); 11.30–11.80 (1H, m)

MASS: : 507 (M+1) (free), 417

12) (2R)-2-Benzyl-1-[3,5-bis(trifluoromethyl)benzoyl]-piperazine hydrochloride mp: 222°–224° C.

[α]$_D^{28}$: –7.4° (C=1.0, MeOH)

IR (Nujol): 3520, 2800–2300, 1640, 1272, 1980, 1130 cm$^{-1}$

NMR (DMSO-d$_6$, δ): 2.60–5.20 (10H, m); 6.80–7.80 (7H, m); 8.15 (1H, s); 9.66 (1H, br s)

MASS: 417 (M+1) (free)

13) (2R)-1-[3,5-Bis(trifluoromethyl)benzoyl]-2-(3,4-dimethylbenzyl)-4-[3-(3-pyridyl)-trans-acryloyl]-piperazine hydrochloride mp: 100°–110° C. (dec.)

[α]$_D^{24}$: –2.5° (C=1.0, MeOH)

IR (Nujol): 3350, 2700–2500, 1640–1600, 1550, 1350, 1320 cm$^{-1}$

NMR (DMSO-d$_6$, δ): 2.0–2.3 (8H, m); 2.5–3.9 (5H, m); 4.3–5.1 (2H, m); 5.0–6.0 (1H, br s); 6.2–7.2 (3H, m); 7.4–8.3 (6H, m); 8.8–9.0 (2H, m); 9.2–9.4 (1H, m)

MASS: 576 (M+1) (free)

14) (2R)-1-[3,5-Bis(trifluoromethyl)benzoyl]-2-(3,4-dimethylbenzyl)-4-(methoxycarbonylmethyl)piperazine hydrochloride mp: 137°–1380C.

[α]$_D^{23}$: –27.3° (C=1.0, MeOH)

IR (Nujol): 3340, 2700–2300, 1750, 1635, 1500, 1360 cm$^{-1}$

NMR (DMSO-d$_6$, δ): 2.0–2.3 (6H, m); 2.7–5.1 (11H, m); 3.74 (3H, m); 6.70 (1H, br s); 6.9–7.2 (2H, m); 7.44 (1H, br s); 7.18 (1H, br s); 8.19 (1H, br s)

MASS: 517 (M+1) (free), 445

Example 25

The following compounds were obtained according to a similar manner to that of Example 9.

1) (2R)-1-[3,5-Bis(trifluoromethyl)benzoyl]-4-(carbamoylmethyl)-2-(3,4-dimethylbenzyl)piperazine hydrochloride mp: 185°–186° C.

$[\alpha]_D^{23}$: −22.8° (C=1.0, MeOH)

IR (Nujol): 3350, 3150, 1685, 1635, 1500, 1380, 1350, 1320 cm$^{-1}$

NMR (DMSO-d$_6$, δ): 2.0–2.3 (6H, m); 2.6–4.2 (13H, m); 4.5–5.2 (1H, m); 6.6–8.3 (6H, m)

MASS: 502 (M+1) (free), 445

2) ($^2$R)-1-[3,5-Bis(trifluoromethyl)benzoyl]-2-(1H-indol-3-yl-methyl)-4-(carbamoylmethyl)piperazine mp: 170°–173° C.

$[\alpha]_D^{20}$: −5.5° (C=1.0, MeOH)

IR (Nujol): 3550–3000, 1691, 1600, 1276, 1222, 1190, 1130, 902 cm$^{-1}$

NMR (DMSO-d$_6$, δ): 2.00–4.95 (11H, m), 6.60–8.25 (10H, m); 10.86 (1H, s)

MASS: 513 (M+1), 456

Example 26

A mixture of (2R)-1-[3,5-bis(trifluoromethyl)-benzoyl]-2-(1H-indol-3-yl-methyl)-4-(methoxycarbonyl-methyl)piperazine (0.15 g) and 30% methylamine ethanol solution (5 ml) was left at about 4° C. in a refrigerator. After 24 hours, the mixture was evaporated and the residue was chromatographed on a column of silica gel with a mixture of dichloromethane and methanol. The eluates were collected and evaporated. The product was dissolved in ethyl acetate (2 ml) and then treated with 4N hydrogen chloride in ethyl acetate solution to afford (2R)-1-[3,5-bis (trifluoromethyl) benzoyl]-2-(1H-indol-3-yl-methyl)-4-(N-methylcarbamoylmethyl)piperazine hydrochloride (0.14 g) as a white powder.

mp: 175°–1800C.

$[\alpha]_D^{21}$: −26.0° (C=1.0, MeOH)

IR (Nujol): 3700–3100, 2700–2000, 1673, 1635, 1276, 1173, 1131, 903 cm$^{-1}$

NMR (DMSO-d$_6$, δ): 2.69 (3H, s); 2.80–5.10 (11H, m); 6.60–8.80 (9H, m); 10.99 (1H, s)

MASS: 527 (M+1) (free)

Example 27

To a stirred mixture of (2R)-1-[3,5-bis(trifluoromethyl) benzoyl]-2-(3,4-dimethylbenzyl)-4-(carboxymethyl) piperazine hydrochloride (210 mg), N-methylbenzylamine (52 mg) and triethylamine (0.19 ml) in dichloromethane (5 ml) was added 2-chloro-1-methylpyridinium iodide (110 mg) under nitrogen atmosphere at room temperature. The mixture was stirred at the same temperature for 1 hour. After removal of the solvent, the residue was purified by column chromatography on a silica gel eluting with a mixture of dichloromethane and methanol (10:1). The eluate was concentrated and treated with 4N hydrogen chloride in ethyl acetate solution to give (2R)-1-[3,5-bis(trifluoromethyl) benzoyl]-2-(3,4-dimethylbenzyl)-4-[(N-methyl-N-benzylcarbamoyl)methyl]-piperazine hydrochloride (190 mg) as a powder.

mp: 145°–149° C. (dec.)

$[\alpha]_D^{21}$: −15.2° (C=0.5, MeOH)

IR (Nujol): 2700–2500, 1650, 1360, 1330 cm$^{-1}$

NMR (DMSO-d$_6$, δ): 2.10 and 2.18 (6H, 2 s); 2.86 and 2.95 (3H, 2 s); 2.7–5.2 (13H, m); 6.6–6.8 (1H, m); 6.9–7.5 (8H, m); 7.67 (1H, br s); 8.2–8.3 (1H, m); 10.0–10.4 (1H, m)

MASS: 606 (M+1) (free), 445

Example 28

A mixture of (2R)-1-[3,5-bis(trifluoromethyl)-benzoyl]-2-(3,4-dimethylbenzyl)piperazine (0.5 g), tert-butyl bromoacetate (0.2 ml) and triethylamine (0.31 ml) in tetrahydrofuran (10 ml) was stirred at room temperature for 12 hours. After filtration, the filtrate was concentrated to a syrup, which was subjected to a chromatography on a silica gel with a mixture of toluene and ethyl acetate (20:1) to afford (2R)-1-[3,5-bis(trifluoromethyl)benzoyl]-2-(3,4-dimethylbenzyl)-4-(tert-butoxycarbonylmethyl) piperazine (0.52 g). This compound was treated with 4N hydrogen chloride in ethyl acetate solution to give (2R)-1-[3,5-bis (trifluoromethyl)benzoyl]-4-carboxymethyl-2-(3,4-dimethylbenzyl)piperazine hydrochloride (0.33 g) as a white powder.

mp: 195°–197° C.

$[\alpha]_D^{24}$: −28.3° C. (C=1.0, MeOH)

IR (Nujol): 3100, 2700–2300, 1720, 1635, 1500, 1400 cm$^{-1}$

NMR (DMSO-d$_6$, δ): 2.10 and 2.18 (6H, 2 s); 2.7–5.2 (13H, m); 6.6–7.2 (3H, m); 7.4–7.8 (2H, m); 8.20 (1H, br s)

MASS: 503 (M+1) (free)

Example 29

The following compounds were obtained according to a similar manner to that of Example 6.

1) (2R)-1-(3,5-Dimethylbenzoyl)-2-(3,4-dimethylbenzyl)piperazine

IR (Neat): 3300, 3050–2700, 1620, 1500, 1420 cm$^{-1}$

NMR (CDCl$_3$, δ): 2.1–2.4 (12H, m); 2.6–5.1 (10H, m); 6.5–6.8 (3H, m); 6.9–7.1 (3H, m)

MASS: 337 (M+1)

2) (2R)-1-[3,5-Bis(trifluoromethyl)benzoyl]-2-[(1R)-1-(N-methyl-1H-indol-3-yl)ethyl]piperazine IR (Neat): 3300, 1730, 1630, 1430 cm$^{-1}$ NMR (CDCl$_3$, δ): 1.4–1.5 (3H, m); 2.5–3.6 (7H, m); 3.70 (3H, s); 3.9–4.1 (1H, m); 4.9–5.0 (1H, m); 6.6–7.4 (5H, m); 7.6–8.5 (3H, m)

MASS: 484 (M+1)

Example 30

The following compounds were obtained according to a similar manner to that of Example 11.

1) (2R)-4-(Benzyloxycarbonylmethyl)-1-[3,5-bis (trifluoromethyl)benzoyl]-2-(3,4-dimethylbenzyl) piperazine IR (Neat): 3000–2700 (br), 1740, 1635, 1500, 1430 cm$^{-1}$ NMR (CDCl$_3$, δ): 2.1–2.3 (6H,.m); 2.4–3.8 (10H, m); 4.6–5.1 (1H, m); 5.17 (2H, s); 6.65 (1H, br s); 6.9–7.5 (9H, m); 7.82 (1H, s)

MASS: 593 (M+1), 445

2) (2R)-1-(3,5-Dimethylbenzoyl)-2-(3,4-dimethylbenzyl)-4- (methoxycarbonylmethyl)piperazine IR (Neat): 3000–2700, 1745, 1630, 1600, 1500, 1420 cm$^{-1}$ NMR (CDCl$_3$, δ): 2.1–2.4 (12H, m); 2.6–5.1 (11H, m); 3.72 (3H, s); 6.4–6.9 (3H, m); 7.0–7.3 (3H, m)

MASS: 409 (M+1), 365

3) (2R)-1-[3,5-Bis(trifluoromethyl)benzoyl]-2-(1H-indol-3-yl-methyl)-4-[(4-trityl-1-piperazinyl)-carbonylmethyl]piperazine mp: 160° 166° C.

$[\alpha]_D^{21}$: −23.0° (C=0.5, DMF)

IR (Nujol): 3600–3100, 1635, 1277, 1175, 1133, 900 cm$^{-1}$

NMR (DMSO-d$_6$, o): 1.80–5.00 (19H, m); 6.60–8.20 (23H, m); 10.85 (1H, s)

MASS: 824 (M+1), 580

4) (2R)-1-[3,5-Bis(trifluoromethyl)benzoyl]-2-(3,4-dimethylbenzyl)-4-(3-phthalimidopropyl)piperazine mp: 146°–147° C.

$[\alpha]_D^{18}$: −25.8° (C=0.5, MeOH)

IR (Nujol): 1765, 1700, 1630, 1610, 1500, 1450, 1420, 1390, 1350 cm$^{-1}$

NMR (CDCl$_3$, δ): 1.85 (2H, sext, J=9.0 Hz); 2.15 and 2.21 (6H, 2 s); 2.44 (2H, t, J=9.0 Hz); 3.84 (2H, t, J=9.0 Hz); 2.6–5.2 (9H, m); 6.5–7.5 (4H, m); 7.7–8.0 (6H, m)

MASS: 632 (M+1)

5) (2R)-1-[3,5-Bis(trifluoromethyl)benzoyl]-2-(3,4-dimethylbenzyl)-4-[(3-pyridyl)carbonylmethyl]-piperazine hydrochloride mp: 145°–155° C. (dec.)

$[\alpha]_D^{18}$: −18.3° (C=1.0, MeOH)

IR (Nujol): 3350, 2700–2300, 1715, 1640, 1500, 1450, 1350 cm$^{-1}$

NMR (DMSO-d$_6$, δ): 2.1–2.4 (6H, m); 2.8–5.4 (12H, m); 6.7–7.4 (3H, m); 7.47 (1H, br s); 7.7–8.6 (4H, m); 8.9–9.0 (1H, m); 9.24 (1H, br s)

MASS: 564 (M+1) (free), 445

6) (2R)-1-[3,5-Bis(trifluoromethyl)benzoyl]-2-(3,4-dimethylbenzyl)-4-(2-phthalimidoethyl)piperazine mp: 161°–162° C.

$[\alpha]_D^{20}$: +1.6° (C=0.5, DMF)

IR (Nujol): 1770, 1710, 1630, 1500, 1550, 1535, 1410, 1400, 1350 cm$^{-1}$

NMR (DMSO-d$_6$, δ) 2.02 and 2.12 (6H, 2 s); 2.2–4.8 (13H, m); 6.3–7.3 (3H, m); 7.41 (1H, s); 7.66 (1H, s); 7.8–8.0 (4H, m); 8.11 (1H, br s)

MASS: 618 (M+1)

7) (2R)-4-[4-(Ethoxycarbonyl)butyl]-1-[3,5-bis(trifluoromethyl)benzoyl]-2-(1H-indol-3-yl-methyl)piperazine $[\alpha]_D^{20}$: −0.6° (C=0.5, DMF)

IR (Neat): 3300, 1720, 1620, 1275, 1175, 1125, 900 cm$^{-1}$

NMR (DMSO-d$_6$, δ): 1.18 (3H, t, J=7.1 Hz); 1.30–5.00 (19H, m); 6.60–8.20 (8H, m); 10.85 (1H, s)

MASS: 584 (M+1), 456

8) (2R)-1-[3,5-Bis(trifluoromethyl)benzoyl]-2-(1H-indol-3-yl-methyl)-4-[3-(methoxycarbonyl)propyl]piperazine hydrochloride mp: 133°–134° C.

$[\alpha]_D^{18}$: +0.8° (C=0.5, DMF)

IR (Nujol): 3600–3100, 2800–2000, 1725, 1635, 1277, 1173, 1130, 900 cm$^{-1}$

NMR (DMSO-d$_6$, δ): 1.90–5.20 (18H, m); 6.60–8.20 (8H, m); 10.94 (1H, s); 11.10–11.50 (1H, m)

MASS: 556 (M+l) (free)

9) (2R)-4-[3-(Benzyloxycarbonyl)propyl]-1-[3,5-bis(trifluoromethyl)benzoyl]-2-(1H-indol-3-yl-methyl)piperazine $[\alpha]_D^{21}$: 1.8° (C=0.5, DMF)

IR (Neat): 3550–3100, 1727, 1625, 1274, 1130, 900 cm$^{-1}$

NMR (DMSO-d$_6$, 6): 1.70–2.40 (6H, m); 2.60–5.00 (9H, m); 5.12 (2H, s); 6.60–8.20 (13H, m); 10.85 (1H, s)

MASS: 632 (M+1)

10) (2R)-4-(Benzyloxycarbonylmethyl)-1-[3,5-bis(trifluoromethyl)benzoyl]-2-(1H-indol-3-yl-methyl)piperazine $[\alpha]_D^{21}$: −11.6° (C=1.0, MeOH)

IR (Neat): 3600–3100, 1735, 1626, 1275, 1129, 900 cm$^{-1}$

NMR (DMSO-d$_6$, δ): 2.20–5.20 (13H, m); 6.60–8.20 (13H, m); 10.85 (1H, br s)

MASS: 604 (M+1), 454

11) (2R)-4-(Benzyloxycarbonylmethyl)-2-(1H-indol-3-yl-methyl)-1-(3,5-dimethylbenzoyl)piperazine mp: 148°–150° C.

$[\alpha]_D^{21}$: +40.2° (C=0.5, DMF)

IR (Nujol): 3200, 1735, 1604, 1149, 734 cm$^{-1}$

NMR (DMSO-d$_6$, δ): 2.10–4.40 (17H, m); 5.13 (2H, s); 6.50–7.80 (13H, m); 10.85 (1H, s)

MASS: 496 (M+1)

12) (2R)-1-[3,5-Bis(trifluoromethyl)benzoyl]-4-[(4-fluorophenyl)carbonylmethyl]-2-(1H-indol-3-yl-methyl)piperazine mp: 95°–105° C.

$[\alpha]_D^{17}$: −21.2° (C=0.5, MeOH)

IR (Nujol): 3450–3100, 1628, 1595, 1277, 1130, 900 cm$^{-1}$

NMR (DMSO-d$_6$, δ): 2.20–4.95 (11H, m); 6.50–8.20 (12H, m); 10.81 (1H, s)

MASS: 592 (M+1)

13) (2R)-1-[3,5-Bis(trifluoromethyl)benzoyl]-2-(1H-indol-3-yl-methyl)-4-[4-(methoxycarbonyl)benzyl]piperazine mp: 75°–78° C.

$[\alpha]_D^{21}$: −40.8° (C=0.5, MeOH)

IR (Nujol): 3450–3100, 1716, 1625, 1277, 1170, 1130, 900 cm$^{-1}$

NMR (DMSO-d$_6$, δ): 2.00–5.00 (14H, m); 6.60–8.20 (12H, m); 10.79 (1H, s)

MASS: 604 (M+1)

14) (2R)-1-[3,5-Bis(trifluoromethyl)benzoyl]-2-(1H-indol-3-yl-methyl)-4-(4-nitrobenzyl)piperazine $[\alpha]_D^{21}$: −55.0° (C=0.5, DMF)

IR (Neat): 3300, 1625, 1516, 1340, 1275, 1170, 1128, 902 cm$^{-1}$

NMR (DMSO-d$_6$, δ) 2.00–5.00 (11H, m); 6.55–8.30 (12H, m); 10.79 (1H, s)

MASS: 591 (M+1), 456

15) (2R)-1-[3,5-Bis(trifluoromethyl)benzoyl]-2-(1H-indol-3-yl-methyl)-4-[4-(N,N-dimethylcarbamoyl)-benzyl]piperazine hydrochloride mp: 143°–155° C.

$[\alpha]_D^{21}$: −24.2° C. (C=0.5, DMF)

IR (Nujol): 3600–3100, 2750–2000, 1610, 1277, 1170, 1128, 900 cm$^{-1}$

NMR (DMSO-d$_6$, δ) 2.80–5.20 (17H, m); 6.50–8.25 (12H, m); 10.81 (1H, s); 11.40–11.80 (1H, m)

MASS: 617 (M+1) (free), 456

Example 31

The following compounds were obtained according to a similar manner to that of Example 16.

1) (2R)-4-(4-Amino-trans-cinnamoyl)-1-[3,5-bis(trifluoromethyl)benzoyl]-2-(1H-indol-3-yl-methyl)piperazine hydrochloride mp: 147°–155° C.

$[\alpha]_D^{22}$: −24.8° (C=1.0, MeOH)

IR (Nujol): 3600–3100, 2630–2100, 1635, 1510, 1277, 1175, 1130, 902 cm$^{-1}$

NMR (DMSO-d$_6$, δ) 2.75–5.20 (9H, m); 6.17–8.22 (16H, m); 10.90–11.10 (1H, m)

MASS: 601 (M+1) (free)

2) (2R)-1-[3,5-Bis(trifluoromethyl)benzoyl]-2-(3,4-dimethylbenzyl)-4-(4-methoxy-trans-cinnamoyl)piperazine mp: 67°–76° C.

$[\alpha]_D^{21}$: −9.4° (C=1.0, MeOH)

IR (Nujol): 1645, 1600, 1575, 1510, 1540, 1350, 1320 cm$^{-1}$

NMR (CDCl$_3$, δ): 2.14 and 2.22 (6H, 2 s); 2.6–5.3 (9H, m); 3.85 (3H, s); 6.5–7.7 (10H, m); 7.75 (1H, d, J=15.1 Hz); 7.89 (1H, br s)

MASS: 605 (M+1)

3) (2R)-1-[3,5-Bis(trifluoromethyl)benzoyl]-2-(3,4-dimethylbenzyl)-4-[3-(2-thienyl)-trans-acryloyl]piperazine
mp: 78°–80° C.
$[\alpha]_D^{21}$: +1.70 (C=1.0, MeOH)
IR (Nujol): 1635, 1600, 1500, 1350, 1330 cm$^{-1}$
NMR (CDCl$_3$, δ): 2.15 and 2.21 (6H, 2 s); 2.6–5.3 (9H, m); 6.4–7.7 (9H, m); 7.8–8.0 (2H, m)
MASS: 581 (M+1), 445

4) (2R)-1-[3,5-Bis(trifluoromethyl)benzoyl]-2-(1H-indol-3-yl-methyl)-4-[(2-pyrazinyl)carbonyl]piperazine dihydrochloride
mp: 92°–95° C.
$[\alpha]_D^{22}$: –2.60 (C=0.5, MeOH)
IR (Nujol): 3600–3100, 2750–2000, 1630, 1276, 1174, 1128, 900 cm$^{-1}$
NMR (DMSO-d$_6$, a) 2.80–5.20 (9H, m); 6.15–9.05 (11H, m); 10.78–10.92 (1H, m)
MASS: 562 (M+1) (free), 456

5) (2R)-1-[3,5-Bis(trifluoromethyl)benzoyl]-2-(1H-indol-3-yl-methyl)-4-[4-(dimethylamino)benzoyl]piperazine
IR (CHCl$_3$): 3250, 2990, 2900, 1602, 1522 cm$^{-1}$
NMR (DMSO-d$_6$, δ): 2.97 (6H, s); 2.58–3.60 (6H, m); 3.82–4.96 (3H, m); 6.54–8.26 (12H, m); 10.84 (1H, s)
MASS: 603 (M+1)

6) (2R)-1-[3,5-Bis(trifluoromethyl)benzoyl]-2-(1H-indol-3-yl-methyl)-4-(4-hydroxybenzoyl)piperazine
mp: >145° C.
IR (Nujol): 3330, 1638, 1600 cm$^{-1}$
NMR (DMSO-d$_6$, δ): 2.60–3.67 (6H, m); 3.82–4.99 (3H, m); 6.50–8.24 (12H, m); 9.90 (1H, s); 10.84 (1H, s)
MASS: 576 (M+1)

7) (2R)-4-(4-Acetoxybenzoyl)-1-[3,5-bis (trifluoromethyl) benzoyl]-2-(1H-indol-3-yl-methyl)piperazine
mp: 196°–197° C.
IR (Nujol): 3400, 1733, 1625 cm$^{-1}$
NMR (DMSO-d$_6$, a): 2.30 (3H, s); 3.00–5.05 (9H, m); 6.52–8.28 (12H, m); 10.83 (1H, s)
MASS: 618 (M+1)

8) (2R)-4-(4-Cyanobenzoyl)-1-[3,5-bis(trifluoromethyl)-benzoyl]-2-(1H-indol-3-yl-methyl)piperazine
mp: 205°–207° C.
IR (Nujol): 3260, 2220, 1626 cm$^{-1}$
NMR (DMSO-d$_6$, δ): 2.76–5.10 (9H, m); 6.44–8.25 (12H, m); 10.80 and 10.88 (1H, 2 s)
MASS: 585 (M+1)

9) (2R)-1-[3,5-Bis(trifluoromethyl)benzoyl]-2-(1H-indol-3-yl-methyl)-4-(4-acetylbenzoyl)piperazine
mp: 245°–248° C.
IR (Nujol): 3270, 1683, 1638, 1626, 1609 cm$^{-1}$
NMR (DMSO-d$_6$, a): 2.62 (3H, s); 2.80–5.08 (9H, m); 6.40–8.26 (12H, m); 10.76 and 10.89 (1H, 2 s)
MASS: 602 (M+1)

10) (2R)-1-[3,5-Bis(trifluoromethyl)benzoyl]-2-(3,4-dimethylbenzyl)-4-[3-(3-pyridyl)propionyl]piperazine
$[\alpha]_D^{18}$: –3.5° (C=1.0, MeOH)
IR (Neat): 1635, 1570, 1500, 1460, 1430 cm$^{-1}$
NMR (CDCl$_3$, δ): 2.19 and 2.21 (6H, 2 s); 2.5–3.5 (10H, m); 3.7–5.3 (3H, m); 6.5–7.5 (6H, m); 7.5–7.7 (1H, m); 7.8–7.9 (1H, m); 8.4–8.6 (2H, m)
MASS: 578 (M+1)

11) (2R)-1-(3,5-Dimethylbenzoyl)-2-(3,4-dimethylbenzyl)-4-[3-(3-pyridyl)-trans-acryloyl]piperazine
$[\alpha]_D^{18}$: +4.9° (C=0.5, MeOH)
IR (Neat): 3100–2800 (br), 1620, 1500, 1460, 1420, 1360, 1280 cm$^{-1}$
NMR (CDCl$_3$, δ): 2.0–2.4 (12H, m); 2.7–5.2 (9H, m); 6.5–7.1 (7H, m); 7.2–7.4 (1H, m); 7.6–7.9 (2H, m); 8.6–8.9 (2H, m)

MASS: 468 (M+1)

12) ($^2$R)-4-Benzoyl-1-[3,5-bis(trifluoromethyl)benzoyl]-2-(1H-indol-3-yl-methyl)piperazine
IR (Nujol): 3250, 1622 cm$^{-1}$
NMR (DMSO-d$_6$, δ) 2.80–5.05 (9H, m); 6.50–8.25 (13H, m); 10.84 (1H, s)
MASS: 560 (M+1)

13) ($^2$R)-1-[3,5-Bis(trifluoromethyl)benzoyl]-2-(1H-indol-3-yl-methyl)-4-(4-nitrobenzoyl)piperazine
mp: 151°–153° C.
IR (Nujol): 3330, 1653, 1626, 1520 cm$^{-1}$
NMR (DMSO-d$_6$, δ): 2.20–5.10 (9H, m); 6.40–8.40 (12H, m); 10.77 and 10.91 (1H, 2 s)
MASS: 605 (M+1)

14) (2R)-4-(2-Chloroacetyl)-1-[3,5-bis(trifluoromethyl)-benzoyl]-2-(3,4-dimethylbenzyl)piperazine
IR (Neat): 1645, 1500, 1430, 1370, 1355, 1340, 1320 cm$^{-1}$ 15) ($^2$R)-4-(trans-Cinnamoyl)-1-[3,5-bis(trifluoromethyl)-benzoyl]-2-[(1R)-1-(N-methyl-1H-indol-3-yl)ethyl]-piperazine
mp: 90°–91° C.
$[\alpha]_D^{24}$: +0.6° (C=0.5, MeOH)
IR (Nujol): 1640, 1600, 1450, 1380, 1350 cm$^{-1}$
NMR (CDCl$_3$, δ): 1.4–1.7 (3H, m); 2.5–5.3 (8H, m); 3.69 (3H, s); 6.6–7.9 (15H, m)
MASS: 614 (M+1)

16) (2R)-4-(trans-Cinnamoyl)-2-(3,4-dichlorobenzyl)-1-[3,5-bis(trifluoromethyl)benzoyl]piperazine
mp: 83°–86° C.
$[\alpha]_D^{24}$: +8.2° (C=1.0, MeOH)
IR (Nujol): 1640, 1605, 1430, 1350, 1320 cm$^{-1}$
NMR (CDCl$_3$, δ): 2.8–3.2 (4H, m); 3.3–3.6 (3H, m); 3.8–5.2 (2H, m); 6.6–7.7 (11H, m); 7.79 (1H, d, J=15.3 Hz); 7.95 (1H, br s)
MASS: 615 (M+1)

17) (2R)-4-(2,2,2-Trifluoroacetyl)-1-[3,5-bis(trifluoromethyl)benzoyl]-2-(1H-indol-3-yl-methyl)piperazine
mp: 197.6°–198.8° C.
IR (Nujol): 3300, 1690, 1628, 1610 cm$^{-1}$
NMR (DMSO-d$_6$, δ): 2.60–5.20 (9H, m); 6.50–8.25 (8H, m); 10.88 (1H, s)
MASS: 552 (M+1)

18) (2R)-1-[3,5-Bis(trifluoromethyl)benzoyl]-4-cyclohexylcarbonyl-2-(1H-indol-3-yl-methyl)piperazine
mp: 200°–201° C.
$[\alpha]_D^{22}$: –3.8° (C=1.0, MeOH)
IR (Nujol): 3340, 1630, 1617, 1272, 1184, 1136, 902 cm$^{-1}$
NMR (DMSO-d$_6$, δ): 1.00–1.95 (10H, m); 2.40–5.20 (10H, m); 6.55–8.25 (8H, m); 10.80–11.00 (1H, m)
MASS: 566 (M+1)

19) (2R)-4-(2-Chloroacetyl)-1-[3,5-bis(trifluoromethyl)-benzoyl]-2-(1H-indol-3-yl-methyl)piperazine
mp 185°–187° C.
$[\alpha]_D^{22}$: –0.1° (C=1.0, MeOH)
IR (Nujol): 3280, 1660, 1630, 1279, 1225, 1190, 1125, 905, 750 cm$^{-1}$
NMR (DMSO-d$_6$, δ): 2.70–5.10 (11H, m); 6.55–8.20 (8H, m); 10.90 (1H, s)
MASS: 532 (M+1), 456

20) (2R)-4-(3,4-Difluoro-trans-cinnamoyl)-1-[3,5-bis (trifluoromethyl)benzoyl]-2-(1H-indol-3-yl-methyl)piperazine
mp: 214°–217° C.
$[\alpha]_D^{21}$: –30.6° C. (C=1.0, MeOH)
IR (Nujol): 3270, 1625, 1607, 1511, 1276, 1131, 900 cm$^{-1}$ NMR (DMSO-d$_6$, δ) 2.70–5.20 (9H, m); 6.60–8.25 (13H, m); 10.85 (1H, br s)
MASS: 622 (M+1)

21) (2R)-4-(4-Acetylamino-trans-cinnamoyl)-1-[3,5-bis(trifluoromethyl)benzoyl]-2-(1H-indol-3-yl-methyl) piperazine
mp: 148°–154° C.
IR (Nujol): 3600–3100, 1637, 1590, 1278, 1175, 1133, 900 cm$^{-1}$
NMR (DMSO-d$_6$, δ): 2.06 (3H, s); 2.75–5.20 (9H, m); 6.60–8.25 (12H, m); 10.10 (1H, s); 10.87 (1H, br s)
MASS: 643 (M+1)

Example 32

The following compounds were obtained according to a similar manner to that of Example 27.

1) (2R)-1-[3,5-Bis(trifluoromethyl)benzoyl]-2-(1H-indol-3-yl-methyl)-4-[N-(l-pyrrolyl)carbamoylmethyl]-piperazine dihydrochloride
mp: 190°–195° C.
[α]$_D$$^{21}$: –18.6° (C=0.5, DMF)
IR (Nujol): 3630–3060, 2750–2100, 1700, 1635, 1278, 1175, 1131, 900 cm$^{-1}$
NMR (DMSO-d$_6$, δ): 2.70–5.20 (11H, m); 6.00–8.30 (13H, m); 10.95 (1H, s); 11.00–12.10 (2H, m)
MASS: 578 (M+1) (free), 456

2) (2R)-1-[3,5-Bis(trifluoromethyl)benzoyl]-2-(1H-indol-3-yl-methyl)-4-[N-methyl-N-(2-dimethylaminoethyl)-carbamoylmethyl]piperazine dihydrochloride
mp: 200°–205° C.
[α]$_D$$^{22}$: –20.2° (C=0.5, DMF)
IR (Nujol): 3340, 3180, 2670, 1655, 1275, 1195, 1129, 908 cm$^{-1}$
NMR (DMSO-d$_6$, δ): 2.60–5.10 (24H, m); 6.60–8.30 (8H, m); 10.00–10.90 (2H, m); 11.00 (1H, s)
MASS: 598 (M+1) (free)

3) (2R)-1-[3,5-Bis(trifluoromethyl)benzoyl]-2-(1H-indol-3-yl-methyl)-4-[N-(2-piperidinoethyl)-carbamoylmethyl]piperazine dihydrochloride
mp: 194°–201° C.
[α]$_D$$^{22}$: –9.6° (C=0.5, DMF)
IR (Nujol): 3680–3100, 2750–1970, 1680, 1635, 1274, 1170, 1125, 902 cm$^{-1}$
NMR (DMSO-d$_6$, δ): 0.80–5.15 (25H, m); 6.80–8.25 (9H, m); 8.95–9.25 (1H, m); 10.40–10.60 (1H, br s); 11.00 (1H, s)
MASS: 624 (M+1) (free)

4) (2R)-1-[3,5-Bis(trifluoromethyl)benzoyl]-2-(1H-indol-3-yl-methyl)-4-[N-[2-(l-pyrrolidino)ethyl]-carbamoylmethyl] piperazine dihydrochloride
mp: 183°–190° C.
[α]$_D$$^{22}$: –9.4° (C=0.5, DMF)
IR (Nujol): 3700–3100, 2750–1955, 1683, 1635, 1273, 1170, 1123, 900 cm$^{-1}$
NMR (DMSO-d$_6$, δ): 1.80–5.10 (23H, m); 6.60–8.30 (9H, m); 8.90–9.15 (1H, m); 10.75–10.95 (1H, m); 10.98 (1H, s)
MASS: 610 (M+1) (free), 456

5) (2R)-4-[N-(Benzyloxy)carbamoylmethyl-1-[3,5-bis(trifluoromethyl) benzoyl]-2-(1H-indol-3-yl-methyl) piperazine hydrochloride
mp: 161°–167° C.
[α]$_D$$^{24}$: –16.6° (C=0.5, DMF)
IR (Nujol) 3600–3000, 2750–2000, 1685, 1635, 1277, 1173, 1130, 900 cm$^{-1}$
NMR (DMSO-d$_6$, δ): 3.00–5.20 (13H, m); 6.60–8.30 (14H, m); 11.01 (1H, s); 11.60–12.05 (1H, m)
MASS: 619 (M+1) (free), 456

6) (2R)-1-[3,5-Bis(trifluoromethyl)benzoyl]-2-(3,4-dimethylbenzyl)-4-[N-(3-pyridyl)carbamoylmethyl]-piperazine dihydrochloride
mp: 115°–122° C. (dec.)
[α]$_D$$^{18}$: –34.1° (C=0.5, MeOH)
IR (Neat): 3300, 3000–2400, 1635, 1560, 1430 cm$^{-1}$
NMR (DMSO-d$_6$, δ): 2.11 and 2.18 (6H, 2 s); 2.7–5.8 (13H, m); 6.5–7.8 (5H, m); 7.94 (1H, dd, J=8.3 Hz and 5.2 Hz); 8.18 (1H, br s); 8.52 (1H, d, J=8.3 Hz); 8.61 (1H, d, J=5.2 Hz); 9.16 (1H, d, J=2.0 Hz); 12.1–12.4 (1H, m)
MASS: 579 (M+1) (free)

7) (2R)-4-(Hydrazinocarbonylmethyl)-1-[3,5-bis(trifluoromethyl) benzoyl]-2-(1H-indol-3-yl-methyl) piperazine dihydrochloride
mp: 204°–209° C.
[α]$_D$$^{24}$: –19.4° (C=0.5, DMF)

8) (2R)-4-[N-[3-(Diethylamino)propyl]carbamoylmethyl]-1-[3,5-bis(trifluoromethyl)benzoyl]-2-(1H-indol-3-yl-methyl)piperazine dihydrochloride
mp: 159°–170° C.
[α]$_D$$^{26}$: –6.2° (C=0.5, DMF)
IR (Nujol): 3650–3100, 2750–1950, 1635, 1276, 1171, 1130, 900 cm$^{-1}$
NMR (DMSO-d$_6$, δ): 1.15–1.30 (8H, m); 3.00–5.15 (19H, m); 6.60–8.30 (9H, m); 8.90–9.15 (1H, m); 10.40–10.70 (1H, m); 11.00–11.10 (1H, m)
MASS: 626 (M+1) (free)

9) (2R)-1-[3,5-Bis(trifluoromethyl)benzoyl]-2-(1H-indol-3-yl-methyl)-4-(N,N-dimethylcarbamoylmethyl)-piperazine hydrochloride
mp: 165° 168° C.
[α]$_D$$^{22}$: –29.0° (C =0.5, MeOH)
IR (Nujol): 3600–3100, 2700–2100, 1650, 1278, 1174, 1130, 902 cm$^{-1}$
NMR (DMSO-d$_6$, δ): 2.60–5.15 (17H, m); 6.80–8.25 (8H, m); 10.10–10.40 (1H, m); 11.01 (1H, s)
MASS: 541 (M+1) (free)

10) (2R)-4-[2-(N-Benzyl-N-methylamino)acetyl]-1-[3,5-bis(trifluoromethyl)benzoyl]-2-(1H-indol-3-yl-methyl) piperazine hydrochloride
mp: 157°–165° C.
[α]$_D$$^{22}$: –8.3° (C=1.0, MeOH)
IR (Nujol): 3650–3100, 2750–2000, 1635, 1277, 1175, 1130, 902 cm$^{-1}$
NMR (DMSO-d$_6$, δ): 2.70–5.20 (16H, m); 6.60–8.25 (13H, m); 10.00–10.25 (1H, m); 10.97 (1H, br s)
MASS: 617 (M+1) (free), 456

11) (2R)-4-(Carbamoylmethyl)-1-(3,5-dimethylbenzoyl)-2-(3,4-dimethylbenzyl)piperazine hydrochloride
mp: 152–160° C. (dec.)
[α]$_D$$^{18}$: +3.1° (C=0.5, MeOH)
IR (Nujol): 3300 (br), 3150, 1685, 1625, 1595, 1500, 1510 cm$^{-1}$
NMR (DMSO-d$_6$, δ): 2.1–2.4 (12H, m); 2.7–5.2 (12H, m); 6.4–8.2 (8H, m)
MASS: 394 (M+1) (free), 337

12) (2R)-4-(3-Carbamoylpropyl)-1-[3,5-bis(trifluoromethyl)benzoyl]-2-(1H-indol-3-yl-methyl) piperazine hydrochloride
mp: 165°–170° C.
IR (Nujol): 3670–3050, 2750–2000, 1635, 1275, 1171, 1128, 903 cm$^{-1}$
NMR (DMSO-d$_6$, δ): 1.80–5.20 (15H, m); 6.60–8.30 (10H, m); 10.95 (1H, s); 11.22 (1H, br s)
MASS: 541 (M+1) (free), 457

13) (2R)-4-(Carbamoylmethyl)-1-(3,5-dimethylbenzoyl)-2-(1H-indol-3-yl-methyl)piperazine mp: >225° C.
[α]$_D^{21}$: +41.0° (C=0.5, DMF)
IR (Nujol): 3410, 3200, 1674, 1610, 1220, 750 cm$^{-1}$
NMR (DMSO-d$_6$, δ): 2.16 (6H, s); 2.50 (2H, s); 2.60-5.00 (9H, m); 6.50–7.85 (10H, m); 10.81 (1H, s)
MASS: 405 (M+1)

14) (2R)-1-[3,5-Bis(trifluoromethyl)benzoyl]-2-(1H-indol-3-yl-methyl)-4-[N-(4-methyl-1-piperazinyl)carbamoylmethyl]piperazine dihydrochloride pentahydrate
mp: 212°–216° C.
[α]$_D^{29}$: −13.0° (C=0.5, MeOH)
IR (Nujol): 3650–3100, 2750–2000, 1685, 1632, 1276, 1176, 1131, 900 cm$^{-1}$
NMR (DMSO-d$_6$, δ): 2.40–5.10 (22H, m); 6.60–8.30 (9H, m); 9.62 (1H, S); 10.20–10.60 (1H, m); 11.01 (1H, s); 11.00–11.30 (1H, m)
MASS: 611 (M+1) (free)

15) (2R)-4-[N-(2-Diethylaminoethyl)carbamoylmethyl]-1-3,5-bis(trifluoromethyl)benzoyl]-2-(1H-indol-3-yl-methyl)piperazine dihydrochloride
mp: 176°–179° C.
[α]$_D^{19}$: −8.4° (C=0.5, DMF)
IR (Nujol): 3650–3100, 2750–2000, 1681, 1635, 1275, 1173, 1130, 901 cm$^{-1}$
NMR (DMSO-d$_6$, δ): 1.20–1.30 (6H, m); 2.70–5.20 (19H, m); 6.60–8.30 (9H, m); 9.09 (1H, br s); 10.60 (1H, br s); 10.99 (1H, s)
MASS: 612 (M+1) (free)

16) (2R)-1-[3,5-Bis(trifluoromethyl)benzoyl]-2-(1H-indol-3-yl-methyl)-4-[N-(isopropyl)carbamoylmethyl]-piperazine
mp: 130°–134°C.
[α]$_D^{18}$: −12.6° (C=0.5, DMF)
IR (Nujol): 3500–3100, 1678, 1626, 1277, 1168, 1126, 900 cm$^{-1}$
NMR (DMSO-d$_6$, δ): 1.09 (6H, d, J=6.5 Hz); 2.10–5.00 (12H, m); 6.60–8.20 (9H, m); 10.85 (1H, s)
MASS: 555 (M+1)

17) (2R)-4-[N-(Benzyloxycarbonylmethyl)carbamoylmethyl]-1-[3,5-bis(trifluoromethyl)benzoyl]-2-(1H-indol-3-yl-methyl)piperazine
mp: 90°–93° C.
[α]$_D^{20}$: −13.6° (C=0.5, MeOH)
IR (Nujol): 3600–3100, 1739, 1662, 1628, 1510, 1277, 1130, 900 cm$^{-1}$
NMR (DMSO-d$_6$, δ): 2.20–5.20 (15H, m); 6.60–8.35 (14H, m); 10.84 (1H, s)
MASS: 661 (M+1)

18) (2R)-1-[3,5-Bis(trifluoromethyl)benzoyl]-2-(1H-indol-3-yl-methyl)-4-[N-(2-dimethylaminoethyl)-carbamoylmethyl]piperazine
mp: 123° 125° C.
[α]$_D^{19}$: −12.6° (C=0.5, MeOH)
IR (Nujol): 3400–3100, 1659, 1630, 1510, 1279, 1126, 900 cm$^{-1}$
NMR (DMSO-d$_6$, δ): 2.16 (6H, s); 2.30–5.00 (15H, m); 6.60–8.20 (9H, m); 10.86 (1H, s)
MASS: 584 (M+1)

19) (2R)-1-[3,5-Bis(trifluoromethyl)benzoyl]-2-(1H-indol-3-yl-methyl)-4-[N-(3-pyridylmethyl)carbamoylmethyl]-piperazine
mp: 105°–109° C.
[α]$_D^{19}$: −26.5° (C=0.5, MeOH)
IR (Nujol): 3600–3100, 1628, 1510, 1275, 1130, 900 cm$^{-1}$
NMR (DMSO-d$_6$, δ): 2.10–5.00 (13H, m); 6.60–8.60 (13H, m); 10.84 (1H, s)
MASS: 604 (M+1)

20) (2R)-4-[N-(4-Fluorobenzyl)carbamoylmethyl]-1-[3,5-bis(trifluoromethyl)benzoyl]-2-(1H-indol-3-yl-methyl)piperazine
mp: 94°–97° C.
[α]$_D^{20}$: −34.4° (C=0.5, MeOH)
IR (Nujol): 3600–3100, 1628, 1509, 1276, 1130, 900 cm$^{-1}$
NMR (DMSO-d$_6$, δ): 2.15–5.20 (13H, m); 6.60–8.50 (13H, m); 10.84 (1H, s)
MASS: 621 (M+1), 456

21) (2R)-4-[N-(Cyclohexylmethyl)carbamoylmethyl]-1-[3,5-bis(trifluoromethyl)benzoyl]-2-(1H-indol-3-yl-methyl)piperazine
mp: 100°–103° C.
[α]$_D^{21}$: −17.6° (C=0.5, MeOH)
IR (Nujol): 3500–3100, 1630, 1522, 1276, 1170, 1130, 898 cm$^{-1}$
NMR (DMSO-d$_6$, δ): 0.80–2.40 (13H, m); 2.60–5.20 (11H, m); 6.60–8.20 (9H, m); 10.86 (1H, s)
MASS: 609 (M+1), 456

22) (2R)-1-[3,5-Bis(trifluoromethyl)benzoyl]-2-(1H-indol-3-yl-methyl)-4-[N-(2-methoxyethyl)carbamoylmethyl]-piperazine hydrochloride
[α]$_D^{21}$: −7.2° (C=0.5, DMF)
IR (Nujol): 3700–3100, 2700–2000, 1720–1590, 1271, 1120, 900 cm$^{-1}$
NMR (DMSO-d$_6$, δ): 2.70–5.10 (18H, m); 6.60–8.90 (9H, m); 10.98 (1H, s)
MASS: 571 (M+1) (free)

23) (2R)-1-[3,5-Bis(trifluoromethyl)benzoyl]-4-[N-(2-hydroxyethyl)carbamoylmethyl]-2-(1H-indol-3-yl-methyl)piperazine hydrochloride
mp: 150°–160° C.
IR (Nujol): 3600–3100, 2700–2100, 1670, 1635, 1276, 1173, 1130, 900 cm$^{-1}$
NMR (DMSO-d$_6$, δ): 2.70–5.10 (16H, m); 6.60–8.80 (9H, m); 10.97 (1H, s)
MASS: 557 (M+1) (free), 456

24) (2R)-1-[3,5-Bis(trifluoromethyl)benzoyl]-2-(1H-indol-3-yl-methyl)-4-[N-(dimethylamino)carbamoylmethyl]-piperazine
mp: 115°–125° C.
[α]$_D^{17}$: −5.0° (C=0.5, DMF)
IR (Nujol): 3600–3100, 1670, 1625, 1277, 1170, 1130, 900 cm$^{-1}$
NMR (DMSO-d$_6$, δ): 2.10–5.00 (17H, m); 6.60–8.75 (9H, m); 10.85 (1H, s)
MASS: 556 (M+1)

25) (2R)-1-[3,5-Bis(trifluoromethyl)benzoyl]-4-[[4-(2-hydroxyethyl)-1-piperazinyl]carbonylmethyl]-2-(1H-indol-3-yl-methyl)piperazine dihydrochloride
mp: 199°–208° C.
[α]$_D^{19}$: −25.4° (C=0.5, DMF)
IR (Nujol): 3650–3050, 2750–2000, 1645, 1275, 1173, 1128, 900 cm$^{-1}$
NMR (DMSO-d$_6$, δ): 2.90–5.20 (24H, m); 6.60–8.30 (8H, m); 10.30–10.80 (1H, m); 11.00 (1H, s); 11.00–11.35 (1H, br s)
MASS: 626 (M+1) (free)

26) (2R)-1-[3,5-Bis(trifluoromethyl)benzoyl]-2-(1H-indol-3-yl-methyl)-4-[[4-(2-pyridyl)-1-piperazinyl]-carbonylmethyl]piperazine trihydrochloride
mp: 190°–200° C.
IR (Nujol) 3650–3050, 2750–1980, 1635, 1272, 1170, 1122, 900 cm$^{-1}$
NMR (DMSO-d$_6$, δ): 3.00–5.20 (19H, m); 6.20–8.30 (12H, m); 11.02 (1H, s)
MASS: 659 (M+1) (free), 456

27) (2R)-4-[(4-Acetyl-1-piperazinyl)carbonylmethyl]-1-[3,5-bis(trifluoromethyl)benzoyl]-2-(1H-indol-3-yl-methyl)piperazine hydrochloride mp: 180°–190° C.
[α]$_D^{19}$: −31.6° (C=0.5, DMF)
IR (Nujol): 3650–3100, 2750–2000, 1635, 1278, 1172, 1130, 900 cm$^{-1}$
NMR (DMSO-d$_6$, δ): 2.05 (3H, s); 3.00–5.20 (19H, m); 6.60–8.30 (8H, m); 10.20–10.60 (1H, m); 11.01 (1H, s)
MASS: 624 (M+1) (free)

28) (2R)-1-[3,5-Bis(trifluoromethyl)benzoyl]-2-(1H-indol-3-yl-methyl)-4-[(4-phenyl-1-piperazinyl)-carbonylmethyl]piperazine dihydrochloride
mp: 190°–200° C.
[α]$_D^{22}$: −30.6° (C=0.5, DMF)
IR (Nujol): 3650–3100, 2750–2000, 1640, 1279, 1172, 1130, 900 cm$^{-1}$
NMR (DMSO-d$_6$, δ): 2.70–5.30 (19H, m); 6.60–8.30 (13H, m); 10.50–10.70 (1H, m); 11.03 (1H, s)
MASS: 658 (M+1) (free)

29) (2R)-1-[3,5-Bis(trifluoromethyl)benzoyl]-2-(1H-indol-3-yl-methyl)-4-[(4,1'-bipiperidin-1-yl)carbonylmethyl]piperazine dihydrochloride
mp: 209°–220° C.
[α]$_D^{24}$: −31.6° (C=0.5, DMF)
IR (Nujol): 3680–3050, 2750–1990, 1640, 1274, 1170, 1127, 900 cm$^{-1}$
NMR (DMSO-d$_6$, δ): 1.20–5.20 (30H, m); 6.60–8.25 (8H, m); 10.20–10.50 (1H, m); 11.02 (2H, br s)
MASS: 664 (M+1) (free)

30) (2R)-1-[3,5-Bis(trifluoromethyl)benzoyl]-2-(1H-indol-3-yl-methyl)-4-[(4-cyclohexyl-1-piperazinyl)-carbonylmethyl]piperazine dihydrochloride
mp: 207°–220° C.
[α]$_D^{22}$: −24.0° (C=0.5, DMF)
IR (Nujol): 3650–3050, 2750–2000, 1650, 1278, 1172, 1131, 900 cm$^{-1}$
NMR (DMSO-d$_6$, δ): 1.00–5.10 (30H, m); 6.60–8.25 (8H, m); 10.40–10.80 (1H, m); 10.99 (1H, s); 11.62 (1H, br s)
MASS: 664 (M+1) (free), 456

31) (2R)-1-[3,5-Bis(trifluoromethyl)benzoyl]-2-(1H-indol-3-yl-methyl)-4-[(4-propyl-1-piperazinyl)-carbonylmethyl]piperazine dihydrochloride
mp: 206°–214° C.
[α]$_D^{22}$: −25.4° (C=0.5, DMF)
IR (Nujol): 3650–3100, 2750–1980, 1640, 1278, 1173, 1130, 900 cm$^{-1}$
NMR (DMSO-d$_6$, δ): 0.92 (3H, t, J=7.2 Hz); 1.65–5.20 (23H, m); 6.60–8.25 (8H, m); 10.99 (1H, s); 11.45–11.70 (1H, m)
MASS: 624 (M+1) (free)

32) (2R)-4-[((2S)-2-Carbamoyl-1-pyrrolidino)-carbonylmethyl]-1-[3,5-bis(trifluoromethyl)benzoyl]-2-(1H-indol-3-yl-methyl)piperazine hydrochloride
mp: 196°–203° C.
[α]$_D^{24}$: −50.6° (C=0.5, DMF)
IR (Nujol): 3600–3050, 2750–2000, 1650, 1277, 1171, 1130, 900 cm$^{-1}$
NMR (DMSO-d$_6$, δ): 1.80–5.20 (18H, m); 6.60–8.30 (10H, m); 10.20–11.00 (1H, m); 11.02 (1H, s)
MASS: 610 (M+1) (free)

33) (2R)-4-[(4-Acetylamino-4-phenylpiperidino)-carbonylmethyl]- 1-[3,5-bis(trifluoromethyl)benzoyl]-2-(1H-indol-3-yl-methyl)piperazine hydrochloride
mp: 210°–219° C.
[α]$_D^{24}$: −25.0° (C=0.5, DMF)
IR (Nujol): 3600–3100, 2700–2000, 1645, 1278, 1173, 1130, 900 cm$^{-1}$
NMR (DMSO-d$_6$, δ): 1.60–5.15 (22H, m); 6.60–8.25 (14H, m); 10.00–10.30 (1H, m); 11.01 (1H, s)
MASS: 714 (M+1) (free)

34) (2R)-4-[(4-Ethoxycarbonylpiperidino)carbonylmethyl]-1-[3,5-bis(trifluoromethyl)benzoyl]-2-(1H-indol-3-yl-methyl)piperazine
[α]$_D^{23}$: −11.4° (C=0.5, DMF)
IR (Neat): 3260, 1724, 1630, 1276, 1174, 1128, 900 cm$^{-1}$
NMR (DMSO-d$_6$, δ): 1.18 (3H, t, J=7.1 Hz); 1.20–5.00 (22H, m); 6.60–8.20 (8H, m); 10.87 (1H, m)
MASS: 653 (M+1)

35) (2R)-1-[3,5-Bis(trifluoromethyl)benzoyl]-2-(1H-indol-3-yl-methyl)-4-[(4-piperidon-1-yl)carbonylmethyl]-piperazine hydrochloride
mp: 160°–170° C.
[α]$_D^{26}$: −28.6° (C=0.5, DMF)
IR (Nujol): 3600–3100, 2750–2000, 1710, 1650, 1278, 1175, 1130, 900 cm$^{-1}$
NMR (DMSO-d$_6$, δ): 2.30–5.20 (19H, m); 6.60–8.30 (8H, m); 10.20–10.60 (1H, m); 11.02 (1H, s)
MASS: 595 (M+1) (free)

36) (2R)-4-[(3-Carbamoylpiperidino)carbonylmethyl]-1-[3,5-bis(trifluoromethyl)benzoyl]-2-(1H-indol-3-yl-methyl)piperazine hydrochloride
mp: 189°–196° C.
IR (Nujol): 3600–3100, 2750–2000, 1640, 1277, 1170, 1130, 900 cm$^{-1}$
NMR (DMSO-d$_6$, δ): 1.20–5.15 (20H, m); 6.60–8.30 (10H, m); 10.00–10.30 (1H, br s); 11.00 (1H, s)
MASS: 624 (M+1) (free)

37) (2R)-4-[(4-Acetylamino-4-phenylpiperidino)-carbonylmethyl]-1-[3,5-bis(trifluoromethyl)benzoyl]-2-(3,4-dimethylbenzyl)piperazine
mp: 158°–165° C. (dec.)
[α]$_D^{18}$: −14.6° (C=0.5, MeOH)
IR (Nujol): 3300, 1630, 1540, 1360 cm$^{-1}$
NMR (CDCl$_3$, δ): 2.02 (3H, s); 1.8–2.5 (11H, m); 2.6–5.2 (14H, m); 5.66 (1H, br s); 6.5–6.7 (1H, m); 6.9–7.5 (9H, m); 7.82 (1H, br s)
FABMASS: 703 (M+1), 644, 457, 414

38) (2R)-1-[3,5-Bis(trifluoromethyl)benzoyl]-2-(3,4-dimethylbenzyl)-4-(morpholinocarbonylmethyl)-piperazine hydrochloride
mp: 100°–125° C. (dec.)
[α]$_D^{18}$: −20.8° (C=0.5, MeOH)
IR (Nujol): 3300 (br), 2700–2500, 1650, 1450, 1360 cm$^{-1}$
NMR (DMSO-d$_6$, δ): 2.11 and 2.18 (6H, 2 s); 2.7–5.2 (19H, m); 6.6–7.3 (3H, m); 7.3–7.8 (2H, m); 8.1–8.3 (1H, m); 10.0–10.4 (1H, br m)
MASS: 572 (M+1) (free), 445

39) (2R)-4-[2-(4-Acetylamino-4-phenylpiperidino)acetyl]-1-[3,5-bis(trifluoromethyl)benzoyl]-2-(3,4-dimethylbenzyl)piperazine
mp: 120°–130° C. (dec.)
[α]$_D^{18}$: −7.4° (C=0.1, MeOH)
IR (Nujol): 3300, 1630, 1540, 1380, 1320, 1280 cm$^{-1}$
NMR (CDCl$_3$, δ): 2.01 (3H, s); 2.17 and 2.21 (6H, 2 s); 2.0–5.3 (19H, m); 5.53 (1H, d, J=6.2 Hz); 6.6–7.5 (10H, m); 7.84 (1H, s)
FABMASS: 703 (M+1), 642, 514, 414

40) (2R)-4-[(4-Carbamoylpiperidino)carbonylmethyl]-1-[3,5-bis(trifluoromethyl)benzoyl]-2-(1H-indol-3-yl-methyl)piperazine hydrochloride
mp: 197°–208° C.
[α]$_D^{20}$: −29.6° (C=0.5, DMF)
IR (Nujol): 3650–3050, 2750–2000, 1640, 1275, 1173, 1130, 900 cm$^{-1}$
NMR (DMSO-d$_6$, δ): 1.20–5.10 (20H, m); 6.60–8.25 (10H, m); 9.80–10.20 (1H, m); 10.97 (1H, s)

MASS: 624 (M+1) (free)

41) (2R)-1-[3,5-Bis(trifluoromethyl)benzoyl]-2-(1H-indol-3-yl-methyl)-4-[(4-methyl-1-homopiperazinyl)-carbonymethyl]piperazine dihydrochloride
mp: 220°–225° C. (dec.)
$[\alpha]_D^{21}$: −24.8° (C=0.5, DMF)
IR (Nujol): 3700–3100, 2750–1980, 1640, 1275, 1172, 1126, 903 cm$^{-1}$
NMR (DMSO-d$_6$, δ): 0.75–1.30 (2H, m); 2.00–5.20 (22H, m); 6.60–8.30 (8H, m); 10.50 (1H, br s); 11.01 (1H, s); 11.45 (1H, br s)
MASS: 610 (M+1) (free)

42) (2R)-4-[(4-Ethyl-1-piperazinyl)carbonylmethyl]-1-[3,5-bis(trifluoromethyl)benzoyl]-2-(1H-indol-3-yl-methyl)piperazine dihydrochloride
mp: 205°–211° C.
$[\alpha]_D^{19}$: −27.6° (C=0.5, DMF)
IR (Nujol): 3600–3100, 2700–2000, 1650, 1276, 1172, 1130, 900 cm$^{-1}$
NMR (DMSO-d$_6$, δ): 1.29 (3H, t, J=7.2 Hz); 2.80–5.20 (21H, m); 6.60–8.30 (8H, m); 11.00 (1H, s); 11.60–11.80 (1H, m)
MASS: 610 (M+1) (free)

43) (2R)-1-[3,5-Bis(trifluoromethyl)benzoyl]-2-(1H-indol-3-yl-methyl)-4-(piperidinocarbonylmethyl)piperazine hydrochloride
mp: 180°–190° C.
$[\alpha]_D^{19}$: −26.8° (C=0.5, DMF)
IR (Nujol): 3600–3100, 2700–2100, 1647, 1278, 1173, 1131, 900 cm$^{-1}$
NMR (DMSO-d$_6$, δ): 1.40–1.70 (6H, m); 3.10–5.20 (15H, m); 6.60–8.30 (8H, m); 10.00–10.40 (1H, m); 11.00 (1H, s)
MASS: 581 (M+1) (free)

44) (2R)-1-[3,5-Bis(trifluoromethyl)benzoyl]-2-(1H-indol-3-yl-methyl)-4-[(4-phenylpiperidino)carbonylmethyl]-piperazine hydrochloride
mp: 167°–173° C.
$[\alpha]_D^{19}$: −30.8° (C=0.5, DMF)
IR (Nujol): 3600–3100, 2700–2000, 1640, 1276, 1172, 1130, 900 cm$^{-1}$
NMR (DMSO-d$_6$, δ): 1.20–5.20 (20H, m); 6.60–8.30 (13H, m); 10.00–10.40 (1H, m); 11.00 (1H, s)
MASS: 657 (M+1) (free)

45) (2R)-4-[(4-Benzylpiperidino)carbonylmethyl]-1-[3,5-bis(trifluoromethyl)benzoyl]-2-(1H-indol-3-yl-methyl)piperazine hydrochloride
mp: 158°–160° C.
$[\alpha]_D^{19}$: −27.2° (C=0.5, DMF)
IR (Nujol): 3600–3100, 2700–2000, 1640, 1276, 1174, 1130, 900 cm$^{-1}$
NMR (DMSO-d$_6$, δ): 1.00–5.20 (22H, m); 6.60–8.30 (13H, m); 9.90–10.40 (1H, m); 10.99 (1H, s)
MASS: 671 (M+1) (free)

46) (2R)-1-[3,5-Bis(trifluoromethyl)benzoyl]-2-(1H-indol-3-yl-methyl)-4-(pyrrolidinocarbonylmethyl)piperazine hydrochloride
mp: 161°–166° C.
IR (Nujol): 3700–3100, 2700–2000, 1640, 1278, 1131, 902 cm$^{-1}$
NMR (DMSO-d$_6$, δ): 1.80–2.00 (4H, m); 3.00–5.20 (15H, m); 6.60–8.30 (8H, m); 11.00 (1H, s)
MASS: 567 (M+1) (free)

47) (2R)-1-[3,5-Bis(trifluoromethyl)benzoyl]-2-(1H-indol-3-yl-methyl)-4-[(4-methyl-1-piperazinyl)-carbonylmethyl]piperazine
mp: 105°–108° C.
$[\alpha]_D^{18}$: −12.2° (C=0.5, DMF)
IR (Nujol): 3600–3100, 1630, 1275, 1165, 1130, 900 cm$^{-1}$
NMR (DMSO-d$_6$, δ): 2.10–5.00 (22H, m); 6.60–8.20 (8H, m); 10.87 (1H, s)
MASS: 596 (M+1)

48) (2R)-4-(4-Carbamoylbenzyl)-1-[3,5-bis(trifluoromethyl)benzoyl]-2-(1H-indol-3-yl-methyl)piperazine
mp: 120°–126° C.
$[\alpha]_D^{21}$: −37.6° (C=0.5, DMF)
IR (Nujol): 3600–3100, 1660, 1610, 1276, 1170, 1130, 900 cm$^{-1}$
NMR (DMSO-d$_6$, δ): 2.00–5.00 (11H, m); 6.50–8.30 (14H, m); 10.80 (1H, s)
MASS: 589 (M+1)

49) (2R)-4-[N-(Carbamoylmethyl)carbamoylmethyl]-1-[3,5-bis(trifluoromethyl)benzoyl]-2-(1H-indol-3-yl-methyl)piperazine
mp: 135°–145° C.
$[\alpha]_D^{21}$: 15.0° (C=0.5, MeOH)
IR (Nujol): 3600–3100, 1730–1560, 1277, 1170, 1130, 900 cm$^{-1}$
NMR (DMSO-d$_6$, δ): 2.80–5.00 (13H, m); 6.60–8.20 (11H, m)
MASS: 570 (M+1), 456

50) (2R)-4-(4-Carbamoylbutyl)-1-[3,5-bis(trifluoromethyl)benzoyl]-2-(1H-indol-3-yl-methyl)piperazine hydrochloride
mp: 146°–156° C.
$[\alpha]_D^{21}$: +0.4° (C=0.5, DMF)
IR (Nujol): 3650–3050, 2750–1900, 1635, 1275, 1175, 1125, 900 cm$^{-1}$
NMR (DMSO-d$_6$, δ): 1.40–5.20 (17H, m); 6.60–8.30 (10H, m); 10.95 (1H, s); 11.05–11.40 (1H, m)
MASS: 555 (M+1) (free)

51) (2R)-1-[3,5-Bis(trifluoromethyl)benzoyl]-2-(1H-indol-3-yl-methyl)-4-[3-[(4-methyl-1-homopiperazinyl)-carbonyl]propyl]piperazine
$[\alpha]_D^{20}$: −13.5° (C=1.0, MeOH)
IR (Neat): 3225, 1630, 1430, 1275 cm$^{-1}$
NMR (DMSO-d$_6$, δ): 1.63–4.95 (28H, m); 6.60–8.19 (8H, m); 10.89 (1H s)
MASS: 638 (M+1)

52) (2R)-1-[3,5-Bis(trifluoromethyl)benzoyl]-2-(1H-indol-3-yl-methyl)-4-[3-[N-(4-methyl-1-piperazinyl)carbamoyl]propyl]piperazine
$[\alpha]_D^{19}$: −14.1 (C=1.0, MeOH)
IR (Neat): 3225, 1630, 1450, 1350, 1275 cm$^{-1}$
NMR (DMSO-d$_6$, δ): 1.68–4.85 (23H, m); 2.15 (3H, s); 6.64–8.76 (9H, m); 10.85 (1H, s)
MASS: 639 (M+1)

Example 33

The following compounds were obtained according to a similar manner to that of Example 10.

1) (2R)-4-(4-Carboxybutyl)-1-[3,5-bis(trifluoromethyl)-benzoyl]-2-(1H-indol-3-yl-methyl)piperazine hydrochloride
mp: 97°–100° C.
IR (Nujol): 3600–3100, 2700–2000, 1710, 1625, 1276, 1170, 1130, 900 cm$^{-1}$
NMR (DMSO-d$_6$, δ): 1.35–5.00 (17H, m); 6.60–8.20 (8H, m); 10.85 (1H, s); 12.01 (1H, s)
MASS: 556 (M+1) (free)

2) (2R)-4-(4-Carboxybenzyl)-1-[3,5-bis(trifluoromethyl)benzoyl]-2-(1H-indol-3-yl-methyl)piperazine hydrochloride
mp: >210° C.
$[\alpha]_D^{21}$: −36.4° (C=0.5, DMF)

NMR (DMSO-d$_6$, δ): 2.70–5.20 (11H, m); 6.50–8.25 (12H, m); 10.86 (1H, s); 11.30–13.40 (2H, m)

MASS: 590 (M+1) (free)

3) (2R)-4-[(4-Carboxypiperidino)carbonylmethyl]-1-[3,5-bis(trifluoromethyl)benzoyl]-2-(1H-indol-3-yl-methyl) piperazine hydrochloride mp: 143°–150° C.

IR (Nujol) 3600–3100, 2750–2000, 1710, 1630, 1277, 1170, 1130, 900 cm$^{-1}$

NMR (DMSO-d$_6$, δ): 1.30–5.00 (20H, m); 6.60–8.20 (8H, m); 10.89 (1H, s); 12.32 (1H, s)

MASS: 625 (M+1) (free)

Example 34

A mixture of (2R)-4-[3-(benzyloxycarbonyl)propyl]-1-[3,5-bis(trifluoromethyl)benzoyl]-2-(1H-indol-3-yl-methyl) piperazine (0.15 g), 10% Pd charcoal (15 mg) and methanol (4.5 ml) was stirred for 3 hours under hydrogen atmosphere (1 atm). The catalyst was removed by filtration and the filtrate was concentrated. The residue was purified by column chromatography on a silica gel using chloroform-methanol (5:1) as eluent to give (2R)-4-(3-carboxypropyl)-1-[3,5-bis(trifluoromethyl)benzoyl]-2-(1H-indol-3-yl-methyl)piperazine (0.067 g) as a powder.

mp: 112°–120° C.

$[\alpha]_D^{17}$: +3.6° (C=0.5, DMF)

IR (Nujol): 3600–3100, 1700, 1625, 1276, 1175, 1130, 900 cm$^{-1}$

NMR (DMSO-d$_6$, δ): 1.60–5.00 (15H, m); 6.60–8.20 (8H, m); 10.85 (1H, s)

MASS: 542 (M+1)

Example 35

The following compounds were obtained according to a similar manner to that of Example 34.

1) (2R)-4-(Carboxymethyl)-1-[3,5-bis(trifluoromethyl)-benzoyl]-2-(1H-indol-3-yl-methyl)piperazine mp: 152°–156° C.

$[\alpha]_D^{19}$: -3.0° (C=0.5, DMF)

IR (Nujol): 3600–3100, 1654, 1630, 1277, 1196, 1130 cm$^{-1}$

NMR (DMSO-d$_6$, δ): 2.20–5.20 (11H, m); 6.60–8.20 (8H, m); 10.85 (1H, s)

MASS: 514 (M+1)

2) (2R)-4-(Carboxymethyl)-2-(1H-indol-3-yl-methyl)-1-(3,5-dimethylbenzoyl)piperazine mp: 153°–157° C.

$[\alpha]_D^{21}$: +47.0° (C=0.5, DMF)

IR (Nujol): 3600–3150, 1632, 734 cm$^{-1}$

NMR (DMSO-d$_6$, δ): 2.05–5.00 (17H, m); 6.50–7.80 (8H, m); 10.83 (1H, s)

MASS: 406 (M+1)

3) (2R)-4-(Carboxymethyl)-1-[3,5-bis(trifluoromethyl)-benzoyl]-2-(3,4-dimethylbenzyl)piperazine mp: 120°–135° C.

4) (2R)-4-[N-(Carboxymethyl)carbamoylmethyl]-1-[3,5-bis(trifluoromethyl)benzoyl]-2-(1H-indol-3-yl-methyl) piperazine mp: 172°–175° C.

IR (Nujol): 3700–3100, 1700–1550, 1277, 1171, 1131, 900 cm$^{-1}$

NMR (DMSO-d$_6$; δ): 2.60–5.00 (13H, m); 6.60–8.20 (9H, m); 10.87 (1H, s)

MASS: 571 (M+1), 456

Example 36

To a mixture of (2R)-1-[3,5-bis(trifluoromethyl)-benzoyl]-2-(1H-indol-3-yl-methyl)-4-(4-nitro-trans-cinnamoyl) piperazine (100 mg), powdered sodium hydroxide (30 mg) and cetyltrimethylammonium bromide (10 mg) in dichloromethane (2 ml) was added 2-dimethylaminoethyl chloride hydrochloride (50 mg) at room temperature. The resulting mixture was stirred at the same temperature for 14 hours. After adding dichloromethane (10 ml), the reaction mixture was filtered through Celite pad and the filtrate was concentrated in vacuo. The resulting residue was purified by column chromatography on a silica gel eluting with a mixture of dichloromethane and methanol (30:1) and then treated with 4N hydrogen chloride in ethyl acetate solution to give (2R)-1-[3,5-bis(-trifluoromethyl)benzoyl]-2-[1-(2-dimethylaminoethyl)-1H-indol-3-yl-methyl]-4-(4-nitro-trans-cinnamoyl)piperazine hydrochloride (34 mg).

mp: 171°–175° C.

$[\alpha]_D^{24}$: -7.80° (C=0.5, MeOH)

IR (Nujol): 3650–3120, 2800–2000, 1635, 1510, 1278, 1171, 1130, 900 cm$^{-1}$

NMR (DMSO-d$_6$, δ): 2.60–5.20 (19H, m); 6.50–8.35 (14H, m); 10.51 (1H, br s)

FABMASS: : 702 (M+1) (free), 454

Example 37

The following compounds were obtained according to a similar manner to that of Example 23.

1) (2R)-4-(Benzyloxycarbonylmethyl)-1-[3,5-bis(trifluoromethyl)benzoyl]-2-(3,4-dimethylbenzyl)piperazine hydrochloride mp: 115°–120° C.

$[\alpha]_D^{18}$: -25.3° (C=0.5, MeOH)

IR (Nujol): 3350 (br), 2700–2300, 1745, 1640, 1500 cm$^{-1}$

NMR (DMSO-d$_6$, δ): 2.10 and 2.18 (6H, 2 s); 3.7–5.2 (11H, m); 5.24 (2H, s); 6.6–7.7 (10H, m); 8.18 (1H, br s)

MASS: 593 (M+1) (free), 445

2) (2R)-4-(Methoxycarbonylmethyl)-1-(3,5-dimethylbenzoyl)-2-(3,4-dimethylbenzyl)piperazine hydrochloride mp: 90°–120° C. (dec.)

$[\alpha]_D^{18}$: -39° (C=0.5, MeOH)

IR (Nujol): 3300 (br), 1745, 1630, 1590, 1500 cm-1

NMR (DMSO-d$_6$, δ): 2.1–2.4 (12H, m); 2.9–5.2 (12H, m); 3.74 (3H, s); 6.5–7.3 (6H, m)

MASS: 409 (M+1) (free)

3) ($^2$R)-1-[3,5-Bis(trifluoromethyl)benzoyl]-2-(1H-indol-3-yl-methyl)-4-[4-(dimethylamino)benzoyl]piperazine hydrochloride IR (Nujol): 3350–3220, 2600–2550, 2430–2340, 1622 cm$^{-1}$ NMR (DMSO-d$_6$, δ): 2.60–5.06 (9H, m); 4.68 (6H, s); 6.50–8.30 (13H, m); 10.85 (1H, s)

MASS: 603 (M+1) (free)

4) ($^2$R)-$^4$-(4-Aminobenzoyl)-1-[3,5-bis(trifluoromethyl)-benzoyl]-2-(1H-indol-3-yl-methyl)piperazine hydrochloride IR (Nujol): 3260, 2570, 1600–1590 cm$^{-1}$ NMR (DMSO-d$_6$, δ): 2.66–3.64 (6H, m); 3.82–5.00 (3H, m); 6.50–8.26 (14H, m); 10.88 (1H, s)

MASS: 575 (M+1) (free)

5) (2R)-4-(Carbamoylmethyl)-1-[3,5-bis(trifluoromethyl) benzoyl]-2-(1H-indol-3-yl-methyl)piperazine hydrochloride mp: >230° C.

$[\alpha]_D^{21}$: -21.2° (C=0.5, MeOH)

IR (Nujol): 3345, 3140, 2800–2400, 1679, 1655, 1276, 1130, 908 cm$^{-1}$

NMR (DMSO-d$_6$, δ): 3.00–5.20 (11H, m); 6.60–8.30 (10H, m); 10.99 (1H, s)

MASS: 513 (M+1) (free), 456

Example 38

To a stirred mixture of (2R)-4-(3-aminopropyl)-1-[3,5-bis(trifluoromethyl)benzoyl]-2-(3,4-dimethylbenzyl)-piperazine dihydrochloride (160 mg), nicotinic acid (33 mg) and triethylamine (0.17 ml) in dichloromethane (2 ml) was added 2-chloro-1-methylpyridinium iodide (78 mg) at room temperature. After stirring for 1.5 hours, the reaction mixture was evaporated under reduced pressure. The residue was partitioned between ethyl acetate (30 ml) and water (10 ml). The organic layer was separated and dried over magnesium sulfate. After evaporation of the solvent, the residue was purified by column chromatography on a silica gel with dichloromethane-methanol (40:1) as eluent to give (2R)-1-[3,5-bis(trifluoromethyl)benzoyl]-2-(3,4-dimethylbenzyl)-4-[3-(nicotinoylamino)propyl]-piperazine (70 mg).

$[\alpha]_D^{20}$: −21.5° (C=1.0, MeOH)

IR (Neat): 3350, 3000–2700, 1630, 1530, 1430, 1380 cm$^{-1}$

NMR (CDCl$_3$, δ): 1.7–2.0 (2H, m); 2.18 and 2.21 (6H, 2 s); 2.4–2.6 (2H, m); 2.6–5.2 (11H, m); 6.5–7.5 (7H, m); 7.82 (1H, br s); 8.12 (1H, d, J=8.0 Hz); 8.71 (1H, d, J=3.7 Hz); 8.97 (1H, br s)

MASS: 607 (M+1), 544, 502, 445

Example 39

The following compounds were obtained according to a similar manner to that of Example 38.

1) (2R)-1-[3,5-Bis(trifluoromethyl)benzoyl]-2-(3,4-dimethylbenzyl)-4-[2-(nicotinoylamino)ethyl]-piperazine $[\alpha]_D^{20}$: −17.3° (C=1.0, MeOH)

IR (Neat): 3300, 3050–2700, 1630, 1530, 1430, 1380, 1275 cm$^{-1}$

NMR (CDCl$_3$, δ): 2.16 and 2.21 (6H, 2 s); 2.6–2.8 (2H, m); 3.6–3.8 (2H, m); 6.5–7.6 (16H, n); 7.84 (1H, br s); 8.14 (1H, d, J=7.8 Hz); 8.72 (1H, br s); 9.01 (1H, br s)

MASS: 593 (M+1), 530, 473

2) (2R)-4-[[2-(N-Acetylamino)thiazol-4-yl]methyl]-1-[3,5-bis(trifluoromethyl)benzoyl]-2-(3,4-dimethylbenzyl)piperazine mp: 105°–110° C. (dec.)

$[\alpha]_D^{22}$: −27.30 (C=1.0, MeOH)

IR (Nujol): 3250, 3180, 3050, 1685, 1635, 1545, 1500, 1350, 1320 cm$^{-1}$

NMR (CDCl$_3$, δ): 2.1–2.3 (6H, m); 2.26 (3H, s); 2.6–5.2 (11H, m); 6.4–6.6 (1H, m); 6.79 (1H, S); 6.8–7.1 (2H, m); 7.2–7.5 (2H, m); 7.81 (1H, br s); 9.29 (1H, br s)

MASS: 599 (M+1), 445

3) (2R)-4-[2-(Acetylamino)ethyl]-1-[3,5-bis(trifluoromethyl)benzoyl]-2-(3,4-dimethylbenzyl)piperazine hydrochloride mp: 90°–105° C. (dec.)

$[\alpha]_D^{20}$: −23.6° (C=0.5, MeOH)

IR (Nujol): 3250 (br), 2700–2300, 1630, 1530, 1450, 1360, 1270 cm$^{-1}$

NMR (DMSO-d$_6$, δ): 1.87 (3H, s); 2.10 and 2.18 (6H, 2 s); 2.6–5.2 (13H, m); 6.6–7.7 (5H, m); 8.1–8.5 (2H, m); 10.9–11.2 (1H, br s)

MASS: 529 (M+1) (free), 445

4) (2R)-4-[3-(Acetylamino)propyl]-1-[3,5-bis(trifluoromethyl)benzoyl]-2-(3,4-dimethylbenzyl)piperazine hydrochloride mp: 85°–100° C. (dec.)

$[\alpha]_D^{20}$: 31 17.5° (C=1.0, MeOH)

IR (Nujol): 3300 (br), 2700–2300, 1630, 1450, 1360, 1270 cm$^{-1}$

NMR (DMSO-d$_6$, δ): 1.83 (3H, s); 1.8–2.0 (2H, m); 2.09 and 2.18 (6H, 2 s); 2.6–5.2 (15H, m); 7.6–7.3 (3H, m); 7.4–8.3 (3H, m); 11.0–11.4 (1H, m)

MASS: 544 (M+1) (free), 502, 445

5) (2R)-4-[4-(Acetylamino)benzyl]-1-[3,5-bis(trifluoromethyl)benzoyl]-2-(1H-indol-3-yl-methyl)piperazine hydrochloride mp: 196°–200° C.

$[\alpha]_D^{21}$: −31.4° (C=0.5, DMF)

IR (Nujol): 3600–3100, 2700–2000, 1640, 1530, 1276, 1175, 1130, 900 cm$^{-1}$

NMR (DMSO-d$_6$, δ): 1.80–5.20 (14H, m); 6.50–8.25 (13H, m); 10.16 (1H, s); 10.86 (1H, s)

MASS: 603 (M+1) (free)

6) (2R)-4-[4-(Acetylamino)benzoyl]-1-[3,5-bis(trifluoromethyl)benzoyl]-2-(1H-indol-3-yl-methyl)piperazine IR (Nujol): 3250, 1628, 1525 cm$^{-1}$ NMR (DMSO-d$_6$, δ): 2.08 (3H, s); 2.90–5.02 (9H, m); 6.54–8.40 (12H, m); 10.14 (1H, s); 10.83 (1H, s)

MASS: 617 (M+1)

7) (2R)-4-[3-(Acetylamino)propyl]-1-[3,5-bis(trifluoromethyl)benzoyl]-2-(1H-indol-3-yl-methyl)piperazine hydrochloride IR (Nujol): 3210, 1630, 1544 cm$^{-1}$ NMR (DMSO-d$_6$, δ): 1.81 and 1.84 (3H, 2 s); 1.60–2.05 (2H, m); 2.94–5.18 (13H, m); 6.57–8.29 (9H, m); 10.97 (1H, s); 11.28 and 11.36 (1H, 2 br s)

MASS: 555 (M+1) (free)

Example 40

To a stirred mixture of (2R)-4-(2-aminoethyl)-1-[3,5-bis(trifluoromethyl)benzoyl]-2-(3,4-dimethylbenzyl)-piperazine dihydrochloride (110 mg), triethylamine (0.2 ml) in dichloromethane (10 ml) was added methanesulfonyl chloride (0.1 ml) at 0° C. After stirring for 1 hour, the reaction mixture was poured into ice-water and extracted with ethyl acetate. The extract was washed successively with aqueous saturated sodium bicarbonate solution and brine, and dried. After evaporation of the solvent in vacuo, the residue was purified by column chromatography on a silica gel eluting with a mixture of dichloromethane and methanol (40:1) and treated with 4N hydrogen chloride in ethyl acetate solution to give (2R)-1-[3,5-bis(trifluoromethyl)benzoyl]-2-(3,4-dimethylbenzyl)-4-[2-(mesylamino)ethyl]piperazine hydrochloride (50 mg).

mp: >220° C.

$[\alpha]_D^{22}$: +0.2° (C=0.5, DMF)

IR (Nujol): 3350, 2700–2400, 1645, 1500, 1450, 1380 cm$^{-1}$

NMR (DMSO-d$_6$, δ): 2.10 and 2.18 (6H, 2 s); 2.7–5.2 (17H, m); 6.6–7.7 (5H, m); 8.1–8.2 (1H, m); 11.05–11.4 (1H, m)

MASS: 566 (M+1) (free)

Example 41

The following compounds were obtained according to a similar manner to that of Example 40.

1) (2R)-1-[3,5-Bis(trifluoromethyl)benzoyl]-2-(1H-indol-3-yl-methyl)-4-[4-(mesylamino)benzyl]piperazine hydrochloride mp: 152°–165° C.

$[\alpha]_D^{23}$: −32.2° (C=0.5, DMF)

IR (Nujol): 3600–3100, 2750–2000, 1635, 1278, 1172, 1140, 900 cm$^{-1}$

NMR (DMSO-d$_6$, δ): 3.00–5.10 (14H, m); 6.50–8.25 (13H, m); 10.03 (1H, s); 10.85 (1H, s)

MASS: 639 (M+1) (free), 456

2) (2R)-1-[3,5-Bis(trifluoromethyl)benzoyl]-2-(3,4-dimethylbenzyl)-4-[3-(mesylamino)propyl]piperazine hydrochloride mp: 165°–180° C.

$[\alpha]_D^{22}$: −0.7° (C=1.0, DMF)

IR (Nujol): 3350, 2700–2400, 1645, 1500, 1450, 1380 cm$^{-1}$

NMR (DMSO-d$_6$, δ): 1.8–2.1 (2H, m); 2.09 and 2.18 (6H, 2 s); 2.6–5.2 (17H, m); 6.68 (1H, br s); 7.0–7.4 (2H, m); 7.42 and 7.69 (2H, 2 s); 8.1–8.2 (1H, m); 11.0–11.4 (1H, m)

MASS: 580 (M+1) (free), 445

3) (2R)-1-[3,5-Bis(trifluoromethyl)benzoyl]-2-(1H-indol-3-yl-methyl)-4-[4-(mesylamino)benzoyl]piperazine IR (Nujol): 3260–3170, 1627 cm$^{-1}$ NMR (DMSO-d$_6$, δ): 3.06 (3H, s); 2.60–3.66 (6H, m); 3.84–5.02 (3H, m); 6.52–8.44 (12H, m); 10.05 (1H, s); 10.83 (1H, s)

MASS: 653 (M+1)

4) (2R)-1-[3,5-Bis(trifluoromethyl)benzoyl]-2-(1H-indol-3-yl-methyl)-4-(phenylsulfonyl)piperazine $[\alpha]_D^{21}$: +46.1° (C=1.0, MeOH)

IR (Neat): 3500–3100, 1635, 1276, 1165, 1130, 900 cm$^{-1}$

NMR (DMSO-d$_6$, δ): 2.20–5.00 (9H, m); 6.40–8.20 (13H, m); 10.90 (1H, br s)

MASS: 596 (M+1)

Example 42

A mixture of (2R)-1-[3,5-bis(trifluoromethyl)-benzoyl]-2-(1H-indol-3-yl-methyl)-4-(phthalimidomethyl-carbonyl)piperazine (250 mg), hydrazine hydrate (50 mg) in ethanol (5 ml) was heated under reflux for 2 hours. The resulting precipitate was removed by filtration and the filtrate was evaporated under reduced pressure. The residue was washed with aqueous 1N sodium hydroxide solution and then purified by column chromatography on a silica gel eluting with a mixture of ethyl acetate and methanol (4:1) to afford (2R)-4-(2-aminoacetyl)-1-[3,5-bis(trifluoromethyl)benzoyl]-2-(1H-indol-3-yl-methyl)piperazine (110 mg).

mp: 110°–120° C.

$[\alpha]_D^{21}$: −4.4° (C=1.0, MeOH)

IR (Nujol): 3600–3100, 1634, 1277, 1130, 900 cm$^{-1}$

NMR (DMSO-d$_6$, δ): 2.60–5.20 (13H, m); 6.55–8.30 (8H, m); 10.87 (1H, br s)

MASS: 513 (M+1), 456

Example 43

The following compounds were obtained according to a similar manner to that of Example 42.

1) (2R)-4-(3-Aminopropyl)-1-[3,5-bis(trifluoromethyl)-benzoyl]-2-(3,4-dimethylbenzyl)piperazine dihydrochloride mp: 98°–1050° C. (dec.)

$[\alpha]_D^{20}$: 31 18.8° (C=0.5, DMF)

IR (Nujol): 3300 (br), 2900–2500, 1630, 1500, 1430, 1380, 1350 cm$^{-1}$

NMR (DMSO-d$_6$, δ): 2.09 and 2.18 (6H, 2 s); 1.6–5.0 (1SH, m); 6.6–7.7 (6H, m); 7.9–8.3 (4H, m)

MASS: 502 (M+1) (free), 445

2) (2R)-4-(2-Aminoethyl)-1-[3,5-bis(trifluoromethyl)-benzoyl]-2-(3,4-dimethylbenzyl)piperazine dihydrochloride mp: 160°–170° C. (dec.)

$[\alpha]_D^{20}$: −0.8° (C=0.5, DMF)

IR (Nujol): 3300 (br), 2700–2500, 1630, 1500, 1430, 1360 cm$^{-1}$

NMR (DMSO-d$_6$, δ): 2.10 and 2.19 (6H, 2 s); 2.6–5.2 (13H, m); 6.6–7.7 (5H, m); 8.2–8.3 (1H, m); 8.1–8.8 (4H, br m)

MASS: 488 (M+1) (free), 445

Example 44

A mixture of (2R)-1-[3,5-bis(trifluoromethyl)-benzoyl]-2-(1H-indol-3-yl-methyl)-4-(4-nitrobenzyl)-piperazine (360 mg), iron powder (360 mg), ammonium chloride (36 mg) and water (1.5 ml) in ethanol (6 ml) was heated under reflux for 40 minutes. After cooling, the reaction mixture was filtered and the filtrate was evaporated under reduced pressure. The residue was purified by column chromatography on a silica gel eluting with a mixture of dichloromethane and methanol (10:1) to give (2R)-4-(4-aminobenzyl)-1-[3,5-bis(trifluoromethyl)-benzoyl]-2-(1H-indol-3-yl-methyl) piperazine (0.34 g).

$[\alpha]_D^{18}$: −35.8° (C=0.5, DMF)

IR (Neat): 3500–3100, 1623, 1514, 1274, 1170, 1130, 900 cm$^{-1}$

NMR (DMSO-d$_6$, δ): 1.90–4.90 (11H, m); 4.97 (2H, s); 6.50–8.20 (12H, m); 10.80 (1H, s)

MASS: 561 (M+1), 456

Example 45

The following compound was obtained according to a similar manner to that of Example 44.

(2R)-4-(4-Aminobenzoyl)-1-[3,5-bis(trifluoromethyl)-benzoyl]-2-(1H-indol-3-yl-methyl) piperazine IR (Neat): 3330, 3000, 2910, 1625–1600, 1515 cm$^{-1}$ NMR (DMSO-d$_6$, δ): 2.60–3.64 (SH, m); 3.80–4.40 (4H, m); 4.79–5.70 (2H, m); 6.43–8.40 (12H, m); 10.85 (1H, s)

MASS: 575 (X+1)

Example 46

A solution of 4N hydrogen chloride in ethyl acetate solution (1.5 ml) was added dropwise to a solution of (2R)-1-[3,5-bis(trifluoromethyl)benzoyl]-2-(1H-indol-3-yl-methyl)-4-[(4-trityl-1-piperazinyl)carbonymethyl]-piperazine (480 mg) in ethyl acetate (5 ml) at 0° C. The resulting mixture was stirred at the same temperature for 1 hour and then allowed to stand overnight. Aqueous saturated sodium bicarbonate solution (20 ml) was added to the reaction mixture, and the product was extracted with ethyl acetate. The organic phase was washed with brine and dried. After evaporation of the solvent in vacuo, the residue was purified by column chromatography on a silica gel eluting with a mixture of dichloromethane and methanol (5:1) and treated with 4N hydrogen chloride in dioxane solution to afford (2R)-1-t3,5-bis(trifluoromethyl)-benzoyl]-2-(1H-indol-3-yl-methyl)-4-[(1-piperazinyl)-carbonylmethyl] piperazine dihydrochloride (250 mg).

mp: 210°–218° C.

$[\alpha]_D^{19}$: −25.60 (C=0.5, DMF)

IR (Nujol): 3650–3100, 2700–2000, 1645, 1275, 1174, 1130, 902 cm$^{-1}$

NMR (DMSO-d$_6$, δ): 3.00–5.20 (20H, m); 6.60–8.30 (8H, m); 9.73 (2H, br s); 10.99 (1H, s)

MASS: 582 (X+1) (free)

Example 47

A mixture of (2R)-1-[3,5-bis(trifluoromethyl)-benzoyl]-4-(2-chloroacetyl)-2-(1H-indol-3-yl-methyl)piperazine (730 mg), potassium phthalimide (260 mg) in dimethylformamide (10 ml) was stirred at room temperature for 7 hours and then poured into aqueous sodium chloride solution (100 ml). The resulting precipitate was collected by filtration, washed with water and dried. The crude product was dissolved in toluene (7 ml) and filtered. To the filtrate was added n-hexane (35 ml) and the whole was stirred for 10 minutes. The resulting powder was collected by filtration, washed with ethyl ether and dried to give (2R)-1-[3,5-bis (trifluoromethyl)benzoyl]-2-(1H-indol-3-yl-methyl)-4-(phthalimidomethylcarbonyl) piperazine (500 mg).

mp: >220° C.

$[\alpha]_D^{19}$: −1.2° (C=0.5, DMF)

IR (Nujol): 3500–3200, 1772, 1708, 1647, 1275, 1183, 1131, 900 cm$^{-1}$

NMR (DMSO-d$_6$, δ): 2.50–5.20 (11H, m); 6.60–8.30 (12H, m); 10.83–10.94 (1H, m)

MASS: 643 (M+1)

Example 48

A mixture of (2R)-1-[3,5-bis(trifluoromethyl)-benzoyl]-2-(1H-indol-3-yl-methyl)piperazine (150 mg), acrylamide (24 mg) in toluene (1.5 ml) was stirred at room temperature for 1 hour and then was refluxed for 5 hours. After additional acrylamide (24 mg) was added, the whole mixture was refluxed for 3 hours and evaporated under reduced pressure. The obtained residue was purified by column chromatography on a silica gel eluting with a mixture of ethyl acetate and methanol (10:1) to give (2R)-1-[3,5-bis(trifluoromethyl) benzoyl]-4-(2-carbamoylethyl)-2-(1H-indol-3-yl-methyl) piperazine (89 mg).

mp: 80°–100° C.

$[\alpha]_D^{17}$: +3.6° (C=0.5, DMF)

IR (Nujol): 3600–3100, 1673, 1636, 1276, 1170, 1130, 900 cm$^{-1}$

NMR (DMSO-d$_6$, δ): 2.00–4.90 (13H, m); 6.60–8.20 (10H, m); 10.84 (1H, s)

MASS: 527 (M+1), 456

Example 49

To a stirred solution of (2R)-1-[3,5-bis(trifluoromethyl) benzoyl]-2-(3,4-dimethylbenzyl)-4-(2-chloroacetyl) piperazine (300 mg) in tetrahydrofuran (5 ml) was added N-methylbenzylamine (140 mg) at room temperature. After stirring for 2 hours, additional N-methylbenzylamine (70 mg) was added, and then the whole was heated at 45° C. for 6 hours. The mixture was concentrated in vacuo and the residue was partitioned between ethyl acetate (20 ml) and aqueous sodium bicarbonate solution (10 ml). The organic layer was separated and dried over magnesium sulfate. After evaporation of the solvent in vacuo, the residue was purified by column chromatography on a silica gel eluting with a mixture of dichloromethane and methanol (50:1) and treated with 4N hydrogen chloride in ethyl acetate solution to afford (2R)-1-[3,5-bis(trifluoromethyl)-benzoyl]-4-[2-(N-benzyl-N-methylamino)acetyl]-2-(3,4-dimethylbenzyl)piperazine hydrochloride (0.35 g).

mp: 207°–208° C.

$[\alpha]_D^{24}$: −1.40° (C=1.0, MeOH)

IR (Nujol): 3350 (br), 2700–2600, 1635, 1450, 1370, 1350, 1330 cm$^{-1}$

NMR (DMSO-d$_6$, δ): 2.10 and 2.18 (6H, 2 s); 2.7–5.1 (16H, m); 6.5–6.8 (1H, m); 6.9–7.3 (2H, m); 7.4–7.7 (7H, m); 8.1–8.3 (1H, m); 10.0–10.4 (1H, m)

MASS: 606 (M+1) (free), 445

Example 50

The following piperazine derivatives (Table 1) were prepared by the similar manner to that of the each Example No. defined in the "Process" column. The physical properties of the object compounds are shown after the table.

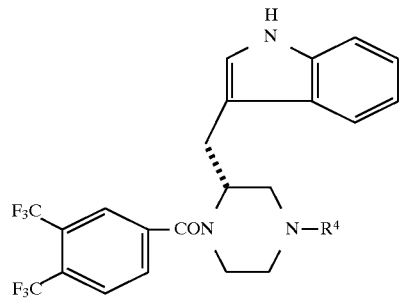

TABLE 1

| Example No. | Object Compounds R$^4$ | | Salt | Starting Compound | Process |
|---|---|---|---|---|---|
| 50-1) | —(CH$_2$)$_4$NHSO$_2$CH$_3$ | | HCl | Ex. 50-21) | Ex. 40 |
| 50-2) | —(CH$_2$)$_3$NHCO— | —NO$_2$ | HCl | Ex. 50-20) | Ex. 40 |
| 50-3) | —(CH$_2$)$_3$NHCOOC$_2$H$_5$ | | HCl | Ex. 50-20) | Ex. 40 |
| 50-4) | —(CH$_2$)$_3$NHCO— | | HCl | Ex. 50-20) | Ex. 40 |
| 50-5) | —(CH$_2$)$_3$NHCOCOOC$_2$H$_5$ | | HCl | Ex. 50-20) | Ex. 40 |

TABLE 1-continued

| Example No. | Object Compounds R⁴ | Salt | Starting Compound | Process |
|---|---|---|---|---|
| 50-6) | —(CH₂)₃NHSO₂—C₆H₅ | HCl | Ex. 50-20) | Ex. 40 |
| 50-7) | —(CH₂)₃NHSO₂CH₃ | HCl | Ex. 50-20) | Ex. 40 |
| 50-8) | —(CH₂)₃NHCO—C₆H₄—COCH₃ | HCl | Ex. 50-20) | Ex. 38 |
| 50-9) | —(CH₂)₃NHCO—C₆H₄—CN | HCl | Ex. 50-20) | Ex. 38 |
| 50-10) | —(CH₂)₃NHCO—C₆H₄—F | HCl | Ex. 50-20) | Ex. 38 |
| 50-11) | —(CH₂)₃NHCO-(1-methylindol-3-yl) | HCl | Ex. 50-20) | Ex. 38 |
| 50-12) | —(CH₂)₂NHSO₂CH₃ | HCl | Ex. 65 | Ex. 40 |
| 50-13) | —(CH₂)₂N=CH—C₆H₄—OH | — | Ex. 6 | Ex. 14 |
| 50-14) | —CH₂CN | — | Ex. 6 | Ex. 11 |
| 50-15) | —(CH₂)₃CN | — | Ex. 6 | Ex. 11 |
| 50-16) | —(CH₂)₃-phthalimido | — | Ex. 6 | Ex. 11 |
| 50-17) | —(CH₂)₄-phthalimido | — | Ex. 6 | Ex. 11 |
| 50-18) | —CH₂CN | HCl | Ex. 50-14) | Ex. 23 |
| 50-19) | —(CH₂)₃CN | HCl | Ex. 50-15) | Ex. 23 |
| 50-20) | —(CH₂)₃NH₂ | 2HCl | Ex. 50-16) | Ex. 42 |
| 50-21) | —(CH₂)₄NH₂ | 2HCl | Ex. 50-17) | Ex. 42 |
| 50-22) | —(CH₂)₃NHCONH—C₆H₅ | HCl | Ex. 50-20) | Ex. 62 |
| 50-23) | —CO—C₆H₄—COOCH₃ | — | Ex. 6 | Ex. 16 |

TABLE 1-continued

| Example No. | Object Compounds R⁴ | Salt | Starting Compound | Process |
|---|---|---|---|---|
| 50-24) | —CO—C₆H₄—COOH (para) | — | Ex. 50-23) | Ex. 10 |
| 50-25) | —CH₂CONHNHCONH₂ | — | Ex. 35-1) | Ex. 27 |
| 50-26) | —CON(CH₃)—(CH₂)₃CH₃ | — | Ex. 6 | Ex. 63 |
| 50-27) | —CH₂CON(CH₃)(OCH₃) | — | Ex. 35-1) | Ex. 27 |
| 50-28) | —(CH₂)₃CONHOCH₃ | HCl | Ex. 34 | Ex. 27 |
| 50-29) | —(CH₂)₃CON(4-methylpiperazin-1-yl) | — | Ex. 34 | Ex. 27 |
| 50-30) | —(CH₂)₃CONHCH₃ | — | Ex. 34 | Ex. 27 |
| 50-31) | —CH₂CONHOCH₃ | — | Ex. 35-1) | Ex. 27 |
| 50-32) | —CH₂CO—C₆H₄—NO₂ (para) | — | Ex. 6 | Ex. 11 |
| 50-33) | —CH₂CO—C₆H₄—NH₂ (para) | — | Ex. 50-32) | Ex. 44 |
| 50-34) | —CH₂CO—C₆H₄—NHSO₂CH₃ (para) | — | Ex. 50-33) | Ex. 40 |
| 50-35) | —CO(CH₂)₃N(CH₃)₂ | HCl | Ex. 61 | Ex. 23 |
| 50-36) | —CH(CH₃)COOC₂H₅ | — | Ex. 6 | Ex. 11 |
| 50-37) | —CH(CH₃)COOH | — | Ex. 50-36) | Ex. 10 |
| 50-38) | —CH(CH₃)CONHOCH₃ | — | Ex. 50-37) | Ex. 27 |
| 50-39) | —CH(CH₃)CONH₂ | — | Ex. 50-37) | Ex. 27 |
| 50-40) | —CH(CH₃)CON(4-methylpiperazin-1-yl) | HCl | Ex. 50-37) | Ex. 27 |
| 50-41) | —*CH(C₆H₅)COOCH₃  R and S isomers | — | Ex. 6 | Ex. 11 |

TABLE 1-continued

| Example No. | Object Compounds R⁴ | Salt | Starting Compound | Process |
|---|---|---|---|---|
| 50-42) | —CH₂CON⟨piperazine⟩N—CH₃ | citric acid | Ex. 32-41) | Ex. 23 |
| 50-43) | —CH(Ph)COOH | — | Ex. 50-41) | Ex. 10 |
| 50-44) | —*CHCONHN⟨piperazine⟩N—CH₃ (with phenyl); R and S isomers | — | Ex. 50-41) | Ex. 27 |
| 50-45) | —*CHCOOCH₃ (4-NO₂-phenyl); R and S isomers | — | Ex. 6 | Ex. 11 |
| 50-46) | —*CHCOOCH₃ (4-NH₂-phenyl); R or S | — | Ex. 50-45) | Ex. 44 |
| 50-47) | —*CHCOOCH₃ (4-NHSO₂CH₃-phenyl); R or S isomer | — | Ex. 50-46) | Ex. 40 |
| 50-48) | —(CH₂)₃—CONHN⟨piperazine⟩N—CH₃ | H₂SO₄ | Ex. 32-52) | Ex. 23 |
| 50-49) | —(CH₂)₃CON⟨piperidine⟩CH₂—Ph | HCl | Ex. 34 | Ex. 72 |
| 50-50) | —(CH₂)₃CON⟨piperazine⟩N—Ph | 2HCl | Ex. 34 | Ex. 72 |

TABLE 1-continued

| Example No. | Object Compounds R⁴ | Salt | Starting Compound | Process |
|---|---|---|---|---|
| 50-51) | —(CH₂)₃CON⟨N–⟨H⟩⟩ (piperazine-cyclohexyl) | 2HCl | Ex. 34 | Ex. 72 |
| 50-52) | —(CH₂)₃CONH(CH₂)₂N(CH₂)₂ | 2HCl | Ex. 34 | Ex. 72 |
| 50-53) | —(CH₂)₃CON⟨ ⟩ (piperidine) | HCl | Ex. 34 | Ex. 72 |
| 50-54) | —(CH₂)₃CON⟨N–pyridyl⟩ | 3HCl | Ex. 34 | Ex. 72 |
| 50-55) | —(CH₂)₃CON⟨ ⟩–CH–phenyl | HCl | Ex. 34 | Ex. 72 |
| 50-56) | —(CH₂)₃CON⟨N–C(phenyl)₃⟩ | — | Ex. 34 | Ex. 72 |
| 50-57) | —(CH₂)₃CON⟨ ⟩NH | 2HCl | Ex. 50-56) | Ex. 46 |
| 50-58) | —(CH₂)₃CON⟨N–CH₃⟩ | H₂SO₄ | Ex. 34 | Ex. 72 |

Physical properties of the compounds of the Example 50:

Example 50–1)

IR (Nujol): 3260–3170, 1635 cm⁻¹

NMR (DMSO-d₆,δ): 1.40–1.94 (4H, m); 2.80–5.20 (13H, m); 2.90, 2.92 (3H, 2 s); 6.60–8.30 (9H, m); 10.95 (1H, s); 10.86–11.32 (1H, m)

MASS: 605 (M+1) (free)

Example 50–2)

IR (Nujol): 3230, 2570, 1638, 1596 cm⁻¹

NMR (DMSO-d₆, δ): 1.90–2.20 (2H, m); 3.00–5.20 (13H, m); 6.59–8.40 (12H, m); 8.98–9.13 (1H, m); 10.96 (1H, s); 10.95–11.34 (1H, m)

MASS: 662 (M+1) (free)

Example 50–3)

IR (Nujol): 3260, 2560, 1697, 1635 cm⁻¹

NMR (DMSO-d₆, δ): 1.07–1.23 (3H, m); 1.70–2.05 (2H, m); 2.95–5.18 (15H, m); 6.60–8.30 (9H, m); 10.96 (1H, s); 11.00–11.38 (1H, m)

MASS: 585 (M+1) (free)

Example 50–4)

IR (Nujol): 3230, 2560, 1635, 1574, 1531 cm⁻¹

NMR (DMSO-d₆, δ): 1.82–2.18 (2H, m); 2.94–5.24 (13H, m); 6.57–8.29 (13H, m); 8.63–8.80 (1H, m); 10.96 (1H, s); 10.86–11.27 (1H, m)

MASS: 617 (M+1) (free)

Example 50–5)

IR (Nujol): 3240, 2560, 1734, 1685, 1635, 1523 cm⁻¹

NMR (DMSO-d₆, δ): 1.28 (3H, t, J=7.06 Hz); 1.75–2.14 (2H, m); 2.88–4.16, 4.49–4.67, 5.02–5.21 (13H, m) ; 4.24 (2H, q, t=7.06 Hz); 6.57–8.29 (8H, m)); 9.11 (1H, m)); 10.96 (1H, s); 11.03–11.35 (1H, m)

MASS: 613 (M+1) (free)

Example50–6)

IR (Nujol): : 3350–3200, 1636 cm⁻¹

NMR (DMSO-d₆, δ): 1.89–2.08 (2H, m); 2.70–2.94 (2H, m); 2.94–4.15, 4.50–4.68, 5.00–5.20 (11H, m)); 6.57–8.31 (14H, m); 10.96 (1H, s); 11.05–11.40 (1H, m)

MASS: 653 (M+1) (free)

Example 50–7)

IR (Nujol): 3150, 1601 cm⁻¹

NMR (DMSO-d₆, δ): 1.82–2.14 (2H, m); 2.92, 2.94 (3H, s); 2.96–4.17, 4.50–4.70, 5.04–5.20 (13H, m); 6.60–8.28 (9H, m); 10.94 (1H, s); 11.25, 11.40 (1H, br s)

MASS: 591 (M+1) (free)

Example 50–8)

IR (Nujol): 3240, 1677, 1635, 1538 cm$^{-1}$
NMR (DMSO-d$_6$, δ): 1.85–2.20 (2H, m); 2.62 (3H, s); 3.00–4.23, 4.49–4.67, 5.05–5.21 (13H, m); 6.12–8.27 (12H, m); 8.91 (1H, m); 10.94 (1H, s); 11.04–11.37 (1H, m)
MASS: 659 (M+1) (free)

Example 50–9)

IR (Nujol): 3250, 1638 cm$^{-1}$
NMR (DMSO-d$_6$, δ): 1.82–2.24 (2H, m); 2.90–5.20 (13H, m); 6.55–8.28 (12H, m); 8.90–9.10 (1H, m); 10.96 (1H, s); 10.84–11.34 (1H, m)
MASS: 642 (M+1) (free)

Example 50–10)

IR (Nujol): 3230, 1634 cm$^{-1}$
NMR (DMSO-d$_6$, δ): 1.87–2.20 (2H, m); 2.94–5.24 (13H, m); 6.56–8.29 (12H, m); 8.66–8.88 (1H, m); 10.96 (1H, s); 10.90–11.33 (1H, m)
MASS: 635 (M+1) (free)

Example 50–11)

IR (Nujol): 3240, 2710–2570, 1630, 1540 cm$^{-1}$
NMR (DMSO-d$_6$, δ): 1.89–2.20 (2H, m); 3.00–5.20 (13H, m); 3.83 (3H, s); 6.59–8.26 (14H, m); 10.95 (1H, s); 10.84–11.28 (1H, m)
MASS: 670 (M+1) (free)

Example 50–12)

IR (Nujol): 3250, 1634 cm$^{-1}$
NMR (DMSO-d$_6$, δ): 2.98, 3.01 (3H, 2 s); 2.60–5.18 (13H, m); 6.54–8.25 (9H, m); 10.95 (1H, s); 11.12–11.52 (1H, m)
MASS: 577 (M+1) (free)

Example 50–13)

IR (Neat): 3240, 3040, 2910, 1653–1612 cm$^{-1}$
NMR (CDCl$_3$, δ): 2.20–4.10 (13H, m); 6.77–8.44 (15H, m)
MASS: 603 (M+1)

Example 50–14)

IR (CHCl$_3$): 3270, 2990, 2920, 2220, 1714, 1661–1610 cm$^{-1}$
NMR (DMSO-d$_6$, δ): 2.20–3.45, 3.70–4.00, 4.26–4.44, 4.85–5.05 (11H, m); 6.55–8.24 (8H, m); 10.87 (1H, s)
MASS: 495 (M+1)

Example 50–15)

IR (Neat): 3280, 2230, 1664, 1626 cm$^{-1}$
NMR (DMSO-d$_6$, δ): 1.64–2.44 (4H, m); 2.54–4.97 (11H, m); 6.56–8.25 (8H, m); 10.86 (1H, s)
MASS: 523 (M+1)

Example 50–16)

IR (Neat): 3270, 2920, 1766, 1703, 1667, 1630 cm$^{-1}$
NMR (DMSO-d$_6$, δ): 1.70–2.45 (4H, m); 2.78–4.92 (11H, m); 6.54–8.22 (12H, m); 10.83 (1H, s)
MASS: 643 (M+1)

Example 50–17)

IR (CHCl$_3$): 3300, 2920, 1766, 1706, 1627 cm$^{-1}$
NMR (DMSO-d$_6$, δ): 1.35–1.82 (4H, m); 1.85–2.44 (2H, m); 2.70–4.35, 4.76–4.94 (11H, m); 6.56–8.22 (12H, m); 10.84 (1H, s)
MASS: 657 (M+1)

Example 50–18)

IR (Neat): 3280, 2910, 2210, 1740, 1630 cm$^{-1}$
NMR (DMSO-d$_6$, δ) 2.20–5.06 (11H, m); 6.54–8.24 (8H, m); 10.89 (1H, s); 10.75–11.03 (1H, m)
MASS: 495 (M+1) (free)

Example 50–19)

IR (Nujol): 3360–3230, 2710–2230, 1635 cm$^{-1}$
NMR (DMSO-d$_6$, δ): 2.00–2.27 (2H, m); 2.58–2.80 (2H, m); 2.96–5.19 (11H, m); 6.56–8.28 (8H, m); 10.94 (1H, s); 11.36–11.73 (1H, m)
MASS: 523 (M+1) (free)

Example 50–20)

IR (Nujol): 3450, 1635 cm$^{-1}$
NMR (DMSO-d$_6$, δ): 1.96–2.28 (2H, m); 2.75–5.22 (13H, m); 6.56–8.30 (11H, m); 10.96 (1H, s); 11.54–11.88 (1H, m)
MASS: 513 (M+1) (free).

Example 50–21)

IR (Nujol): 3340, 1635 cm$^{-1}$
NMR (DMSO-d$_6$, δ): 1.50–2.00 (4H, m); 2.68–5.20 (13H, m); 6.56–8.28 (11H, m); 10.96 (1H, s); 11.54 (1H, br s)
MASS: 527 (M+1) (free)

Example 50–22)

IR (Nujol): 3270, 1637, 1595 cm$^{-1}$
NMR (DMSO-d$_6$, δ): 1.68–2.10 (2H, m); 3.00–3.74, 4.02–4.19, 4.49–4.68, 5.05–5.20 (13H, m); 6 43–8.28 (14H, m); 8.75, 8.81 (1H, s); 10.95 (1H, s); 10.72–11.00 (1H, m)
MASS: 632 (M+1) (free)

Example 50–23)

IR (Neat): 3250, 2980, 2900, 1714, 1625, 1575 cm$^{-1}$
NMR (DMSO-d$_6$, δ): 2.87–5.03 (9H, m); 3.89 (3H, s); 6.45–8.26 (12H, m); 10.78, 10.89 (1H, 2 br s)
MASS: 618 (M+1)

Example 50–24)

IR (Neat): 3330–3220, 2960, 1612, 1540 cm$^{-1}$
NMR (DMSO-d$_6$, δ): 2.83–4.43 (10H, m); 6.54–8.22 (12H, m); 10.88 (1H, s)
MASS: 604 (M+1)

Example 50–25)

mp: >220° C.
[α]$_D^{24}$: –11.2° (C=0.5, DMF)
IR (Nujol): 3360, 3180, 1715, 1656, 1630, 1273, 1190, 1120, 903 cm$^{-1}$
NMR (DMSO-d$_6$, δ): 2.05–5.00 (11H, m); 5.94 (2H, s); 6.60–8.20 (9H, m); 9.50 (1H, s); 10.83 (1H, s)

MASS: 571 (M+1)

Example 50–26)

IR (Neat): 3260, 2920, 2850, 1626 cm$^{-1}$
NMR (DMSO-d$_6$, δ): 0.88 (3H, t, J=7.2 Hz); 1.10–1.63 (4H, m); 2.85 (3H, s); 2.69–5.05 (11H, m); 6.57–8.30 (8H, m); 10.88 (1H, s)
MASS: 569 (M+1)

Example 50–27)

$[α]_D^{21}$: –4.6° (C=1.0, MeOH)
IR (Neat): 3300, 1630, 1430, 1275 cm$^{-1}$
NMR (DMSO-d$_6$, δ): 2.20–4.90 (11H, m); 3.13 (3H, s); 3.71 (3H, s); 6.60–8.20 (8H, m); 10.86 (1H, s)
MASS: 557 (M+1)

Example 50–28)

$[α]_D^{21}$: –7.0° (C=1.0, MeOH)
IR (Neat): 3150, 2550, 2440, 2325, 1640, 1430, 1355, 1275 cm$^{-1}$
NMR (DMSO-d$_6$, δ): 2.0–5.20 (15H, m); 3.60 (3H, s); 6.17–8.23 (8H, m); 10.97 (1H, s); 11.3 (1H, br s)
MASS: 571 (M+1) (free)

Example 50–29)

$[α]_D^{20}$: –14.7° (C=1.0, MeOH)
IR (Neat): 3260, 1625, 1430, 1350, 1275 cm$^{-1}$
NMR (DMSO-d$_6$, δ): 1.60–4.95 (23H, m); 2.16 (3H, s); 6.6–8.19 (8H, m); 10.87 (1H, s)
MASS: 624 (M+1)

Example 50–30)

$[α]_D^{20}$: –10.5° (C=1.0, MeOH)
IR (Neat): 3260, 1650, 1630, 1570, 1430, 1350, 1275 cm$^{-1}$
NMR (DMSO-d$_6$, δ): 1.63–4.90 (15H, m); 2.59 (2H, d); 6.15–8.20 (9H, m); 10.87 (1H, s)
MASS: 555 (M+1)

Example 50–31)

$[α]_D^{20}$: –6.2° (C=1.0, MeOH)
IR (Neat): 3250, 1670, 1625, 1430, 1350, 1275 cm$^{-1}$
NMR (DMSO-d$_6$, δ): 2.0–4.85 (9H, m); 2.97 (2H, s); 3.63 (3H, s); 6.63–8.18 (8H, m); 10.86 (1H, s); 11.15 (1H, s)
MASS: 543 (M+1)

Example 50–32)

$[α]_D^{21}$: –18.9° (C=1.0, MeOH)
IR (Neat): 3300, 1690, 1625, 1525, 1430, 1345, 1275 cm$^{-1}$
NMR (DMSO-d$_6$, δ): 2.2–4.93 (11H, m); 6.54–8.48 (13H, m); 10.83 (1H, s)
MASS: 619 (M+1)

Example 50–33)

$[α]_D^{21}$: –34.8° (C=1.0, MeOH)
IR (Neat): 3350, 1620, 1590, 1440, 1275 cm$^{-1}$
NMR (DMSO-d$_6$, δ): 2.1–4.96 (11H, m); 5.94–8.26 (13H, m); 10.82 (1H, s)

MASS: 589 (M+1)

Example 50–34)

$[α]_D^{30}$: –18.9° (C=1.0, MeOH)
IR (Neat): 3400, 1685, 1625, 1365, 1275 cm$^{-1}$
NMR (DMSO-d$_6$, δ): 1.99 (3H, s); 2.10–4.93 (11H, m); 6.53–8.28 (12H, m); 10.81 (1H, s)
MASS: 667 (M+1)

Example 50–35)

IR (Nujol): 3350–3200, 2710, 1624 cm$^{-1}$
NMR (DMSO-d$_6$, δ): 1.77–2.10 (2H, m); 2.28–5.18 (13H, m); 2.74, 2.76 (6H, 2 s); 6.55–8.24 (8H, m); 10.51 (1H, br s); 10.93 (1H, s)
MASS: 569 (M+1) (free)

Example 50–36)

IR (Neat): 3300, 1720, 1630, 1430, 1275 cm$^{-1}$
NMR (DMSO-d$_6$, δ): 1.1–1.32 (6H, m); 2.2–4.93 (13H, m); 6.57–8.21 (8H, m); 10.84 (1H, s)
MASS: 556 (M+1)

Example 50–37)

$[α]_D^{20}$: –23.3° (C=1.0, MeOH)
IR (Neat): 3300, 1730, 1640, 1460, 1375, 1280 cm$^{-1}$
NMR (DMSO-d$_6$, δ): 1.4–1.6 (3H, m); 2.8–5.1 (10H, m); 6.6–8.26 (8H, m); 10.93 (1H, s)
MASS: 528 (M+1)

Example 50–38)

IR (Neat): 3250, 1670, 1625, 1275 cm$^{-1}$
NMR (DMSO-d$_6$, δ): 1.04–1.25 (3H, m); 2.16–4.90 (10H, m); 3.61 (3H, s); 6.60–8.27 (8H, m); 10.84 (1H, s); 11.09 (1H, s)
MASS: 557 (M+1)

Example 50–39)

$[α]_D^{19}$: –8.8° (C=1.0, MeOH)
IR (Neat): 3300, 1680, 1630, 1280 cm$^{-1}$
NMR (DMSO-d$_6$, δ): 1.0–1.2 (3H, m); 2.10–4.93 (10H, m); 6.6–8.24 (8H, m); 10.83 (1H, s)
MASS: 527 (M+1)

Example 50–40)

$[α]_D^{19}$: –16.5° (C=1.0, MeOH)
IR (Neat): 3300, 1630, 1460, 1370, 1275 cm$^{-1}$
NMR (DMSO-d$_6$, δ): 0.94–1.15 (3H, m); 2.15–5.0 (18H, m); 6.6–8.2 (8H, m); 10.88 (1H, s); 11.30 (1H, br s)
MASS: 610 (M+1) (free)

Example 50–41)

one isomer
$[α]_D^{19}$: +18.8° (C=1.0, MeOH)
IR (Nujol): 3240, 1745, 1630, 1450, 1275 cm$^{-1}$
NMR (DMSO-d$_6$, δ): 2.0–4.9 (10H, m); 3.62 (3H, s); 6.52–8.2 (13H, m); 10.8 (1H, s)
MASS: 604 (M+1)
the other isomer
$[α]_D^{19}$: –44.9° (C=1.0, MeOH)

IR (Neat):. 3300, 1730, 1625, 1275 cm$^{-1}$

NMR (DMSO-d$_6$, δ): 2.10–4.88 (10H, m); 3.65 (3H, s) 6.57–8.25 (13H, m); 10.77 (1H, s)

MASS: 604 (M+1)

Example 50–42)

mp: 194°–198° C. (dec.)

$[\alpha]_D^{29}$: –11.2° (C=0.5, DMF)

IR (Nujol): 3700–3150, 3000–2100, 1726, 1637, 1274, 1131; 896 cm$^{-1}$

NMR (DMSO-d$_6$, δ): 1.80–4.40 (24H, m); 6.50–8.20 (8H, m); 10.85 (1H, s)

MASS: 610 (M+1) (free)

Example 50–43)

IR (Nujol): 3300, 1710, 1680, 1455, 1280 cm$^{-1}$

NMR (DMSO-d$_6$, δ): 2.0–4.9 (10H, m); 6.5–8.28 (13H, m); 10.8 (2H,d)

Example 50–44)

one isomer $[\alpha]_D^{21}$: –10.1° (C=1.0, MeOH)

IR (Neat): 3200, 1670, 1620, 1450, 1275 cm$^{-1}$

NMR (DMSO-d$_6$, δ): 1.86–4.86 (18H, m); 2.15 (3H, s); 6.5–8.69 (13H, m); 9.24 (1H, s); 10.79 (1H, s)

MASS: 687 (M+1)

the other isomer $[\alpha]_D^{21}$: +11.2° (C=1.0, MeOH)

IR (Neat): 3200, 1650, 1275 cm$^{-1}$

NMR (DMSO-d$_6$, δ): 1.83–4.83 (18H, m); 2.16 (3H, s); 6.55–8.6 (13H, m); 9.2 (1H, s); 10.86 (1H, s)

MASS: 687 (M+1)

Example 50–45)

one isomer $[\alpha]_D^{20}$: +19.2° (C=1.0, MeOH)

IR (Neat): 3400, 1730, 1630, 1520, 1345, 1280 cm$^{-1}$

NMR (DMSO-d$_6$, δ): 2.10–4.93 (10H, m); 3.66 (3H, s); 6.55–8.34 (12H, m); 10.84 (1H, s)

MASS: 649 (M+1)

the other isomer

IR (Neat): 3400, 1730, 1630, 1520, 1345, 1275 cm$^{-1}$

NMR (DMSO-d$_6$, δ): 2.05–4.93 (10H, m); 3.69 (3H, s); 6.52–8.31 (12H, m); 10.80 (1H, s)

MASS: 649 (M+1)

Example 50–46)

$[\alpha]_D^{20}$: –98.5° (C=1.0, MeOH)

IR (Nujol): 3425, 3325, 1720, 1640, 1510, 1460, 1275 cm$^{-1}$

NMR (DMSO-d$_6$, δ): 1.9–4.85 (10H, m); 3.63 (3H, s); 5.15 (2H, s); 6.52–8.18 (12H, m); 10.8 (1H, s)

MASS: 619 (M+1)

Example 50–47)

$[\alpha]_D^{20}$: –64.3° (C=1.0, MeOH)

IR (Neat): 3400, 3250, 1730, 1625, 1510, 1330, 1275 cm$^{-1}$

NMR (DMSO-d$_6$, δ): 1.99 (3H, s); 2.0–5.20 (10H, m); 3.0 (3H, s); 6.52–8.19 (12H, m); 9.85 (1H, s);. 10.76 (1H, s)

MASS: 697 (M+1)

Example 50–48)

$[\alpha]_D^{20}$: –11.0° (C=1.0, MeOH)

IR (Nujol): 3350, 3150, 2650, 2450, 2300, 1635, 1270 cm$^{-1}$

NMR (DMSO-d$_6$, δ): 1.60–4.93 (26H, m); 6.60–8.66 (8H, m); 9.18 (1H, s) ; 10.87 (1H, s)

MASS: 639 (M+1)

Example 50–49)

IR (Nujol): 3200, 1626 cm$^{-1}$

NMR(DMSO-d$_6$, δ): 1.86–2.12 (7H, m); 2.34–2.59 (4H, m); 2.82–5.20 (15H, m); 6.60–8.28 (13H, m); 10.96 (1H, s); 10.87–11.35 (1H, m)

MASS: 699 (M+1) (free)

Example 50–50)

IR (Nujol): 3350–3210, 2550–2500, 1635 cm$^{-1}$

NMR (DMSO-d$_6$, δ): 1.76–2.20 (2H, m); 2.37–2.66 (2H, m); 2.80–5.20 (19H, m); 6.59–8.30 (13H, m); 10.97 (1H, s); 10.87–11.55 (2H, m)

MASS: 686 (M+1) (free)

Example 50–51)

IR (Nujol): 3350–3250, 2580, 1630 cm$^{-1}$

NMR (DMSO-d$_6$, δ): 0.95–2.20 (12H, m); 2.76–5.20 (22H, m); 6.54–8.30 (8H, m); 10.96 (1H, s) ; 10.79–11.17 (1H, m); 11.42 (1H, br s)

MASS: 692 (M+1) (free)

Example 50–52)

IR (Neat): 3330, 2680, 1630, 1540 cm$^{-1}$

NMR (DMSO-d$_6$, δ): 1.75–2.37 (4H, m); 2.76, 2.78 (6H, 2 s); 2.92–5.20 (15H, m); 6.55–8.47 (9H, m); 10.37 (1H, br s); 10.97 (1H, s); 11.15–11.57 (1H, br s)

MASS: 612 (M+1) (free)

Example 50–53)

IR (Nujol): 3200, 1626 cm$^{-1}$

NMR (DMSO-d$_6$, δ): 1.20–1.67 (6H, m); 1.72–2.12 (2H, m); 2.23–2.52 (2H, m); 2.75–5.18 (15H, m)); 6.57–8.27 (8H, m); 10.95 (1H, s); 10.80–11.36 (1H, m)

MASS: 609 (M+1) (free)

Example 50–54)

IR (Nujol): 3350–3230, 1640 cm$^{-1}$

NMR (DMSO-d$_6$, δ): 1.92–2.14 (2H, m); 2.44–2.66 (2H, m); 2.96–5.20(19H, m); 6.57–8.26 (12H, m); 10.97 (1H, s); 10.88–11.04 (2H, m); 11.36–11.65 (1H, m)

MASS: 687 (M+1) (free)

Example 50–55)

IR (Nujol): 3400–3220, 2550, 1625 cm$^{-1}$

NMR (DMSO-d$_6$, δ): 1.29–2.26 (6H, m); 2.38–5.22 (18H, m); 6.58–8.30 (13H, m); 10.96 (1H, s); 10.79–11.30 (1H, m)

MASS: 685 (M+1) (free)

Example 50–56)

IR (Neat): 3260, 2990, 2810, 1625 cm$^{-1}$

NMR (DMSO-d$_6$, δ): 1.47–2.22 (9H, m); 2.58–4.96 (14H, m); 6.56–8.26 (23H, m); 10.85 (1H, s)

MASS: 852 (M+1)

Example 50-57)

IR (Nujol): 3330, 2700, 1630 cm$^{-1}$

NMR (DMSO-d$_6$, δ): 1.80–2.23 (2H, m); 2.33–2.66 (2H, m); 2.90–5.20 (19H, m)); 6.55–8.28 (8H, m); 9.20–9.80 (2H, m); 10.97 (1H, s); 10.86–11.63 (1H, m)

MASS: 610 (M+1) (free)

Example 50-58)

mp: 180°–185° C.

$[\alpha]_D^{30}$: −21.3° (C=1.0, MeOH)

Example 51

The following piperazine derivatives (Table 2) were prepared by the similar manner to that of the each Example No. defined in the "Process" column. The physical properties of the object compounds are shown after the table.

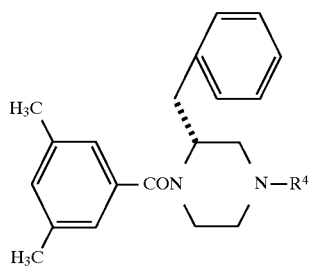

TABLE 2

| Example No. | Object Compounds R$^4$ | Salt | Starting Compound | Process |
|---|---|---|---|---|
| 51-1) | —CH$_2$—C$_6$H$_5$ | — | Pr. 8-2) | Ex. 1 |
| 51-2) | —CH$_2$—C$_6$H$_5$ | HCl | Ex. 51-1) | Ex. 23 |
| 51-3) | —CH$_2$—C$_6$H$_4$—F | — | Ex. 51-6) | Ex. 11 |
| 51-4) | —CH$_2$—C$_6$H$_4$—F | HCl | Ex. 51-3) | Ex. 23 |
| 51-5) | —CO(CH$_2$)$_2$—C$_6$H$_5$ | — | Ex. 51-6) | Ex. 16 |
| 51-6) | —H | — | Ex. 51-1) | Ex. 6 |

TABLE 2-continued

| Example No. | Object Compounds R$^4$ | Salt | Starting Compound | Process |
|---|---|---|---|---|
| 51-7) | —(CH$_2$)$_2$—C$_6$H$_5$ | HCl | Ex. 68 | Ex. 23 |
| 51-8) | —CH$_2$-naphthyl | — | Ex. 51-6) | Ex. 11 |
| 51-9) | —CH$_2$-naphthyl | HCl | Ex. 51-8) | Ex. 23 |
| 51-10) | —CH$_2$—C$_6$H$_3$(CF$_3$)$_2$ | — | Ex. 51-6) | Ex. 11 |
| 51-11) | —CH$_2$—C$_6$H$_3$(CF$_3$)$_2$ | HCl | Ex. 51-10) | Ex. 23 |

Physical properties of the compounds of the Example 51:

Example 51–1)

IR (Neat): 3020, 2910, 2810, 1638–1628, 1600 cm$^{-1}$

NMR (DMSO-d$_6$, δ): 1.87–4.78 (11H, m); 2.21 (6H, s); 6.36–7.46 (13H, m)

MASS: 399 (M+1)

Example 51–2)

IR (Nujol): 3370, 2600–2300, 1640–1628, 1598 cm$^{-1}$

NMR (DMSO-d$_6$, δ): 2.23 (6H, s); 2.76–5.07 (11H, m); 6.42–7.76 (13H, m); 11.37 (1H, br s)

MASS: 399 (M+1) (free)

Example 51–3)

IR (Neat): 3430, 2920, 2800, 1624, 1600, 1507 cm$^{-1}$

NMR (DMSO-d$_6$, δ): 2.22 (6H, s); 1.94–4.80 (11H, m); 6.36–7.45 (12H, m)

MASS: 417 (M+1)

Example 51–4)

IR (Nujol): 3360, 2560, 1626, 1598, 1510 cm$^{-1}$

NMR (DMSO-d$_6$, δ): 2.23 (6H, s); 2.73–5.11 (11H, m); 6.40–7.90 (12H, m); 11.45 (1H, br s)

MASS: 417 (M+1) (free)

Example 51–5)

IR (Neat): 3450, 3020, 2990, 2920, 2860, 1637–1620, 1598 cm$^{-1}$

NMR (DMSO-d$_6$, δ): 2.21 (6H, m); 2.25–4.48 (13H, m); 6.11–7.45 (13H, m)

MASS: 441 (M+1)

Example 51-6)

IR (Neat): 3310, 2850–2800, 1620, 1596 cm$^{-1}$

NMR (DMSO-d$_6$, δ): 2.21 (6H, s); 2.50–4.90 (10H, m); 6.25–7.52 (8H, m)

MASS: 309 (M+1)

Example 51-7)

IR (Neat): 3380, 2930, 2410, 1633, 1599 cm$^{-1}$

NMR (DMSO-d$_6$, δ): 2.21 (6H, s); 2.94–5.22 (13H, m); 6.32–7.52 (13H, m); 11.34 (1H, br s)

MASS: 413 (M+1) (free)

Example 51-8)

IR (Neat): 2920, 2810, 1629, 1600 cm$^{-1}$

NMR (DMSO-d$_6$, δ): 2.21 (6H, s); 1.90–4.82 (9H, m); 3.48 (1H, d, J=13.3 Hz); 3.78 (1H, d, J=13.0 Hz); 6.35–8.02 (15H, m)

MASS: 449 (M+1)

Example 51-9)

IR (Nujol): 3370, 2560, 1625 cm$^{-1}$

NMR (DMSO-d$_6$, δ): 2.22 (6H, s); 2.79–5.05 (11H, m); 6.41–8.24 (15H, m); 11.47 (1H, br s)

MASS: 449 (M+1) (free)

Example 51-10)

IR (Neat): 3420, 2920, 2810, 1626, 1600 cm$^{-1}$

NMR (DMSO-d$_6$, δ): 2.21 (6H, s); 1.94–4.85 (11H, m); 6.32–7.20 (8H, m); 8.06 (3H, s)

MASS: 535 (M+1)

Example 51-11)

IR (Neat): 3400, 2940, 2400, 1632, 1600 cm$^{-1}$

NMR (DMSO-d$_6$, δ): 2.24 (6H, s);. 2.78–5.11 (11H, m); 6.46–7.34 (8H, m); 8.24 (1H, s); 8.50 (2H, s); 11.89 (1H, br s)

MASS: 535 (M+1) (free)

Example 52

The following piperazine derivatives (Table 3) were prepared by the similar manner to that of the each Example No. defined in the "Process" column. The physical properties of the object compounds are shown after the table.

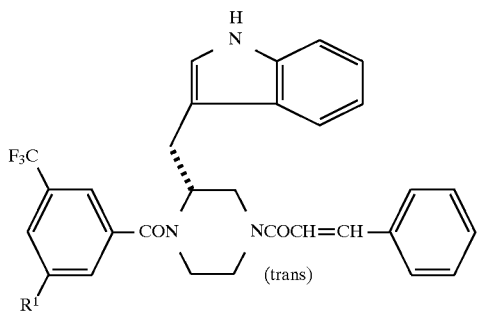

TABLE 3

| Example No. | Object Compounds R$^1$ | Salt | Starting Compound | Process |
|---|---|---|---|---|
| 52-1) | —NO$_2$ | — | Pr. 17 | Ex. 1 |
| 52-2) | —NHCHO | — | Pr. 17 | Ex. 1 |
| 52-3) | —N(CH$_3$)(CHO) | — | Pr. 17 | Ex. 1 |
| 52-4) | —N(CH$_3$)$_2$ | — | Pr. 17 | Ex. 1 |
| 52-5) | —NHSO$_2$CH$_3$ | — | Ex. 52-6) | Ex. 40 |
| 52-6) | —NHCOCH$_3$ | — | Ex. 64 | Ex. 40 |
| 52-7) | —NHCH$_3$ | — | Ex. 52-3) | Ex. 64 |

Physical properties of the compounds of the Example 52:

Example 52-1)

[α]$_D^{18}$: +8.7° (C=1.0, MeOH)

IR (Neat): 3260, 1635, 1540, 1420, 1310 cm$^{-1}$

NMR (DMSO-d$_6$, δ): 2.74–5.07 (11H, m); 6.57–8.59 (13H, m); 10.91(1H, s)

MASS: 563 (M+1)

Example 52-2)

[α]$_D^{19}$: -25.1° (C=1.0, MeOH)

IR (Neat): 3250, 1690, 1640, 1600, 1430, 1340–1270 cm$^{-1}$

NMR (DMSO-d$_6$, δ): 2.85–5.13 (11H, m); 6.57–8.44 (9H, m); 10.33–10.96 (2H, m)

MASS: 561 (M+1)

Example 52-3)

[α]$_D^{18}$: -33.4° (C=1.0, MeOH)

IR (Neat): 3250, 1675, 1635, 1600, 1430 cm$^{-1}$

NMR (DMSO-d$_6$, δ): 2.89–5.13 (14H, m); 6.6–8.69 (14H, m); 10.86 (1H, s)

MASS: 575 (M+1)

Example 52-4)

[α]$_D^{18}$: +10.1° (C=1.0, MeOH)

IR (Neat): 3250, 1640, 1600, 1490, 1425 cm$^{-1}$

NMR (DMSO-d$_6$, δ): 2.83–5.14 (11H, m); 2.94 (6H, s); 6.52–7.84 (13H, m); 10.85 (1H, s)

Example 52-5)

[α]$_D^{18}$: -43.7° (C=1.0, MeOH)

IR (Neat): 3400, 3250, 1640, 1600, 1430, 1330 cm$^{-1}$

NMR (DMSO-d$_6$, δ): 2.86–5.10 (11H, m); 3.0 (3H, s); 6.64–7.88 (12H, m); 10.2–10.4 (1H, m); 10.85 (1H, s)

MASS: 611 (M+1)

Example 52-6)

[α]$_D^{18}$: -27.2° (C=1.0, MeOH)

IR (Neat): 3275, 1680, 1640, 1600, 1560, 1425 cm$^{-1}$

NMR (DMSO-d$_6$, δ): 2.08 (3H, s); 2.8–5.09 (11H, s); 6.6–8.11 (14H, m); 10.83 (1H, s)

MASS: 575 (M+1)

Example 52-7)

IR (Neat): 3300, 1640, 1600, 1460, 1420 cm$^{-1}$

NMR (DMSO-d$_6$, δ): 2.64–5.1 (14H, m); 6.55–7.83 (14H, m); 10.85 (1H, s)

MASS: 547 (M+1)

Example 53

The following piperazine derivatives (Table 4) were prepared by the similar manner to that of the each Example No. defined in the "Process" column. The physical properties of the object compounds are shown after the table.

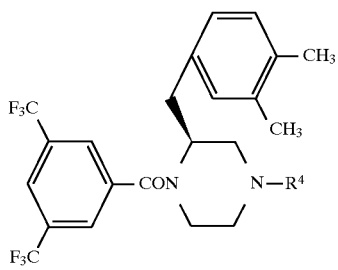

TABLE 4

| Example No. | Object Compounds R$^4$ | Salt | Starting Compound | Process |
|---|---|---|---|---|
| 53-1) | —COCH=CH—⌬—F (trans) | — | Ex. 53-4) | Ex. 16 |
| 53-2) | —COCH=CH—⌬(N) (trans) | HCl | Ex. 73 | Ex. 23 |
| 53-3) | —CH$_2$—⌬—F | — | Pr. 8-6) | Ex. 1 |
| 53-4) | —H | — | Ex. 53-3) | Ex. 6 |
| 53-5) | —H | HCl | Ex. 53-4) | Ex. 23 |

Physical properties of the compounds of the Example 53:

Example 53-1)

[α]$_D^{20}$: +2.57° (C=1.0, MeOH)

IR (Nujol): 1639, 1596, 1505 cm$^{-1}$

NMR (CDCl$_3$, δ): 2.13 (3H, s); 2.22 (3H, s); 2.55–5.39 (9H, m); 6.46–7.98 (12H, m)

MASS: 593 (M+1)

Example 53-2)

[α]$_D^{17}$: +1.8° (C=1.0, MeOH)

IR (Nujol): 3380, 1635, 1607 cm$^{-1}$

NMR (DMSO-d$_6$, δ): 2.03, 2.08, 2.17 (6H, 3 s); 2.50–5.05 (9H, m); 5.53 (1H, br s); 6.49–9.34 (12H, m)

MASS: 576 (M+1) (free)

Example 53-3)

IR (Neat): 3020, 2920, 2800, 2760, 1636 cm$^{-1}$

NMR (CDCl$_3$, δ): 2.20 (6H, s); 1.94–5.09 (11H, m); 6.45–7.90 (11H, m)

MASS: 535 (M+1)

Example 53-4)

IR (Neat): 3310, 2920, 1635–1627 cm$^{-1}$

NMR (CDCl$_3$, δ): 1.63 (1H, s); 2.22 (6H, s); 2.04–5.17 (9H, m); 6.54–7.88 (6H, m)

MASS: 445 (M+1)

Example 53-5)

mp: >130° C. (C=1.0, MeOH)

[α]$_D^{20}$: +31.27° (C=1.0, MeOH)

IR (Nujol): 3390, 1636 cm$^{-1}$

NMR (DMSO-d$_6$, δ): 2.11, 2.18(6H, 2 s); 2.62–4.66 (9H, m); 6.56–8.23 (6H, m); 9.61 (2H, m)

MASS: 445 (M+1) (free)

Example 54

The following piperazine derivatives (Table 5) were prepared by the similar manner to that of the each Example No. defined in the "Process" column. The physical properties of the object compounds are shown after the table.

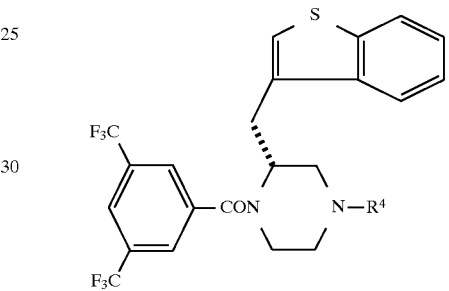

TABLE 5

| Example No. | Object Compounds R$^4$ | Salt | Starting Compound | Process |
|---|---|---|---|---|
| 54-1) | —CH$_2$—⌬ | — | Pr. 8-5) | Ex. 1 |
| 54-2) | —CH$_2$—⌬ | HCl | Ex. 54-1) | Ex. 23 |
| 54-3) | —H | — | Ex. 54-1) | Ex. 6 |
| 54-4) | —COCH=CH—⌬ (trans) | — | Ex. 69 | Ex. 16 |
| 54-5) | —(CH$_2$)$_3$—⌬ | HCl | Ex. 54-3) | Ex. 11 |

Physical properties of the compounds of the Example 54

Example 54-1)

IR (Neat): 3100–2700, 1635, 1490, 1430, 1380, 1350 cm$^{-1}$

NMR (CDCl₃, δ): 2.0–2.4 (2H, m); 2.8–3.8 (8H, m); 4.0–5.2 (1H, m); 6.8–8.2 (13H, m)

MASS: 563 (M+1)

Example 54–2)

mp: 150°–165° C.

IR (Nujol): 3400, 2200–2700, 1635, 1440, 1360 cm⁻¹

NMR (DMSO-d₆, δ): 3.0–4.3 (9H,.m); 4.5–5.2 (2H, m); 6.9–7.3 (2H, m); 7.4–8.3 (10H, m)

MASS: 563 (M+1) (free)

Example 54–3)

IR (Neat): 3300, 2700–3100, 1630, 1430, 1370, 1350 cm⁻¹

MASS: 473 (M+1)

Example 54–4)

mp: 60°–63° C.

$[\alpha]_D^{23}$: –25.2° (C=1.0, MeOH)

IR (Nujol): 1635, 1605, 1450, 1350, 1315 cm⁻¹

NMR (CDCl₃, δ): 2.8–5.4 (9H, m); 6.8–8.3 (15H, m)

MASS: 603 (M+1), 575, 473

Example 54–5)

mp: 124°–130° C. (dec.)

$[\alpha]_D^{20}$: +4.0° (C=0.05, MeOH)

IR (Nujol): 3300, 2300–2600, 1635, 1430, 1360 cm⁻¹

NMR (DMSO-d₆, δ): 2.0–2.3 (2H, m); 2.6–2.8 (2H, m); 3.0–4.0 (11H, m); 4.2–5.3 (1H, m); 7.0–7.6 (9H, m); 7.8–8.4 (4H, m); 11.0–11.6 (1H, m)

MASS: 591 (M+1), 563

Example 55

The following piperazine derivatives (Table 6) were prepared by the similar manner to that of the each Example No. defined in the "Process" column. The physical properties of the object compounds are shown after the table.

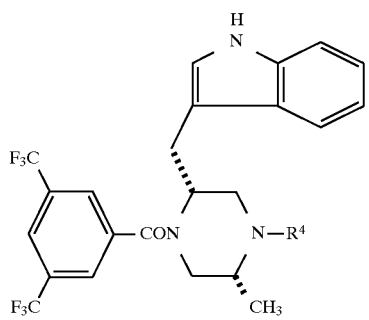

TABLE 6

| Example No. | Object Compounds R⁴ | Salt | Starting Compound | Process |
|---|---|---|---|---|
| 55-1) | —CH₂—C₆H₅ | — | Pr. 8-8) | Ex. 1 |
| 55-2) | —H | — | Ex. 55-1) | Ex. 6 |
| 55-3) | —COCH=CH—(pyridyl) (trans) | — | Ex. 55-2) | Ex. 16 |
| 55-4) | —COCH=CH—C₆H₄—F (trans) | — | Ex. 55-2) | Ex. 16 |
| 55-5) | —CO—C₆H₄—COCH₃ | — | Ex. 55-2) | Ex. 16 |

Physical properties of the compounds of the Example 55

Example 55–1)

$[\alpha]_D^{19}$: –43.2° (C=1.0, MeOH)

IR (Neat): 3400, 3300, 1630, 1440, 1275 cm⁻¹

NMR (DMSO-d₆, δ): 1.09–1.32 (3H, m); 2.35–4.8 (10H, m); 6.53–8.45 (10H, m); 10.69 (1H, s)

MASS: 560 (M+1)

Example 55–2)

mp: 157°–159° C.

IR (Nujol): 3260, 1625, 1600, 1460, 1280 cm⁻¹

NMR (DMSO-d₆, δ): 9.3–1.18 (3H, m); 2.6–4.85 (8H, m); 6.65–8.4 (9H, m); 10.86 (1H, s)

MASS: 470 (M+1)

Example 55–3)

$[\alpha]_D^{19}$: –107.3° (C=1.0, MeOH)

IR (Neat): 3250, 1630, 1610, 1430, 1340, 1280 cm⁻¹

NMR (DMSO-d₆, δ): 0.86–1.4 (3H, m); 2.88–5.16 (10H, m); 6.6–8.86 (12H, m); 10.92 (1H, d, J=14 Hz)

MASS: 601 (M+1)

Example 55–4)

$[\alpha]_D^{18}$: –127.1° (C=1.0, MeOH)

IR (Neat): 3260, 1630, 1595, 1510, 1420, 1340, 1275 cm⁻¹

NMR (DMSO-d₆, δ): 0.9–1.4 (3H, m); 2.72–4.72 (10H, m); 6.86–8.27 (12H, m); 10.94 (1H, br s)

MASS: 618 (M+1)

Example 55–5)

$[\alpha]_D^{20}$: –107.5° (C=1.0, MeOH)

IR (Neat): 3260, 1680, 1625, 1425, 1350, 1275 cm⁻¹

NMR (DMSO-d₆, δ): 0.9–1.2 (3H, m); 2.56 (3H, s); 2.7–4.9 (8H, m); 6.86–8.2 (12H, m); 10.8 (1H, s)

MASS: 616 (M+1)

Example 56

The following piperazine derivatives (Table 7) were prepared by the similar manner to that of the each Example No. defined in the "Process" column. The physical properties of the object compounds are shown after the table.

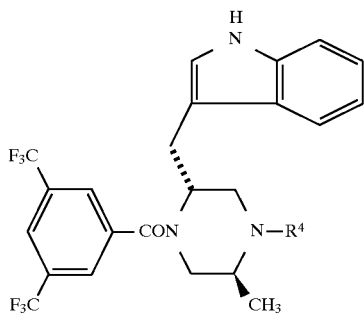

TABLE 7

| Example No. | Object Compounds R⁴ | | Salt | Starting Compound | Process |
|---|---|---|---|---|---|
| 56-1) | —CH₂— (phenyl) | | — | Pr. 8-9) | Ex. 1 |
| 56-2) | —H | | — | Ex. 56-1) | Ex. 6 |
| 56-3) | —COCH=CH— (pyridyl) (trans) | | — | Ex. 56-2) | Ex. 16 |
| 56-4) | —CH₂COOCH₃ | | — | Ex. 56-2) | Ex. 11 |
| 56-5) | —CH₂CONH₂ | | — | Ex. 56-4) | Ex. 9 |

Physical properties of the compounds of the Example 56

Example 56-1)

$[\alpha]_D^{19}$: −9.6° (C=1.0, MeOH)

IR (Neat): 3250, 1655, 1625, 1430, 1275 cm$^{-1}$

NMR (DMSO-d$_6$, δ): 1.12 (3H, d, J=7 Hz); 2.35–4.82 (10H, m); 6.57–8.40 (10H, m); 10.74 (1H, s)

MASS: 560 (M+1)

Example 56-2)

IR (Neat): 3250, 1620, 1430, 1350, 1275 cm$^{-1}$

NMR (DMSO-d$_6$, δ): 1.13 (3H, s); 1.68–3.55 (8H, m); 4.46 (1H. br s); 6.72–8.48 (8H, m); 10.86 (1H, s)

MASS: 470 (M+1)

Example 56-3):

$[\alpha]_D^{19}$: +27.0° (C=1.0, MeOH)

IR (Neat): 3250, 1640, 1430, 1280 cm$^{-1}$

NMR (DMSO-d$_6$, δ): 1.1–1.4 (3H, m); 2.8–5.1 (10H, m); 6.6–8.94 (12H, m); 10.90 (1H, d, J=14 Hz)

MASS: 601 (M+1)

Example 56-4)

IR (Neat): 3300, 1740, 1670, 1625, 1435, 1275 cm$^{-1}$

NMR (DMSO-d$_6$, δ): 0.8–1.1 (3H, m); 2.6–4.8 (8H, m); 2.89 (3H, s); 3.70 (2H, s); 6.44–8.56 (8H, m); 10.84 (1H, s)

MASS: 542 (M+1)

Example 56-5)

mp: 245°–247° C.

$[\alpha]_D^{18}$: +3.1° (C=1.0, MeOH)

IR (Nujol): 3425, 3300, 3150, 1675, 1625, 1460, 1270 cm$^{-1}$

NMR (DMSO-d$_6$, δ): 0.8–1.1 (3H, m); 2.41–4.86 (10H, m); 6.57–8.22 (8H, m); 10.84 (1H, s)

MASS: 527 (M+1)

Example 57

The following piperazine derivatives (Table 8) were prepared by the similar manner to that of the each Example No. defined in the "Process" column. The physical properties of the object compounds are shown after the table.

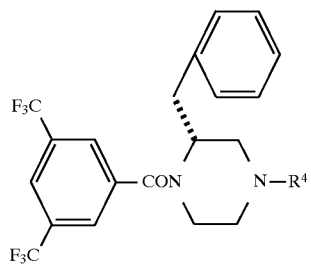

TABLE 8

| Example No. | Object Compounds R⁴ | Salt | Starting Compound | Process |
|---|---|---|---|---|
| 57-1) | (cyclopentyl-OH)—N—COO—C(CH₃)₃ | — | Ex. 7-7) | Ex. 61 |

TABLE 8-continued

| Example No. | Object Compounds R⁴ | Salt | Starting Compound | Process |
|---|---|---|---|---|
| 57-2) | —(CH₂)₃—⟨H⟩ | HCl | Ex. 7-7) | Ex. 14 |

Physical properties of the compounds of the Example 57

Example 57–1)

IR (Neat): 3380, 2960, 2920, 1678, 1634 cm$^{-1}$

NMR (DMSO-d$_6$, δ): 1.38, 1.42, 1.47 (9H, 3 s); 1.76–2.34 (2H, m); 2.55–5.20 (14H, m); 6.86–8.31 (8H, m)

MASS: 630 (M+1)

Example 57–2)

mp: 206°–208° C.

$[\alpha]_D^{22}$: -0.5° (C=10, MeOH)

IR (Nujol): 3600–3100, 2750–2100, 1641, 1274, 1134, 907 cm$^{-1}$

NMR (DMSO-d$_6$, δ): 0.80–1.00 (2H, m); 1.05–1.40 (6H, m); 1.60–1.95 (7H, m); 2.80–5.20 (11H, m); 6.90–7.70 (7H, m); 8.17–8.22 (1H, m)

MASS: 541 (M+1)

Example 58

The following piperazine derivatives (Table 9) were prepared by the similar manner to that of the each Example No. defined in the "Process" column. The physical properties of the object compounds are shown after the table.

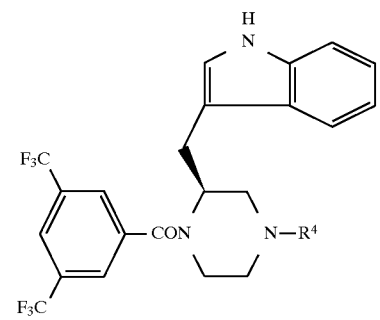

TABLE 9

| Example No. | Object Compounds R⁴ | Salt | Starting Compound | Process |
|---|---|---|---|---|
| 58-1) | —COCH=CH—⟨⟩ (trans) | — | Ex. 7-8) | Ex. 20 |
| 58-2) | —CH₂CONH₂ | — | Ex. 58-3) | Ex. 9 |
| 58-3) | —CH₂COOCH₃ | — | Ex. 7-8) | Ex. 11 |

Physical properties of the compounds of the Example 58

Example 58–1)

$[\alpha]_D^{26}$: +32.1° (C=1.0, MeOH)

IR (Film): 3275, 1635, 1430 cm$^{-1}$

NMR (DMSO-d$_6$, δ): 2.8–5.1 (9H, m); 6.6–8.2 (15H, m); 10.9 (1H, s)

MASS: 586 (M+1)

Example 58–2)

mp: >240° C.

$[\alpha]_D^{18}$: +5.8° (C=1.0, MeOH)

IR (Nujol): 3440, 3300, 3150, 1675, 1625, 1460, 1270 cm$^{-1}$

NMR (DMSO-d$_6$, δ): 2.09–4.93 (11H, m); 6.67–8.24 (8H, m); 10.83 (1H, s)

MASS: 513 (M+1)

Example 58–3)

IR (Neat): 3300. 1740, 1625, 1435, 1275 cm$^{-1}$

NMR (DMSO-d$_6$, δ): 2.28–4.91 (9H, mn); 2.51 (3H, s); 3.64 (2H, s); 6.6–8.2 (8H, m); 10.85 (1H, s)

MASS: 528 (M+1)

Example 59

The following piperazine derivatives (Table 10) were prepared by the similar manner to that of the each Example No. defined in the "Process" column. The physical properties of the object compounds are shown after the table.

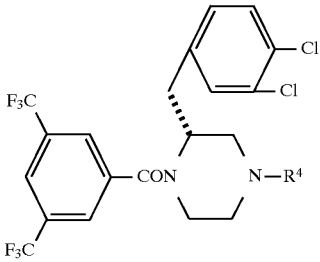

TABLE 10

| Example No. | Object Compounds R⁴ | Salt | Starting Compound | Process |
|---|---|---|---|---|
| 59-1) | —CH₂—⟨⟩ | — | Pr. 8-4) | Ex. 1 |
| 59-2) | —CH₂—⟨⟩ | HCl | Ex. 59-1) | Ex. 23 |

TABLE 10-continued

| Example No. | Object Compounds | | Starting | |
|---|---|---|---|---|
| | R⁴ | Salt | Compound | Process |
| 59-3) | —H | HCl | Ex. 59-1) | Ex. 69 |

Physical properties of the compounds of the Example 59

Example 59-1)

IR (Neat): 3100–2700, 1635, 1470, 1430 cm$^{-1}$
NMR (CDCl$_3$, δ): 2.0–2.3 (2H, m); 2.6–3.8 (8H, m); 4.5–5.0 (1H, m); 6.5–8.0 (11H, m)
MASS: 575 (M), 541

Example 59-2)

mp: 209°–211° C.
$[\alpha]_D^{27}$: +0.4° (C=1.0, MeOH)
IR (Nujol): 3400, 2600–2300, 1640, 1620, 1270 cm$^{-1}$
NMR (DMSO-d$_6$, δ): 2.8–5.1 (11H, m); 6.8–7.7 (9H, m); 7.8–7.9 (1H, m); 8.2–8.3 (1H, m); 11.4–11.8 (1H, m)
MASS: 575 (M) (free)

Example 59-3)

mp: 245°–247° C.
$[\alpha]_D^{24}$: −9.6° (C=1.0, MeOH)
IR (Nujol): 3500, 2800–2500, 1650, 1610, 1590, 1450, 1360, 1330, 1310 cm$^{-1}$
NMR (DMSO-d$_6$, δ): 2.6–5.2 (9H, m); 6.8–7.9 (5H, m); 8.21 (1H, s); 9.4–10.2 (2H, m)
MASS: 485 (M) (free)

Example 60

The following piperazine derivatives (Table 11) were prepared by the similar manner to that of the each Example No. defined in the "Process" column. The physical properties of the object compounds are shown after the table.

TABLE 11

| Example No. | Object Cmpounds | Salt | Starting Compound | Process |
|---|---|---|---|---|
| 60-1) | 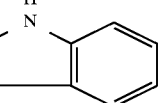 | — | Ex. 4-5) | Ex. 6 |
| 60-2) |  | — | Ex. 4-6) | Ex. 6 |
| 60-3) | 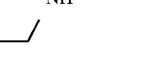 | — | Pr. 8-7) | Ex. 1 |

TABLE 11-continued

| Example No. | Object Cmpounds | Salt | Starting Compound | Process |
|---|---|---|---|---|
| 60-4) | (structure with N-methylindole, CH3, F3C/F3C-benzoyl, piperazine, N-CH2-phenyl) | HCl | Ex. 60-3) | Ex. 23 |
| 60-5) | (structure with benzyl, 3,5-dimethylbenzoyl, piperazine, N-(CH2)3-phenyl) | — | Pr. 8-11) | Ex. 1 |
| 60-6) | (structure with benzyl, 3,5-dimethylbenzoyl, piperazine, N-(CH2)3-phenyl) | HCl | Ex. 60-5) | Ex. 23 |
| 60-7) | (structure with 3,4-dimethylbenzyl, 3,5-bis(trifluoromethyl)benzoyl, piperazine, N-CH2-thiazole-NH2) | 2HCl | Ex. 7-1) | Ex. 14 |
| 60-8) | (structure with naphthylmethyl, 3,5-dimethylbenzoyl, piperazine, N-CH2-phenyl) | — | Pr. 8-10) | Ex. 61 |

Physical properties of the compounds of the Example 60

Example 60–1)

IR (Nujol): 3200, 1620, 1610, 1320 cm$^{-1}$

NMR (DMSO-d$_6$, δ): 2.4–4.9 (9H, m); 6.7–8.1 (8H, m); 10.8 (1H, s); 10.87 (1H, s)

MASS: 456 (M+1)

Example 60–2)

$[α]_D^{25}$: +54.1° (C=1.0, MeOH)

IR (Film): 3250, 1620, 1430, 1340 cm$^{-1}$

NMR (DMSO-d$_6$, δ): 2.1–4.8 (9H, m); 6.3–8.3 (8H, m); 10.88 (1H, s); 10.93 (1H, s)

MASS: 456 (M+1)

Example 60–3)

IR (Neat): 3100–2700 (m), 1640, 1440, 1380, 1350 cm$^{-1}$

NMR (CDCl$_3$, δ): 1.1–1.4 (3H, m); 1.6–1.8 (1H, m); 1.8–2.0 (1H, m); 2.2–2.4 (1H, m); 2.7–3.0 (1H, m); 3.1–5.0 (6H, m); 3.61 (3H, s); 6.8–8.5 (13H, m)

MASS: 574 (M+1)

Example 60–4)

mp: 130°–131° C. (dec.)

$[α]_D^{23}$: −0.4° (C=0.5, MeOH)

IR (Nujol): 3350, 2700–2400, 1640, 1450, 1350 cm$^{-1}$

NMR (DMSO-d$_6$, δ): 1.0–1.4 (3H, m); 3.0–5.1 (10H, m); 3.65 (3H, s); 6.6–8.5 (13H, m); 11.2–11.6 (1H, m)

Example 60–5)

IR (CHCl$_3$): 3450, 3060, 3020, 2940, 2860, 2800, 2760, 1628, 1600 cm$^{-1}$

NMR (DMSO-d$_6$, δ): 1.73 (2H, m); 1.85–2.05 (2H, m); 2.20 (6H, s); 2.15–2.45 (2H, m); 2.60–3.50 (8H, m); 3.60–3.80, 4.25–4.45, 4.70–4.90 (1H, m); 6.34, 6.71, 6.80–7.40 (13H, m)

MASS: 427 (M+1)

Example 60–6)

$[α]_D^{23}$: −26.82° (C=1.0, CHCl$_3$)

IR (Nujol): 3370, 2380, 1625, 1598 cm$^{-1}$

NMR (DMSO-d$_6$, δ): 2.19, 2.24 (6H, s); 1.95–2.35 (2H, m); 2.55–2.75 (2H, m); 2.85–3.75, 3.85–4.05, 4.45–4.65, 4.95–5.15 (11H, m); 6.38, 6.71, 6.80–7.45 (13H, m); 11.18 (1H, br s)

MASS: 427 (M+1) (free)

Example 60–7)

mp: 190°–210° C. (dec.)

$[α]_D^{20}$: −14.6° (C=0.5, MeOH)

IR (Nujol): 2700–2200, 1630, 1500, 1350 cm$^{-1}$

NMR (DMSO-d$_6$, δ): 2.07, 2.17 (6H, 2 s); 2.8–5.4 (15H, m); 6.5–6.7 (1H, m), 6.8–7.2 (2H, m); 7.14 (1H, s); 7.54 (1H, s); 7.76 (1H, s); 8.20 (1H, s)

MASS: 557 (M+1) (free), 445

Example 60–8)

mp: 108°–109° C.

IR (Nujol): 1625, 1600, 1450, 1370, 1300 cm$^{-1}$

NMR (DMSO-d$_6$, δ): 2.0–3.6 (10H, m); 3.8–4.0 (1H, m); 6.8–7.8 (15H, m)

MASS: 449 (M+1)

Example 61

To a stirred mixture of 4-(dimethylamino)butyric acid hydrochloride (70 mg) and 1-hydroxybenzotriazole hydrate (160 mg) in dichloromethane (10 ml) was added 1-(3-dimethylaminopropyl)-3-ethylcarbodiimide hydrochloride (80 mg) under ice cooling. After stirring for 30 minutes, a solution of (2R)-1-[3,5-bis(trifluoromethyl)benzoyl]-2-(1H-indol-3-yl-methyl)piperazine (200 mg) in dichloromethane (5 ml) was added at the same temperature. The resulting mixture was stirred for 2.5 hours at room temperature. Dichloromethane and aqueous sodium bicarbonate solution were added to the reaction mixture and then the organic layer was separated and dried over magnesium sulfate. Evaporation of the solvent in vacuo gave (2R)-1-[3,5-bis (trifluoromethyl)benzoyl]-4-[4-(dimethylamino)butyryl]-2-(1H-indol-3-yl-methyl)piperazine (0.25 g).

IR (Neat): 3270, 2920, 2860, 2820, 2770, 1630 cm$^{-1}$

NMR (DMSO-d$_6$, δ): 1.52–1.83 (2H, m); 2.09, 2.10, 2.13 (6H, 3 s); 2.00–5.10 (13H, m); 6.53–8.25 (8H, m); 10.89 (1H, s)

MASS: 569 (M+1)

Example 62

Cyclohexyl isocyanate (0.06 ml) was added to a stirred solution of (2R)-1-[3,5-bis(trifluoromethyl)-benzoyl]-2-(1H-indol-3-yl-methyl)piperazine (0.2 g) in dichloromethane (10 ml) at room temperature. After stirring for 4 hours, dichloromethane (10 ml) and water (5 ml) were added. The organic layer was separated, washed with brine and dried over magnesium sulfate. After evaporation of the solvent in vacuo, the residue was purified by column chromatography on silica gel, eluting with a mixture of dichloromethane and methanol (98:2) to give (2R)-1-[3,5-bis (trifluoromethyl)benzoyl]-4-cyclohexylcarbamoyl-2-(1H-indol-3-yl-methyl)piperazine (0.18 g).

IR (Neat): 3280, 2920, 2840, 1622, 1525 cm$^{-1}$

NMR (DMSO-d$_6$, δ): 1.00–1.90 (10H, m); 2.76–4.90 (10H, m); 6.13–8.23 (9H, m); 10.87 (1H, s)

MASS: 581 (M+1)

Example 63

To a stirred solution of (2R)-1-[3,5-bis(trifluoromethyl) benzoyl]-2-(1H-indol-3-yl-methyl)piperazine (400 mg) in dichloromethane (5 ml) was added 1,1'-carbonyldiimidazole (140 mg) at room temperature. The resulting mixture was stirred overnight. Additional 1,1'-carbonyldiimidazole (70 mg) was added to the mixture and then stirred for 1 hour. After the dichloromethane was removed under reduced pressure, N-methylpropylamine (1 g) was added. The mixture was stirred at room temperature for 2 hours and then at reflux temperature for 12 hours. After cooling, dichloromethane and water were added to the reaction mixture. The organic layer was separated, washed with aqueous 0.5N hydrochloric acid and brine. After evaporation of the solvent, the residue was purified by column chromatography on silica gel, eluting with a mixture of dichloromethane and methanol (99:1) to give (2R)-1-[3,5-bis(trifluoromethyl) benzoyl]-2-(1H-indol-3-yl-methyl)-4-(N-methyl-N-propylcarbamoyl)piperazine (0.18 g).

IR (Neat): 3260, 2950, 2910, 2850, 1628 cm$^{-1}$

NMR (DMSO-d$_6$, δ): 0.83 (3H, t, J=7.2 Hz); 1.38–1.67 (2H, m); 2.85 (3H, s); 2.69–5.04 (11H, m); 6.58–8.29 (8H, m).; 10.86 (1H, s)

MASS: 555 (M+1)

Example 64

A mixture of (2R)-4-(trans-cinnamoyl)-1-[3-formylamino-5-(trifluoromethyl)benzoyl]-2-(1H-indol-3-yl-methyl)piperazine (280 mg) and aqueous 10% hydrochloric acid (1 ml) in methanol (10 ml) was stirred at room temperature for 6 hours. The mixture was evaporated under reduced pressure. The resulting powder was collected by filtration and dried to give (2R)-1-[3-amino-5-(trifluoromethyl)-benzoyl]-4-(trans-cinnamoyl)-2-(1H-indol-3-yl-methyl)piperazine hydrochloride (280 mg).

[α]$_D^{18}$: -22.8° (C=1.0, MeOH)

IR (Neat): 3250, 2850, 2050, 1635, 1600, 1430, 1335 cm$^{-1}$

NMR (DMSO-d$_6$, δ): 2.78–5.54 (14H, m); 6.67–7.85 (13H, m); 10.89 (1H, s)

MASS: 533 (M+1) (free)

Example 65

Hydrochloric acid (0.22 ml) was added to a stirred mixture of (2R)-1-[3,5-bis(trifluoromethyl)benzoyl]-4-[N-(2-hydroxybenzylidene)-2-aminoethyl]-2-(1H-indol-3-yl-methyl)piperazine (0.80 g), ethyl acetate (12 ml) and methanol (6 ml) at room temperature. The mixture was stirred at 50° C. for 4.5 hours and then concentrated in vacuo to give an oil. The oil was treated with 4N hydrogen chloride in dioxane solution (0.33 ml) to afford (2R)-4-(2-aminoethyl)-1-[3,5-bis(trifluoromethyl)benzoyl]-2-(1H-indol-3-yl-methyl)piperazine dihydrochloride (0.57 g).

IR (Neat): 3340, 2930, 1625 cm$^{-1}$

NMR (DMSO-d$_6$, δ): 2.92–5.20 (13H, m); 6.48–8.85 (11H, m); 10.98 (1H, s); 11.52–11.90 (1H, m)

MASS: 499 (M+1) (free)

Example 66

Sodium azide (0.21 g) was added to a stirred mixture of (2R)-1-[3,5-bis(trifluoromethyl)benzoyl]-4-(cyanomethyl)-2-(1H-indol-3-yl-methyl)piperazine (0.32 g) and ammonium chloride (0.17 g) in dimethylformamide (5 ml). The mixture was stirred at 115° C. for 16 hours. Additional sodium azide and ammonium chloride were added to the reaction mixture until the starting material was consumed. After cooling, the mixture was poured into ice-cold water. The resulting precipitate was collected by filtration, washed with water and dried. The precipitate was treated with 4N hydrogen chloride in dioxane solution to give (2R)-1-[3,5-bis(trifluoromethyl)benzoyl]-2-(1H-indol-3-yl-methyl)-4-(1H-tetrazol-5-yl-methyl)piperazine hydrochloride (0.19 g).

IR (Nujol): 3280, 2700–2300, 1635 cm$^{-1}$

NMR (DMSO-d$_6$, δ): 2.75–5.12 (11H, m); 6.54–8.30 (8H, m); 10.94 (1H, s)

MASS:.: 538 (M+1) (free)

Example 67

To a stirred mixture of (2R)-4-(3-aminopropyl)-1-[3,5-bis(trifluoromethyl)benzoyl]-2-(1H-indol-3-yl-methyl)-piperazine (0.20 g) and triethylamine (0.06 ml) in tetrahydrofuran (10 ml) was added 4-nitrophenyl chloroformate (0.08 g) under ice-cooling. After 35 minutes, the resulting precipitate was filtered off. To the filtrate were added triethylamine (0.06 ml) and 30% methylamine in ethanol (0.05 ml) at room temperature. After stirring for 1 hour and 40 minutes, additional 30% methylamine in ethanol (0.05 ml) was added to the reaction mixture and then stirred for 45 minutes. The reaction mixture was concentrated in vacuo and the residue was partitioned between dichloromethane and water. The organic layer was separated, washed with aqueous saturated sodium chloride solution and dried over magnesium sulfate. After evaporation of the solvent in vacuo, the residue was purified by column chromatography on silica gel eluting with a mixed solvent of dichloromethane and methanol (100:3). The eluate was treated with 4N hydrogen chloride in dioxane solution to afford (2R)-1-[3,5-bis(trifluoromethyl)-benzoyl]-2-(1H-indol-3-yl-methyl)-4-[3-(3-methylureido)propyl]piperazine hydrochloride (0.08 g).

IR (Nujol): 3240, 2580, 1633 cm$^{-1}$

NMR (DMSO-d$_6$, δ): 1.72–2.03 (2H, m); 2.55, 2.56 (3H, 2 s); 2.92–5.21 (15H, m); 6.60–8.29 (8H, m); 10.97 (1H, s); 11.12–11.45 (1H, m)

MASS: 570 (M+1) (free)

Example 68

Phenylacetaldehyde (80 mg) was added to a solution of (2R)-2-benzyl-1-(3,5-dimethylbenzoyl)piperazine (200 mg) in methanol (10 ml) at room temperature and stirred for 4 hours. Sodium borohydride (20 mg) was added to the reaction mixture under ice-cooling. The mixture was stirred at room temperature for 5 hours and concentrated in vacuo. The residue was partitioned between dichloromethane and aqueous saturated sodium bicarbonate solution. The organic layer was separated, washed with brine and dried over magnesium sulfate. After evaporation of the solvent in vacuo, the residue was purified on a silica gel column eluting with a mixture of toluene and ethyl acetate to give (2R)-2-benzyl-1-(3,5-dimethylbenzoyl)-4-(2-phenethyl)piperazine (70 mg).

IR (Neat): 3400, 3020, 2910, 2860, 2800, 1627–1592 cm$^{-1}$

NMR (DMSO-d$_6$, δ): 2.21 (6H, s); 1.84–4.88 (13H, m); 6.30–7.49 (13H, m)

MASS: 413 (M+1)

Example 69

To a stirred solution of (2R)-2-(benzo[b]thiophen-3-yl-methyl)-4-benzyl-1-[3,5-bis(trifluoromethyl)benzoyl]-piperazine (0.75 g) in dichloromethane (8 ml) was added dropwise 1-chloroethyl chloroformate (0.19 ml) at ice-bath temperature. The resulting mixture was stirred at room temperature for 1 hour and then at reflux temperature for 5 hours. The reaction mixture was evaporated under reduced pressure. Methanol (5 ml) was added to the residue and the whole mixture was heated under refluxing for 1 hour. The mixture was concentrated in vacuo and the residue was partitioned between aqueous sodium bicarbonate solution (10 ml) and ethyl acetate (20 ml). The organic layer was separated, washed with brine and dried over magnesium sulfate. After evaporation of the solvent in vacuo, the residue was treated with 4N hydrogen chloride in ethyl acetate solution to afford (2R)-2-(benzo[b]thiophen-3-yl-methyl)-1-[3,5-bis(trifluoromethyl)benzoyl]piperazine hydrochloride (0.69 g).

mp: 145°–155° C.

[α]$_D^{24}$: +5.38° (C=0.13, MeOH)

IR (Nujol): 3300, 2900–2400, 1625, 1430, 1350 cm$^{-1}$

NMR (DMSO-d$_6$, δ): 3.0–4.0 (9H, m); 4.2–4.3 (1H, m); 7.0–8.4 (8H, m); 9.5–10.2 (1H, m)

MASS: 473 (M+1) (free)

Example 70

To a solution of (2R)-2-benzyl-1-[3,5-bis(trifluoromethyl)benzoyl]-4-[(4R)-4-hydroxy-1-tert-butoxycarbonyl-L-propyl]piperazine (0.68 g) in dichloromethane (10 ml) was added 4N hydrogen chloride in dioxane solution (10 ml) at 0° C. The resulting mixture was stirred at the same temperature for 1 hour and then concentrated under reduced pressure. The residue was pulverized with ethyl ether, collected by filtration and washed with ethyl ether to give (2R)-2-benzyl-1-[3,5-bis(trifluoromethyl)benzoyl]-4-[(4R)-4-hydroxy-L-propyl]piperazine hydrochloride (0.57 g).

mp: 234°–236° C.

IR (Nujol): 3300,1635 cm$^{-1}$

NMR (DMSO-d$_6$, δ): 1.83–2.73 (2H, m); 2.79–5.23 (13H, m); 5.52, 5.65 (1H, 2 br s); 6.84–8.25 (8H, m); 8.80 (1H, br s); 10.00 (1H, br s)

MASS: 530 (M+1) (free)

Example 71

(2R)-2-Benzyl-1[3,5-bis(trifluoromethyl)benzoyl]-4-[(4R)-4-hydroxy-1-(1-methyl-1H-indol-3-yl-carbonyl)-L-propyl]piperazine (0.21 g) was obtained from (2R)-2-benzyl-1-[3,5-bis(trifluoromethyl)benzoyl]-4-[(4R)-4-hydroxy-L-propyl]piperazine hydrochloride (300 mg) and 1-methyl-1H-indole-3-carboxylic acid (90 mg) by a similar manner to that of Example 61.

mp: >150° C.

IR (Nujol): 3330, 1633, 1527 cm$^{-1}$

NMR (DMSO-d$_6$, δ): 1.85–2.28 (2H, m); 2.52–5.46 (14H, m); 3.86 (3H, s); 6.88–8.32 (13H, m)

MASS: 687 (M+1)

Example 72

To a mixture of (2R)-1-[3,5-bis(trifluoromethyl)-benzoyl]-4-(3-carboxypropyl)-2-(1H-indol-3-yl-methyl)-piperazine (180 mg), 4-piperidinopiperidine (56 mg) and 1-hydroxybenzotriazole hydrate (45 mg) in dichloromethane (4 ml) was added 1-(3-dimethylaminopropyl)-3-ethylcarbodiimide hydrochloride (64 mg) at ice-bath temperature. After stirring for 30 minutes, the reaction mixture was allowed to warm to room temperature and was stirred for 2 hours and 40 minutes. The reaction mixture was concentrated under reduced pressure and the resulting residue was partitioned between ethyl acetate and water. The organic layer was washed successively with aqueous saturated sodium bicarbonate and brine, and dried over magnesium sulfate. After evaporation of the solvent, the residue was purified by column chromatography on silica gel eluting with a mixture of dichloro-methane and methanol (10:1) to give (2R)-1-[3,5-bis(trifluoromethyl)benzoyl]-4-[3-(4,1'-bipiperidin-1-yl-carbonyl)-propyl]-2-(1H-indol-3-yl-methyl)piperazine, which was converted to the corresponding dihydrochloride salt (0.18 g) by treatment with 4N hydrogen chloride in dioxane solution.

IR (Nujol): 3350, 2630, 1626 cm$^{-1}$

NMR (DMSO-d$_6$, δ): 1.17–2.24 (12H, m); 2.34–5.22 (22H, m); 6.57–8.29 (8H, m); 10.22–10.60 (1H, m); 10.97 (1H, s); 10.83–11.57 (1H, m)

MASS: 692 (M+1) (free)

Example 73

To a stirred mixture of trans-3-(3-pyridyl)acrylic acid (100 mg) and triethylamine (0.19 ml) in dichloromethane (10 ml) was added 1-naphthoyl chloride (0.1 ml) at −15° C. After stirring for 30 minutes, a solution of (2S)-1-[3,5-bis(trifluoromethyl)benzoyl]-2-(3,4-dimethylbenzyl)piperazine (300 mg) in dichloromethane (10 ml) was added at −15° C. and the resulting mixture was stirred for 30 minutes at the same temperature and then for 1 hour at room temperature. Dichloromethane and water were added to the reaction mixture and the organic layer was separated, washed successively with aqueous saturated sodium bicarbonate solution, water, 0.5N hydrochloric acid and brine, and dried over magnesium sulfate. After evaporation of the solvent in vacuo, the residue was purified on a silica gel column (20 g) eluting with a mixture of dichloromethane and methanol (100:2) to give (2S)-1-[3,5-bis(trifluoromethyl)benzoyl]-2-(3,4-dimethyl benzyl)-4-(3-(3-pyridyl)-trans-acryloyl]piperazine (0.34 g).

IR (Nujol): 3430, 1637, 1607 cm$^{-1}$

NMR (CDCl$_3$, δ): 2.13, 2.22 (6H, 2 s); 2.60–5.38 (9H, m); 6.45–8.91 (12H, m)

MASS: 576 (M+1)

Example 74

A mixture of (2R)-1-[3,5-bis(trifluoromethyl)-benzoyl]-2-(1H-indol-3-ylmethyl)piperazine (1.5 g), benzyl 2-bromoacetate (0.79 g), triethylamine (0.55 ml) and tetrahydrofuran (15 ml) was stirred overnight at room temperature. The resulting insoluble material was removed by filtration and the filtrate was concentrated under reduced pressure. The residue was purified by column chromatography on silica gel eluting with a mixture of dichloromethane and methanol (30:1) to give (2R)-4-(benzyloxycarbonylmethyl)-1-[3,5-bis(trifluoromethyl)-benzoyl]-2-(1H-indol-3-ylmethyl)piperazine (1.92 g).

[α]$_D^{21}$: −11.6 (C=1.0, MeOH)

IR (Neat): 3600–3100, 1735, 1626, 1275, 1129, 900 cm$^{-1}$

NMR (DMSO-d$_6$, δ): 2.20–5.20 (13H, m); 6.60–8.20 (13H, m); 10.85 (1H, br s)

MASS: 604 (M+1), 454

Example 75

A mixture of (2R)-4-(benzyloxycarbonylmethyl)-1-[3,5-bis(trifluoromethyl)benzoyl]-2-(1H-indol-3-ylmethyl)-piperazine (1.86 g), 10% Pd charcoal (0.186 g) and tetrahydrofuran (93 ml) was stirred for 17 hours under hydrogen gas atmosphere (1 atm). The catalyst was removed by filtration and the filtrate was concentrated. The residue was triturated with ethyl ether to give (2R)-4-(carboxymethyl)-1-[3,5-bis(trifluoromethyl)benzoyl]-2-(1H-indol-3-ylmethyl)piperazine (0.83 g) as a white powder.

[α]$_D^{19}$: −3.0° (C=0.5, DMF)

mp: 152°–156° C.

IR (Nujol): 3600 –3100, 1654, 1630, 1277, 1196, 1130 cm$^{-1}$

NMR (DMSO-d$_6$, δ): 2.20–5.20 (11H, m); 6.60–8.20 (8H, m); 10.85 (1H, s)

MASS: 514 (M+1)

Example 76

To a stirred solution of (2R)-4-(carboxymethyl)-1-[3,5-bis(trifluoromethyl)benzoyl]-2-(1H-indol-3-ylmethyl)- piperazine (1 g) in dry dimethylformamide (10 ml) was added 1-hydroxybenzotriazole (0.29 g) and 1-(3-dimethylaminopropyl)-3-ethylcarbodiimide hydrochloride (0.41 g) at room temperature. After stirring for 15 minutes at room temperature, 1-amino-4-methylpiperazine (320 mg) was added and further stirred for 5 hours at the same temperature. The reaction mixture was poured into a solution of sodium hydrogencarbonate (1.8 g) in water (100 ml) and extracted three times with 20 ml portions of ethyl acetate. The organic layers were combined and washed with brine (30 ml). The organic layer was dried over magnesium sulfate and filtered and the solvent was removed by rotary evaporator. The crude product was purified by chromatography (silica gel, dichloromethane:methanol, 5:1) to afford (2R)-1-[3,5-bis(trifluoromethyl)benzoyl]-2-(1H-indol-3-ylmethyl)-4-[N-(4-methyl-1-piperazinyl)carbamoylmethyl]piperazine (0.94 g) as a yellowish powder.

IR (Nujol): 3180, 1680, 1630, 1276, 1170, 1130, 1005, 897 cm$^{-1}$

NMR (DMSO-d$_6$, δ): 2.16 (3H, s); 2.0–5.0 (19H, m); 6.6–8.2 (8H, m), 8.47, 8.77 (1H, 2 s); 10.85 (1H, s)

Example 77

(2R)-1-[3,5-Bis(trifluoromethyl)benzoyl]-2-(1H-indol-3-ylmethyl)-4-[N-(4-methyl-1-piperazinyl)carbamoylmethyl]-piperazine (10.89 g) and fumaric acid (2.07 g) were dissolved in ethanol (50 ml) at 70° C. After cooling, the resulting solution was concentrated under reduced pressure to give a powder (13.18 g). The powder (9.68 g) was dissolved in 2-butanone (194 ml) at reflux temperature and the solution was allowed to stir at room temperature to afford crystals, which was collected by filtration and dried to give fumarate salt of (2R)-1-[3,5-bis(trifluoromethyl)benzoyl]-2-(1H-indol-3-ylmethyl)-4-[N-(4-methyl-1-piperazinyl) carbamoylmethyl]piperazine (7.94 g).

mp: 169.5°–171° C.

IR (Nujol): 3220, 1700, 1653, 1630, 1275, 1217, 1168, 1122, 979, 894, 730 cm$^{-1}$ NMR (DMSO-d$_6$, δ): 2.23, 2.26 (3H, 2 s); 2.10–4.93 (19H, m); 6.60 (2H, s); 6.54–8.23 (8H, m); 8.50, 8.85 (1H, 2 s); 10.85 (1H, s)

Example 78

A mixture of (2R)-1-[3,5-bis(trifluoromethyl)-benzoyl]-2-(1H-indol-3-ylmethyl)piperazine (120 mg), 4-chloromethyl-2-(2-methoxyethylcarbonylamino)thiazole (70 mg) and powdered sodium hydrogen carbonate (27 mg) in dry dimethylformamide was stirred for 5 hours and 20 minutes at 60° C. The reaction mixture was powered into water and the resulting precipitate was collected by filtration. The crude product was purified by column chromatography on silica gel eluting with a mixture of dichloromethane and methanol (30:1). The eluate was evaporated under reduced pressure and treated with 17.6% hydrogen chloride in ethanol (0.12 ml) to give (2R)-1-[3,5-bis(trifluoromethyl)benzoyl]-2-(1H-indol-3-ylmethyl)-4-[[2-(3-methoxypropanoylamino)thiazol-4-yl]methyl]piperazine hydrochloride (140 mg).

$[\alpha]_D^{22}$: -34.0° (C=0.5, MeOH)

IR (Nujol): 3650–3100, 2750–2000, 1635, 1275, 1130, 900 cm$^{-1}$

NMR (DMSO-d$_6$, δ): 2.60–5.20 (18H, m); 6.60–8.21 (9H, m); 10.90–11.00 (1H, m); 11.20–12.00 (1H, m); 12.19 (1H, s)

MASS: 654 (M+1) (free)

Example 79

The following piperazine derivatives (Table 12) were prepared by the similar manner to that of the each Example No. defined in the "Process" column. The physical properties of the object compounds are shown after the table.

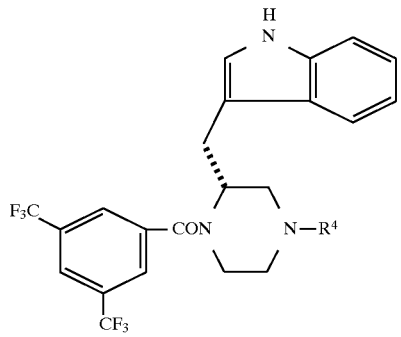

TABLE 12

| Example No. | Object Compounds R$^4$ | Salt | Starting Compound | Process |
|---|---|---|---|---|
| 79-1) | —CH$_2$—[thiazole]—NHCOCH$_3$ | HCl | Ex. 6 | Ex. 78 |
| 79-2) | —CH$_2$—[thiazole]—NHCOOC$_2$H$_5$ | HCl | Ex. 6 | Ex. 78 |
| 79-3) | —CH$_2$—[thiazole]—NHCO—[phenyl] | HCl | Ex. 6 | Ex. 78 |

TABLE 12-continued

| Example No. | Object Compounds R⁴ | Salt | Starting Compound | Process |
|---|---|---|---|---|
| 79-4) | —CH₂—[thiazole]—NHCOC(CH₃)₃ | HCl | Ex. 6 | Ex. 78 |
| 79-5) | —CH₂—[thiazole]—NHCO-cyclopropyl | HCl | Ex. 6 | Ex. 78 |
| 79-6) | —CH₂—[thiazole]—NHCOC₃H₇ | HCl | Ex. 6 | Ex. 78 |
| 79-7) | —CH₂—[thiazole]—NHCOC₂H₅ | HCl | Ex. 6 | Ex. 78 |
| 79-8) | —CH₂—[thiazole]—NHCHO | HCl | Ex. 6 | Ex. 78 |
| 79-9) | —CH₂—[pyridine]—NHCOCH₃ | 2HCl | Ex. 6 | Ex. 78 |
| 79-10) | —CH₂—[thiazole(COOC₂H₅)]—NHCOC₃ | HCl | Ex. 6 | Ex. 78 |
| 79-11) | —CH₂—[thiazole]—NH₂ | — | Ex. 6 | Ex. 14 |
| 79-12) | —CH₂—[thiazole]—NH₂ | 2HCl | Ex. 79-11) | Ex. 23 |
| 79-13) | —CH₂—[thiazole]—NHSO₂CH₃ | HCl | Ex. 79-11) | Ex. 40 |
| 79-14) | —COCH₂—[thiazole]—NHCOCH₃ | — | Ex. 6 | Ex. 16 |
| 79-15) | —CH₂—[thiadiazole]—NHCOCH₃ | HCl | Ex. 6 | Ex. 78 |
| 79-16) | —CH₂—[thiazole]—N(CH₃)—COC₂H₅ | HCl | Ex. 6 | Ex. 78 |

Physical properties of the compounds of the Example 79:

Example 79–1)

$[\alpha]_D^{24}$: 30.2° (C=0.5, MeOH)

mp: 185°–189° C.

IR (Nujol): 3660–3100, 2800–2000, 1635, 1545, 1276, 1183, 1130, 900 cm⁻¹

NMR (DMSO-d₆, δ): 1.36–5.10 (14H, m); 6.59–8.22 (10H, m); 10.90–11.00 (1H, m); 12.15 (1H, s)

MASS: 610 (M+1) (free),456

Example 79–2)

$[\alpha]_D^{22}$: –33.4° (C=0.5, MeOH)

IR (Nujol): 3650–3100, 2800–2000, 1715, 1635, 1555, 1274, 1130, 900 cm$^{-1}$

NMR (DMSO-d$_6$, δ): 1.25 (3H, t, J=7.1 Hz); 2.73–5.10 (13H, m); 6.60–8.30 (9H, m); 10.90–11.00 (1H, m); 11.81 (1H, br s)

MASS: 640 (M+1) (free), 456

Example 79–3)

$[α]_D^{22}$: –42.0° (C=0.5, MeOH)

IR (Nujol): 3600–3100, 2750–2000, 1635, 1540, 1277, 1175, 1130 cm$^{-1}$

NMR (DMSO-d$_6$, δ): 2.73–5.20 (11H, m); 6.59–8.21 (14H, m); 10.90–11.00 (1H, m); 12.69 (1H, s)

MASS: 672 (M+1) (free), 456

Example 79–4)

$[α]_D^{22}$: –24.2° (C=0.5, MeOH)

IR (Nujol): 3650–3100, 2750–2000, 1635, 1540, 1276, 1170, 1129, 900 cm$^{-1}$

NMR (DMSO-d$_6$, δ): 1.23 (9H, s); 2.73–5.10 (11H, m); 6.50–8.20 (9H, m); 10.80–11.00 (1H, m); 11.84 (1H, s)

MASS: 652 (M+1) (free), 456

Example 79–5)

$[α]_D^{22}$: –35.8° (C=0.5, MeOH)

IR (Nujol): 3650–3100, 2750–2000, 1635, 1540, 1276, 1170, 1130, 900 cm$^{-1}$

NMR (DMSO-d$_6$, δ): 0.80–1.00 (4H, m); 1.90–2.00 (1H, m); 2.73–5.15 (11H, m); 6.60–8.21 (9H, m); 10.90–11.00 (1H, m); 12.43 (1H, m)

MASS: 636 (M+1) (free), 456

Example 79–6)

$[α]_D^{22}$: –30.4° (C=0.5, MeOH)

IR (Nujol): 3650–3100, 2750–2000, 1635, 1542, 1275, 1170, 1131, 900 cm$^{-1}$

NMR (DMSO-d$_6$, δ): 0.89 (3H, t, J=7.4 Hz); 1.56–1.67 (2H, m); 2.40–2.50 (2H, m); 2.73–5.15 (11H, m); 6.56–8.21 (9H, m); 10.90–10.94 (1H, m); 12.12 (1H, s)

MASS: 638 (M+1) (free)

Example 79–7)

$[α]_D^{22}$: –34.0° (C=0.5, MeOH)

IR (Nujol): 3650–3100, 2750–2000, 1635, 1543, 1277, 1170, 1130, 900 cm$^{-1}$

NMR (DMSO-d$_6$, δ): 1.08 (3H, t, J=7.4 Hz), 2.43–2.50 (2H, m); 2.73–5.15 (11H, m); 6.55–8.21 (9H, m); 10.90–10.94 (1H, m); 12.11 (1H, s)

MASS: 624 (M+1) (free)

Example 79–8)

$[α]_D^{22}$: –15.2° (C=0.5, MeOH)

IR (Nujol): 3600–3100, 2750–2000, 1635, 1278, 1172, 1130, 900 cm$^{-1}$

NMR (DMSO-d$_6$, δ): 2.73–5.20 (11H, m); 6.60–8.52 (11H, m); 10.94 (1H, s)

MASS: 596 (M+1) (free), 456

Example 79–9)

$[α]_D^{22}$: –20.6° (C=0.5, MeOH)

IR (Nujol): 3650–3100, 2750–2000, 1635, 1276, 1170, 1129, 900 cm$^{-1}$

NMR (DMSO-d$_6$, δ): 2.09 (3H, s); 2.73–5.20 (11H, m); 6.60–8.20 (11H, m); 10.46 (1H, s); 10.91 (1H, s)

MASS: 604 (M+1) (free)

Example 79–10)

$[α]_D^{22}$: –13.0° (C=0.5, MeOH)

IR (Nujol): 3650–3050, 2750–2000, 1685, 1636, 1524, 1275, 1130, 900 cm$^{-1}$

NMR (DMSO-d$_6$, δ): 1.31 (3H, t, J=6.5 Hz), 2.24 (3H, s); 2.73–5.20 (13H, m); 6.66–8.25 (8H, m); 10.94 (1H, s); 12.71 (1H, s)

MASS: 682 (M+1) (free)

Example 79–11)

$[α]_D^{22}$: –20.8° (C=0.5, MeOH)

IR (Neat): 3700–3000, 1615, 1515, 1272, 1125, 900 cm$^{-1}$

NMR (DMSO-d$_6$, δ): 2.00–5.00 (13H, m); 6.38–8.20 (9H, m); 10.80 (1H, s)

MASS: 568 (M+1), 456

Example 79–12)

$[α]_D^{22}$: –10.4° (C=0.5, MeOH)

IR (Nujol): 3650–3100, 2750–2000, 1635, 1277, 1130 cm$^{-1}$

NMR (DMSO-d$_6$, δ): 3.00–5.20 (11H, m); 6.60–8.30 (11H, m); 10.95 (1H, s)

MASS: 568 (M+1) (free), 456

Example 79–13)

$[α]_D^{22}$: –31.8° (C=0.5, MeOH)

IR (Nujol): 3270, 2750–2000, 1637, 1531, 1279, 1124, 964 cm$^{-1}$

NMR (DMSO-d$_6$, δ): 2.73–5.15 (14H, m); 6.60–8.25 (10H, m); 10.89 (1H, s)

MASS: 646 (M+1) (free), 568, 456

Example 79–14)

$[α]_D^{22}$: 11.8° (C=0.5, MeOH)

IR (Nujol): 3650–3100, 1625, 1543, 1275, 1130 cm$^{-1}$

NMR (DMSO-d$_6$, δ): 2.09–2.11 (3H, m); 2.52–5.00 (11H, m); 6.63–8.20 (9H, m); 10.85 (1H, s); 12.07 (1H, s)

MASS: 638 (M+1), 456

Example 79–15)

$[α]_D^{22}$: –51.60 (C=0.5, MeOH)

IR (Nujol): 3650–3100, 2750–2000, 1634, 1540, 1274, 1170, 1127, 900 cm$^{-1}$

NMR (DMSO-d$_6$, δ): 2.31 (3H, s); 2.73–5.35 (11H, m); 6.63–8.25 (8H, m); 10.94–11.00 (1H, m); 13.20 (1H, s)

MASS: 611 (M+1) (free)

Example 79–16)

$[α]_D^{22}$: –23.4° (C=0.5, MeOH)

IR (Nujol): 3650–3000, 2750–2000, 1620, 1274, 1175, 1128, 900 cm$^{-1}$

NMR (DMSO-d$_6$, δ): 1.10 (3H, t, J=7.2 Hz); 2.60–5.10 (16H, m); 6.50–8.21 (9H, m); 10.91 (1H, s); 11.50–11.90 (1H, br s)

MASS: 638 (M+1) (free)

What we claim is:

1. A compound of the formula:

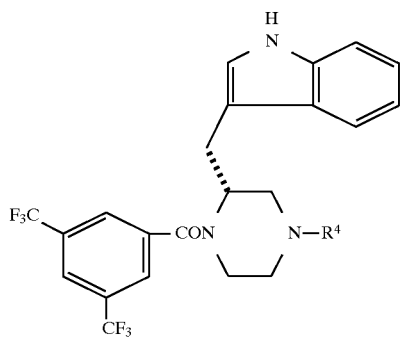

wherein $R^4$ is a group of the formula —A–Z, wherein A is a direct bond, wherein Z is selected from the group consisting of

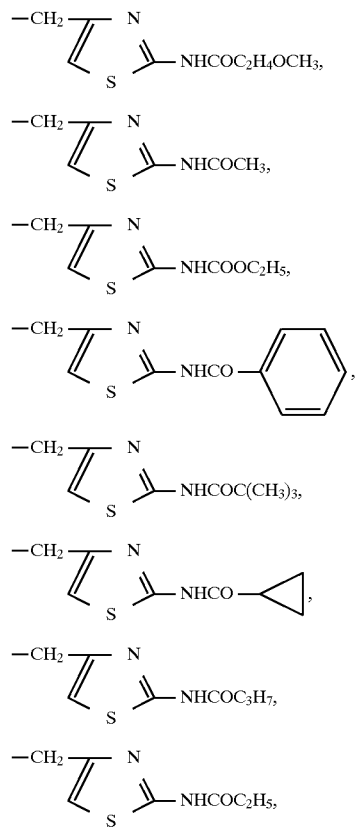

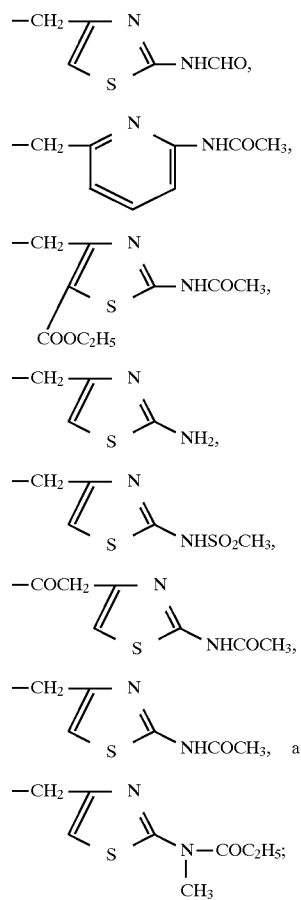

or a pharmaceutically acceptable salt thereof.

2. (2R)-1-(3,5-Bis-(trifluoromethyl)benzoyl)-2-(1H-indol-3-ylmethyl)-4-((N-(4-methyl-1-piperazinyl)carbamoylmethyl)-piperazine fumarate.

3. A method for treating or preventing asthma, which comprises administering an effective amount of a compound of claim 1 or 2 to a human being or an animal in need thereof.

4. A pharmaceutical composition, comprising the compound of claim 1 or 2 as an active ingredient, in association with a pharmaceutically acceptable carrier.

* * * * *